US009663510B2

(12) United States Patent
Schulze et al.

(10) Patent No.: US 9,663,510 B2
(45) Date of Patent: May 30, 2017

(54) SUBSTITUTED TRIAZOLOPYRIDINES AND THEIR USE AS TTK INHIBITORS

(71) Applicants: Bayer Intellectual Property GmbH, Monheim (DE); BAYER PHARMA AKTIENGESELLSCHAFT, Berlin (DE)

(72) Inventors: Volker Schulze, OT Bergfelde (DE); Dirk Kosemund, Berlin (DE); Antje Margret Wengner, Berlin (DE); Gerhard Siemeister, Berlin (DE); Detlef Stöckigt, Potsdam (DE); Michael Brüning, Schildow, DE (US)

(73) Assignees: BAYER PHARMA AKTIENGESELLSCHAFT, Berlin (DE); BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/362,836

(22) PCT Filed: Dec. 10, 2012

(86) PCT No.: PCT/EP2012/074978
§ 371 (c)(1),
(2) Date: Jun. 4, 2014

(87) PCT Pub. No.: WO2013/087579
PCT Pub. Date: Jun. 20, 2013

(65) Prior Publication Data
US 2015/0210683 A1 Jul. 30, 2015

(30) Foreign Application Priority Data

Dec. 12, 2011 (EP) ...................... 11193011

(51) Int. Cl.
*C07D 471/04* (2006.01)
*A61K 31/7028* (2006.01)
*A61K 31/437* (2006.01)
*A61K 45/06* (2006.01)

(52) U.S. Cl.
CPC .......... *C07D 471/04* (2013.01); *A61K 31/437* (2013.01); *A61K 31/7028* (2013.01); *A61K 45/06* (2013.01)

(58) Field of Classification Search
CPC .. A61K 31/437; A61K 31/7028; A61K 45/06; C07D 471/04
See application file for complete search history.

(56) References Cited

FOREIGN PATENT DOCUMENTS

| WO | 2005030121 A2 | 4/2005 |
|---|---|---|
| WO | 2007065010 A2 | 6/2007 |
| WO | 2008025821 A1 | 3/2008 |
| WO | 2009010530 A1 | 1/2009 |
| WO | 2009024824 A1 | 2/2009 |
| WO | 2009027283 A1 | 3/2009 |
| WO | 2009047514 A1 | 4/2009 |
| WO | 2009068482 A1 | 6/2009 |
| WO | 2010092015 A1 | 8/2010 |
| WO | 2010092041 A1 | 8/2010 |
| WO | 2010124826 A1 | 11/2010 |
| WO | 2011026579 A1 | 3/2011 |
| WO | 2011063907 A1 | 6/2011 |
| WO | 2011063908 A1 | 6/2011 |
| WO | 2011064328 A1 | 6/2011 |
| WO | 2011086098 A1 | 7/2011 |
| WO | 2011086099 A1 | 7/2011 |
| WO | 2011092272 A1 | 8/2011 |

OTHER PUBLICATIONS

Chabner et. al., Nature Reviews Cancer, 2005, Nature Publishing Group, vol. 5, pp. 65-72.*
Leaf, Fortune, 2004, Time Inc., pp. 1-13.*
Abrieu, et al., "Mps1 is a Kinetochore-Associated Kinase Essential for the Vertebrate Mitotic Checkpoint," Cell, Jul. 13, 2001, 106:83-93.
Berge et al., "Pharmaceutical Salts," Journal of Pharmaceutical Sciences, Jan. 1977, 66(1):1-19.
Dorer et al., "A Small-Molecule Inhibitor of Mps1 Blocks the Spindle-Checkpoint Responseto a Lack of Tension on Mitotic Chromosomes," Current Biology, Jun. 7, 2005, 15:1070-1076.
East et al., "DNA gyrase (GyrB)/topoisomerase IV (ParE) inhibitors: Synthesis and antibacterial activity," Bioorganic & Med. Chem. Letters, 2009, 19:894-899.
Fowler et al., "Selective Reduction of Radiotracer Trapping by Deuterium Substitution: Comparison of Carbon-I I-L-Deprenyl and Carbon-11-Deprenyl-D2 for MAO B Mapping," The Journal of Nuclear Medicine, 36(7):1255-1262, 1995.
Jelluma et al., "Chromosomal Instability by Inefficient Mps1 Auto-Activation Due to a Weakened Mitotic Checkpoint and Lagging Chromosomes," PloS One, Jun. 2008, 3:1-8.

(Continued)

*Primary Examiner* — Sarah Pihonak
(74) *Attorney, Agent, or Firm* — Morrison and Foerster LLP

(57) ABSTRACT

The present invention relates to substituted triazolopyridine compounds of general formula (I):

in which $R^1$, $R^2$, $R^3$, $R^4$, and $R^5$ are as given in the description and in the claims, to methods of preparing said compounds, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

27 Claims, No Drawings

(56) References Cited

OTHER PUBLICATIONS

Jones et al., "Chemical Genetics Reveals a Role for Mps1 Kinase in Kinetochore Attachment during Mitosis," Current Biology, Jan. 26, 2005, 15:160-165.
King, R., "When 2+2=5: The origins and fates of aneuploid and tetraploid cells," Biochimica et Biophysica Acta, 2008, 1786:4-14.
Kops et al., "On the Road to Cancer: Aneuploidy and the Mitotic-checkpoint," Nature Reviews/Cancer, Oct. 2005, 5:773-785.
Musacchio et al., "The spindle-assembly checkpoint in space and time," Nature Reviews/Molecular Cell Biology, May 2007, 8:379-393.
Schmidt, et al., "Mitotic drug targets and the development of novel anti-mitotic anticancer drugs," Drug Resistance Updates, 2007, 10:162-181.
Schmidt et al., "Ablation of the spindle assembly checkpoint by a compound targeting Mps1," EMBO Reports, 2005, 6(9):866-872.
Schmidt et al., "Exploiting the Compromised Spindle Assembly Checkpoint Functionof Tumor Cells," Cell Cycle, Jan. 2006, 5(2):159-163.
Suijkerbuijk et al., "Preventing aneuploidy: The contribution of mitotic checkpoint proteins," Biochimica et Biophysica Acta, 2008, 1786:24-31.
Weaver et al., "Aneuploidy: Instigator and Inhibitor of Tumorigenesis," Cancer Research, 2007, 67(21):10103-10105.
Yuan et al., "Increased Expression of Mitotic Checkpoint Genes in Breast Cancer Cells with Chromosomal Instability," Clinical Cancer Research, Jan. 15, 2006, 12(2):405-410.
Chemical Abstract XP-002574925, 2009.
Chemical Abstract XP-002574926, 2009.
Chemical Abstract XP-002574927, 2009.
Chemical Abstract XP-002574929, 2009.
Chemical Abstract XP-002574930, 2009.
Chemical Abstract XP-002574931, 2009.
Chemical Abstract XP-002574932, 2009.
Chemical Abstract XP-002574933, 2009.
Chemical Abstract XP-002574934, 2009.
Chemical Abstract XP-002574935, 2009.
Related copending U.S. Appl. No. 13/512,701, filed Sep. 14, 2012.
Related copending U.S. Appl. No. 13/512,721, filed Aug. 13, 2012.
Related copending U.S. Appl. No. 13/704,859, filed Feb. 25, 2013.
Related copending U.S. Appl. No. 14/113,017, filed Jan. 6, 2014.
Related copending U.S. Appl. No. 14/362,836, filed Jun. 4, 2014.
The Merck Index. (2013). "Capecitabine," No. 1757, pp. 305-306.
The Merck Index. (2013). "Rituximab," No. 8367, p. 1503.

* cited by examiner

SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Biotinylated peptide (C-terminus in amide form)

<400> SEQUENCE: 1

Pro Trp Asp Pro Asp Asp Ala Asp Ile Thr Glu Ile Leu Gly
1               5                   10

SUBSTITUTED TRIAZOLOPYRIDINES AND THEIR USE AS TTK INHIBITORS

The present invention relates to substituted triazolopyridine compounds of general formula (I) as described and defined herein, to methods of preparing said compounds, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

BACKGROUND OF THE INVENTION

The present invention relates to chemical compounds that inhibit Mps-1 (Monopolar Spindle 1) kinase (also known as Tyrosine Threonine Kinase, UK). Mps-1 is a dual specificity Ser/Thr kinase which plays a key role in the activation of the mitotic checkpoint (also known as spindle checkpoint, spindle assembly checkpoint) thereby ensuring proper chromosome segregation during mitosis [Abrieu A et al., Cell, 2001, 106, 83-93]. Every dividing cell has to ensure equal separation of the replicated chromosomes into the two daughter cells. Upon entry into mitosis, chromosomes are attached at their kinetochores to the microtubules of the spindle apparatus. The mitotic checkpoint is a surveillance mechanism that is active as long as unattached kinetochores are present and prevents mitotic cells from entering anaphase and thereby completing cell division with unattached chromosomes [Suijkerbuijk S J and Kops G J, Biochemica et Biophysica Acta, 2008, 1786, 24-31; Musacchio A and Salmon E D, Nat Rev Mol Cell Biol., 2007, 8, 379-93]. Once all kinetochores are attached in a correct amphitelic, i.e. bipolar, fashion with the mitotic spindle, the checkpoint is satisfied and the cell enters anaphase and proceeds through mitosis. The mitotic checkpoint consists of a complex network of a number of essential proteins, including members of the MAD (mitotic arrest deficient, MAD 1-3) and Bub (Budding uninhibited by benzimidazole, Bub 1-3) families, the motor protein CENP-E, Mps-1 kinase as well as other components, many of these being over-expressed in proliferating cells (e.g. cancer cells) and tissues [Yuan B et al., Clinical Cancer Research, 2006, 12, 405-10]. The essential role of Mps-1 kinase activity in mitotic checkpoint signalling has been shown by shRNA-silencing, chemical genetics as well as chemical inhibitors of Mps-1 kinase [Jelluma N et al., PLos ONE, 2008, 3, e2415; Jones M H et al., Current Biology, 2005, 15, 160-65; Dorer R K et al., Current Biology, 2005, 15, 1070-76; Schmidt M et al., EMBO Reports, 2005, 6, 866-72].

There is ample evidence linking reduced but incomplete mitotic checkpoint function with aneuploidy and tumorigenesis [Weaver B A and Cleveland D W, Cancer Research, 2007, 67, 10103-5; King R W, Biochimica et Biophysica Acta, 2008, 1786, 4-14]. In contrast, complete inhibition of the mitotic checkpoint has been recognised to result in severe chromosome missegregation and induction of apoptosis in tumour cells [Kops G J et al., Nature Reviews Cancer, 2005, 5, 773-85; Schmidt M and Medema R H, Cell Cycle, 2006, 5, 159-63; Schmidt M and Bastians H, Drug Resistance Updates, 2007, 10, 162-81].

Therefore, mitotic checkpoint abrogation through pharmacological inhibition of Mps-1 kinase or other components of the mitotic checkpoint represents a new approach for the treatment of proliferative disorders including solid tumours such as carcinomas and sarcomas and leukaemias and lymphoid malignancies or other disorders associated with uncontrolled cellular proliferation.

Different compounds have been disclosed in prior art which show an inhibitory effect on Mps-1 kinase:
WO 2009/024824 A1 discloses 2-Anilinopurin-8-ones as inhibitors of Mps-1 for the treatment of proliferate disorders. WO 2010/124826 A1 discloses substituted imidazoquinoxaline compounds as inhibitors of Mps-1 kinase. WO 2011/026579 A1 discloses substituted aminoquinoxalines as Mps-1 inhibitors.

Substituted triazolopyridine compounds have been disclosed for the treatment or prophylaxis of different diseases:
WO 2008/025821 A1 (Cellzome (UK) Ltd) relates to triazole derivatives as kinase inhibitors, especially inhibitors of ITK or PI3K, for the treatment or prophylaxis of immunological, inflammatory or allergic disorders. Said triazole derivatives are exemplified as possessing an amide, urea or aliphatic amine substituent in position 2.

WO 2009/047514 A1 (Cancer Research Technology Limited) relates to [1,2,4]-triazolo-[1,5-a]-pyridine and [1,2,4]-triazolo-[1,5-c]-pyrimidine compounds which inhibit AXL receptor tyrosine kinase function, and to the treatment of diseases and conditions that are mediated by AXL receptor tyrosine kinase, that are ameliorated by the inhibition of AXL receptor tyrosine kinase function etc., including proliferative conditions such as cancer, etc. Said compounds are exemplified as possessing a substituent in the 5-position and a substituent in the 2-position.

WO 2009/010530 A1 discloses bicyclic heteroaryl compounds and their use as phosphatidylinositol (PI) 3-kinase. Among other compounds also substituted triazolopyridines are mentioned.

WO 2009/027283 A1 discloses triazolopyridine compounds and their use as ASK (apoptosis signal-regulating kinase) inhibitors for the treatment of autoimmune diseases and neurodegenerative diseases.

WO 2010/092041 A1 (Fovea Pharmaceuticals SA) relates to [1,2,4]-triazolo-[1,5-a]-pyridines, which are said to be useful as selective kinase inhibitors, to methods for producing such compounds and methods for treating or ameliorating kinase-mediated disorder. Said triazole derivatives are exemplified as possessing a 2-chloro-5-hydroxyphenyl substituent in the 6-position of the [1,2,4]-triazolo-[1,5-a]-pyridine.

WO 2011/064328 A1, WO 2011/063907 A1, and WO 2011/063908 A1 (Bayer Pharma AG) relate to [1,2,4]-triazolo-[1,5-a]-pyridines and their use for inhibition of Mps-1 kinase.

WO 2011/064328 A1 discloses compounds of formula S2:

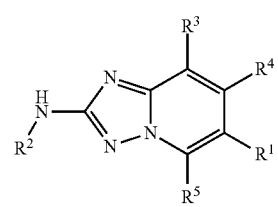

in which
$R^1$ is an aryl- or heteroaryl- group; wherein the aryl- or heteroaryl- group can be substituted inter alia with —N(H)C(=O)$R^6$ or —C(=O)N(H)$R^6$; in which $R^6$ represents a hydrogen or a $C_1$-$C_6$-alkyl- group; the $C_1$-$C_6$-alkyl- group optionally being substituted with halo-, hydroxyl-, $C_1$-$C_3$-alkyl, $R_7O$—. WO 2011/064328 A1 does not disclose compounds of the present invention as defined below.

WO 2011/063907 A1 discloses compounds of formula S1:

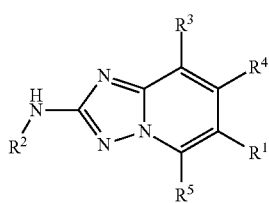

in which
$R^1$ is an aryl group which is substituted at least one time; whereas the at least one substituent inter alia can be —N(H)C(=O)$R^6$ or —C(=O)N(H)$R^6$; in which $R^6$ represents a group selected from $C_3$-$C_6$-cycloalkyl, 3- to 10-membered heterocyclyl-, aryl-, heteroaryl-, —(CH$_2$)$_q$—(C$_3$-C$_6$-cycloalkyl), —(CH$_2$)$_q$— (3- to 10-membered heterocyclyl), —(CH$_2$)$_q$-aryl, or —(CH$_2$)$_q$-heteroaryl, wherein $R^6$ is optionally substituted, and q is 0, 1, 2 or 3;
$R^2$ represents a substituted or unsubstituted aryl- or heteroaryl- group;
$R^3$ and $R^4$ inter alia can be hydrogen; and
$R^5$ represents a substituted or unsubstituted $C_1$-$C_6$-alkyl group.

WO 2011/063908 A1 discloses compounds of formula S3:

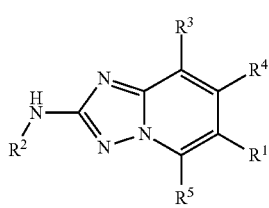

in which
$R^1$ is an aryl group which is substituted at least one time; whereas the at least one substituent inter alia can be —N(H)C(=O)$R^6$ or —C(=O)N(H)$R^6$; in which $R^6$ inter alia represents a group selected from $C_3$-$C_6$-cycloalkyl, 3- to 10-membered heterocyclyl-, aryl-, heteroaryl-, —(CH$_2$)$_q$—(C$_3$-C$_6$-cycloalkyl), —(CH$_2$)$_q$— (3- to 10-membered heterocyclyl), —(CH$_2$)$_q$-aryl, and —(CH$_2$)$_q$-heteroaryl, wherein $R^6$ is optionally substituted, and q is 0, 1, 2 or 3;
$R^2$ represents a substituted or unsubstituted aryl- or heteroaryl- group;
$R^3$ and $R^4$ inter alia can be hydrogen; and
$R^5$ is hydrogen.

There are patent applications which are related to [1,2,4]-triazolo-[1,5-a]-pyridines and their use for inhibition of Mps-1 kinase, but which have not been published at the time of filing of this patent application: Subject matter of the EP patent applications No. 11167872.8, and No. 11167139.2 as well as of the patent application PCT/EP2011/059806 are compounds of formula S4:

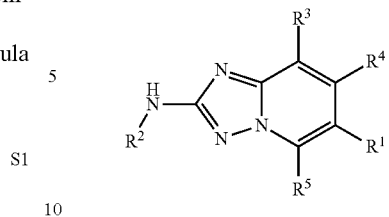

in which
$R^1$ represents inter alia a phenyl- group which is substituted at least one time; whereas the at least one substituent inter alia can be —N(H)C(=O)$R^6$; in which $R^6$ inter alia can be —(CH$_2$)$_q$-aryl, wherein $R^6$ is optionally substituted, and q is 0, 1, 2 or 3;
$R^2$ represents a substituted or unsubstituted aryl- or heteroaryl- group;
$R^3$ and $R^4$ inter alia can be hydrogen; and
$R^5$ is hydrogen.

However, the state of the art described above does not specifically disclose the substituted triazolopyridine compounds of general formula (I) of the present invention, or a tautomer, an N-oxide, a hydrate, a solvate, or a salt thereof, or a mixture of same, as described and defined herein, and as hereinafter referred to as "compounds of the present invention", or their pharmacological activity.

The above mentioned patent applications which are related to [1,2,4]-triazolo-[1,5-a]-pyridines mainly focus on the effectiveness of the compounds in inhibiting Mps-1 kinase, expressed by the half maximal inhibitory concentration (IC$_{50}$) of the compounds.

For example, in WO 2011/063908 A1 the effectiveness in inhibiting Mps-1 kinase was measured in an Mps-1 kinase assay with a concentration of 10 μM adenosine triphosphate (ATP).

The cellular concentration of ATP in mammals is in the millimolar range. Therefore it is important that a drug substance is also effective in inhibiting Mps-1 kinase in a kinase assay with a concentration of ATP in the millimolar range, e.g. 2 mM ATP, in order to potentially achieve an antiproliferative effect in a cellular assay.

In addition, as one of ordinary skill in the art knows, there a many more factors determining the druglikeness of a compound. The objective of a pre-clinical development is to assess e.g. safety, toxicity, pharmacokinetics and metabolism parameters prior to human clinical trials.

One important factor for assessing the druglikeness of a compound is the metabolic stability. The metabolic stability of a compound can be determined e.g. by incubating the compound with a suspension of liver microsomes from e.g. a rat, a dog and/or a human (for details see experimental section).

Another important factor for assessing the druglikeness of a compound for the treatment of cancer is the inhibition of cell proliferation which can be determined e.g. in a HeLa cell proliferation assay (for details see experimental section).

Surprisingly it was found, that the compounds of the present invention are characterized by:
  an IC$_{50}$ lower than or equal to 1 nM (more potent than 1 nM) in an Mps-1 kinase assay with a concentration of 10 μM ATP, and
  an IC$_{50}$ lower than 10 nM (more potent than 10 nM) in an Mps-1 kinase assay with a concentration of 2 mM ATP, and a maximum oral bioavailability ($F_{max}$) in rat that is higher than 50% determined by means of rat liver microsomes as described below, and a maximum oral bioavailability ($F_{max}$) in dog that is higher than 45% determined by means of dog liver microsomes as described below, and a maximum oral bioavailability ($F_{max}$) in human that is higher than 45%, determined by means of human liver microsomes as described below, and an $IC_{50}$ lower than 600 nM in a HeLa cell proliferation assay as described below.

Hence, the compounds of the present invention have surprising and advantageous properties. These unexpected findings give rise to the present selection invention. The compounds of the present invention are purposively selected from the above mentioned prior art due to their superior properties.

In particular, said compounds of the present invention may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1 kinase, such as, for example, haemotological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

SUMMARY OF THE INVENTION

The present invention covers compounds of general formula (I):

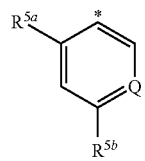

(I)

in which:
$R^1$ represents

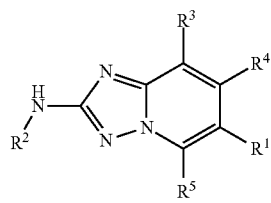

wherein * indicates the point of attachment of said group with the rest of the molecule;

$R^2$ represents

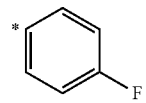

wherein * indicates the point of attachment of said group with the rest of the molecule;

$R^3$ represents a hydrogen atom;

$R^4$ represents a hydrogen atom;

$R^5$ represents a hydrogen atom or a $C_1$-$C_3$-alkyl- group;

$R^{5a}$ represents a group selected from: $C_1$-$C_4$-alkoxy-, halo-$C_1$-$C_4$-alkoxy-, $C_1$-$C_4$-alkyl;

$R^{5b}$ represents a group selected from:
—C(=O)N(H)R$^8$, —C(=O)NR$^8$R$^7$, —N(R$^7$)C(=O)OR$^8$, R$^7$—S(=O)$_2$—;

$R^6$ represents a

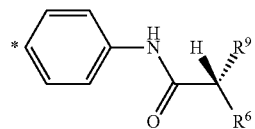

group;

wherein * indicates the point of attachment of said group with the rest of the molecule;

wherein said group is optionally substituted, one or more times, identically or differently, with a halogen atom or a methyl- group;

$R^7$ represents a $C_1$-$C_3$-alkyl- or a cyclopropyl- group;

$R^8$ represents a hydrogen atom or a $C_1$-$C_6$-alkyl- or $C_3$-$C_6$-cycloalkyl- group; wherein said $C_1$-$C_6$-alkyl- or $C_3$-$C_6$-cycloalkyl- group is optionally substituted, one or more times, with a halogen atom;

or $R^7$ and $R^8$ together with the molecular fragment they are attached to represent a 4- to 6-membered heterocyclic ring, which is optionally substituted, one or more times, identically or differently, with a halogen atom, a $C_1$-$C_3$-alkyl-, halo-$C_1$-$C_3$-alkyl- or $C_1$-$C_3$-alkoxy- group;

$R^9$ represents a group selected from: $C_1$-$C_3$-alkyl-, hydroxy-$C_1$-$C_3$-alkyl-, —N(H)R$^8$; —N(R$^7$)R$^8$, N(H)(R$^8$)—$C_1$-$C_3$-alkyl-, N(R$^7$)(R$^8$)—$C_1$-$C_3$-alkyl-;

and

Q represents CH or N;

or a tautomer, an N-oxide, a hydrate, a solvate, or a salt thereof, or a mixture of same.

The present invention further relates to methods of preparing compounds of general formula (I), to pharmaceutical compositions and combinations comprising said compounds, to the use of said compounds for manufacturing a pharmaceutical composition for the treatment or prophylaxis of a disease, as well as to intermediate compounds useful in the preparation of said compounds.

DETAILED DESCRIPTION OF THE INVENTION

The terms as mentioned in the present text have preferably the following meanings:

The term "halogen atom" or "halo-" is to be understood as meaning a fluorine, chlorine, bromine or iodine atom.

The term "$C_1$-$C_6$-alkyl" is to be understood as preferably meaning a linear or branched, saturated, monovalent hydrocarbon group having 1, 2, 3, 4, 5 or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.

The term "halo-$C_1$-$C_6$-alkyl" is to be understood as preferably meaning a linear or branched, saturated, monovalent hydrocarbon group in which the term "$C_1$-$C_6$-alkyl" is defined supra, and in which one or more of the hydrogen atoms is replaced, in identically or differently, by a halogen atom. Particularly, said halogen atom is F. Said halo-$C_1$-$C_6$-alkyl group is, for example, —$CF_3$, —$CHF_2$, —$CH_2F$, —$CF_2CF_3$, or —$CH_2CF_3$.

The term "$C_1$-$C_6$-alkoxy" is to be understood as preferably meaning a linear or branched, saturated, monovalent group of formula —O—($C_1$-$C_6$-alkyl), in which the term "$C_1$-$C_6$-alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "halo-$C_1$-$C_6$-alkoxy" is to be understood as preferably meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said halo-$C_1$-$C_6$-alkoxy group is, for example, —$OCF_3$, —$OCHF_2$, —$OCH_2F$, —$OCF_2CF_3$, or —$OCH_2CF_3$.

The term "$C_1$-$C_6$-alkoxy-$C_1$-$C_6$-alkyl" is to be understood as preferably meaning a linear or branched, saturated, monovalent $C_1$-$C_6$-alkyl group, as defined supra, in which one or more of the hydrogen atoms is replaced, in identically or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, or an isomer thereof.

The term "halo-$C_1$-$C_6$-alkoxy-$C_1$-$C_6$-alkyl" is to be understood as preferably meaning a linear or branched, saturated, monovalent $C_1$-$C_6$-alkoxy-$C_1$-$C_6$-alkyl group, as defined supra, in which one or more of the hydrogen atoms is replaced, in identically or differently, by a halogen atom. Particularly, said halogen atom is F. Said halo-$C_1$-$C_6$-alkoxy-$C_1$-$C_6$-alkyl group is, for example, —$CH_2CH_2OCF_3$, —$CH_2CH_2OCHF_2$, —$CH_2CH_2OCH_2F$, —$CH_2CH_2OCF_2CF_3$, or —$CH_2CH_2OCH_2CF_3$.

The term "$C_2$-$C_6$-alkenyl" is to be understood as preferably meaning a linear or branched, monovalent hydrocarbon group, which contains one or more double bonds, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (2)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl) ethenyl, buta-1,3-dienyl, penta-1,4-dienyl, hexa-1,5-dienyl, or methylhexadienyl group. Particularly, said group is vinyl or allyl.

The term "$C_2$-$C_6$-alkynyl" is to be understood as preferably meaning a linear or branched, monovalent hydrocarbon group which contains one or more triple bonds, and which contains 2, 3, 4, 5 or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-inyl, hex-3-inyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-inyl, 1,1-dimethylbut-3-ynyl, 1,1-dimethylbut-2-ynyl, or 3,3-dimethyl-but-1-ynyl group. Particularly, said alkynyl group is ethynyl, prop-1-ynyl, or prop-2-inyl.

The term "$C_3$-$C_6$-cycloalkyl" is to be understood as preferably meaning a saturated, monovalent, mono-, or bicyclic hydrocarbon ring which contains 3, 4, 5 or 6 carbon atoms. Said $C_3$-$C_6$-cycloalkyl group is for example, a monocyclic hydrocarbon ring, e.g. a cyclopropyl, cyclobutyl, cyclopentyl, or cyclohexyl or a bicyclic hydrocarbon ring. Said cycloalkyl ring can optionally contain one or more double bonds e.g. cycloalkenyl, such as a cyclopropenyl, cyclobutenyl, cyclopentenyl or cyclohexenyl group, wherein the bond between said ring with the rest of the molecule may be to any carbon atom of said ring, be it saturated or unsaturated.

The term "heterocyclic ring", as used in the term "4-, 5- or 6-membered heterocyclic ring", or "4- to 6-membered heterocyclic ring" or "4- to 5-membered heterocyclic ring", for example, as used in the definition of compounds of general formula (I) as defined herein, is to be understood as meaning a saturated or partially unsaturated, monocyclic nitrogen atom-containing ring, said nitrogen atom being the point of attachment of said heterocyclic ring with the rest of the molecule. Said nitrogen atom-containing ring optionally further contains 1 or 2 heteroatom-containing groups selected from 0 and C(=O). Particularly, without being limited thereto, said nitrogen atom-containing ring can be a 4-membered ring, such as an azetidinyl ring, for example, or a 5-membered ring, such as a pyrrolidinyl ring or oxazolidinonyl ring, for example, or a 6-membered ring, such as a piperidinyl or morpholinyl ring, for example; it being reiterated that any of the above-mentioned nitrogen atom-containing rings can further contain 1 or 2 heteroatom-containing groups selected from 0 and C(=O).

As mentioned supra, said nitrogen atom-containing ring can be partially unsaturated, i.e. it can contain one or more double bonds, such as, without being limited thereto, a 2,5-dihydro-1H-pyrrolyl ring, for example.

The term "3- to 10-membered heterocycloalkyl" is to be understood as preferably meaning a saturated or partially unsaturated, monovalent, mono- or bicyclic hydrocarbon ring which contains 2, 3, 4, 5, 6, 7, 8, or 9 carbon atoms, and one or more heteroatom-containing groups selected from C(=O), O, S, S(=O), S(=O)$_2$, NH, NR'', wherein R'' represents a $C_1$-$C_6$-alkyl, $C_3$-$C_6$-cycloalkyl, —C(=O)—($C_1$-$C_6$-alkyl) or —C(=O)—($C_1$-$C_6$-cycloalkyl). Particularly, said ring can contain 2, 3, 4, or 5 carbon atoms, and one or more of the above-mentioned heteroatom-containing groups (a "3- to 6-membered heterocycloalkyl"), more particularly said ring can contain 4 or 5 carbon atoms, and one or more of the above-mentioned heteroatom-containing groups (a "5- to 6-membered heterocycloalkyl"). Said heterocycloalkyl ring is for example, a monocyclic heterocycloalkyl ring such as an oxyranyl, oxetanyl, aziridinyl, azetidinyl, tetrahydrofuranyl, pyrrolidinyl, imidazolidinyl, pyrazolidinyl, pyrrolinyl, tetrahydropyranyl, piperidinyl, morpholinyl, dithianyl, thiomorpholinyl, piperazinyl, trithianyl, or chinuclidinyl group. Optionally, said heterocycloalkyl ring can contain one or more double bonds, e.g. 4H-pyranyl, 2H-pyranyl, 3H-diazirinyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydro-1,3-oxazolyl, 4,4-dimethyl-4,5-dihydro-1,3-oxazolyl, or 4H-[1,4]thiazinyl group, or, it may be benzo fused.

The term "aryl" is to be understood as preferably meaning a monovalent, aromatic or partially aromatic, mono-, or bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group, or a biphenyl group, or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a ring having 13 carbon atoms, (a "$C_{13}$-aryl" group), e.g. a fluorenyl group, or a ring having 14 carbon atoms, (a "$C_{14}$-aryl" group), e.g. an anthranyl group.

The term "heteroaryl" is understood as preferably meaning a monovalent, aromatic, mono- or bicyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and can be monocyclic, bicyclic, or tricyclic, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc. More particularly, heteroaryl is selected from pyridyl, benzofuranyl, benzisoxazolyl, indazolyl, quinazolinyl, thienyl, quinolinyl, benzothienyl, pyrazolyl, or furanyl.

The term "alkylene" is understood as preferably meaning an optionally substituted hydrocarbon chain (or "tether") having 1, 2, 3, 4, 5, 6, 7 or 8 carbon atoms, i.e. an optionally substituted —CH$_2$— ("methylene" or "single membered tether" or, for example —C(CH$_3$)$_2$—), —CH$_2$—CH$_2$— ("ethylene", "dimethylene", or "two-membered tether", for example —C(CH$_3$)$_2$—C(CH$_3$)$_2$—), —CH$_2$—CH$_2$—CH$_2$— ("propylene", "trimethylene", or "three-membered tether", for example CH$_2$—C(H)(CH$_3$)—CH$_2$—, —CH$_2$—C(CH$_3$)$_2$—CH$_2$—), —CH$_2$—CH$_2$—CH$_2$—CH$_2$— ("butylene", "tetramethylene", or "four-membered tether"), —CH$_2$—CH$_2$—CH$_2$—CH$_2$—CH$_2$— ("pentylene", "pentamethylene" or "five-membered ether"), or —CH$_2$—CH$_2$—CH$_2$—CH$_2$—CH$_2$—CH$_2$— ("hexylene", "hexamethylene", or six-membered tether") group. Particularly, said alkylene tether has 1, 2, 3, 4, or 5 carbon atoms, more particularly 1 or 2 carbon atoms.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_5$, $C_1$-$C_6$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

As used herein, the term "PG$^1$" refers to a protecting group for hydroxy groups e.g. a TMS group or TBDPS group as described for example in T. W. Greene and P. G. M. Wuts in *Protective Groups in Organic Synthesis*, 3$^{rd}$ edition, Wiley 1999 (TMS=trimethylsilyl, TBDPS=tert-butyldiphenylsilyl).

As used herein, the term "PG$^2$" refers to a protecting group for amino groups e.g. a Boc group as described for example in T. W. Greene and P. G. M. Wuts in *Protective Groups in Organic Synthesis*, 3$^{rd}$ edition, Wiley 1999 (Boc=ten-butyloxycarbonyl).

As used herein, the term "one or more times", e.g. in the definition of the substituents of the compounds of the general formulae of the present invention, is understood as meaning "one, two, three, four or five times, particularly one, two, three or four times, more particularly one, two or three times, even more particularly one or two times".

Where the plural form of the word compounds, salts, polymorphs, hydrates, solvates and the like, is used herein, this is taken to mean also a single compound, salt, polymorph, isomer, hydrate, solvate or the like.

The compounds of this invention contain one or more asymmetric centre, depending upon the location and nature of the various substituents desired. Asymmetric carbon atoms may be present in the (R) or (S) configuration. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Diacel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$I, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

The present invention includes all possible stereoisomers of the compounds of the present invention as single stereoisomers, or as any mixture of said stereoisomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, viz.:

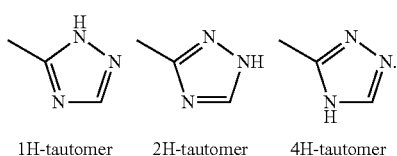

1H-tautomer    2H-tautomer    4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta-etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethanesulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol.

Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_5$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorphs, or as a mixture of more than one polymorphs, in any ratio.

In accordance with a first aspect, the present invention covers compounds of general formula (I):

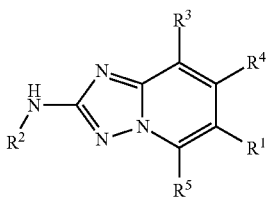
(I)

in which:

R¹ represents

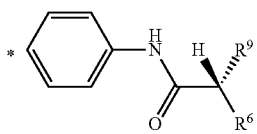

wherein * indicates the point of attachment of said group with the rest of the molecule;

R² represents

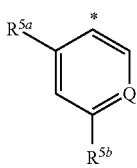

wherein * indicates the point of attachment of said group with the rest of the molecule;
R³ represents a hydrogen atom;
R⁴ represents a hydrogen atom;
R⁵ represents a hydrogen atom or a $C_1$-$C_3$-alkyl- group;
$R^{5a}$ represents a group selected from: $C_1$-$C_4$-alkoxy-, halo-$C_1$-$C_4$-alkoxy-, $C_1$-$C_4$-alkyl;
$R^{5b}$ represents a group selected from:
—C(=O)N(H)R⁸, —C(=O)NR⁸R⁷, —N(R⁴)C(=O)OR⁸, R⁷—S(=O)₂—;
R⁶ represents a

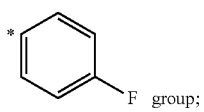

wherein * indicates the point of attachment of said group with the rest of the molecule;
wherein said group is optionally substituted, one or more times, identically or differently, with a halogen atom or a methyl- group;
R⁷ represents a $C_1$-$C_3$-alkyl- or a cyclopropyl- group;
R⁸ represents a hydrogen atom or a $C_1$-$C_6$-alkyl- or $C_3$-$C_6$-cycloalkyl- group;
wherein said $C_1$-$C_6$-alkyl- or $C_3$-$C_6$-cycloalkyl- group is optionally substituted, one or more times, with a halogen atom;
or
R⁷ and R⁸ together with the molecular fragment they are attached to represent a 4- to 6-membered heterocyclic ring, which is optionally substituted, one or more times, identically or differently, with a halogen atom, a $C_1$-$C_3$-alkyl-, halo-$C_1$-$C_3$-alkyl- or $C_1$-$C_3$-alkoxy- group;

R⁹ represents a group selected from: $C_1$-$C_3$-alkyl-, hydroxy-$C_1$-$C_3$-alkyl-, —N(H)R⁸; —N(R⁷)R⁸, N(H)(R⁸)—$C_1$-$C_3$-alkyl-, N(R⁷)(R⁸)—$C_1$-$C_3$-alkyl-;

and

Q represents CH or N;

or a tautomer, an N-oxide, a hydrate, a solvate, or a salt thereof, or a mixture of same.

In a preferred embodiment, the invention relates to compounds of formula (I), supra, wherein R¹ represents a group selected from:

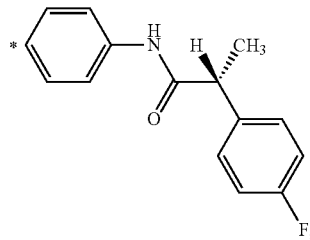

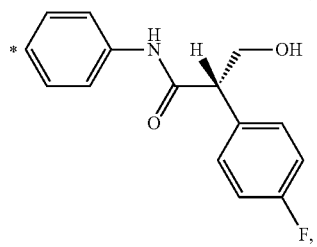

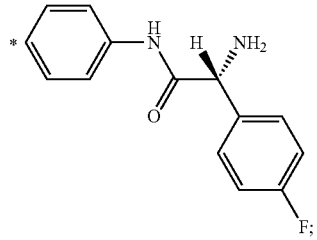

wherein * indicates the point of attachment of said groups with the rest of the molecule.

In another preferred embodiment, the invention relates to compounds of formula (I), supra, wherein R¹ represents

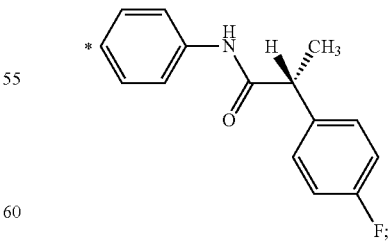

wherein * indicates the point of attachment of said groups with the rest of the molecule.

In another preferred embodiment, the invention relates to compounds of formula (I), supra, wherein R¹ represents

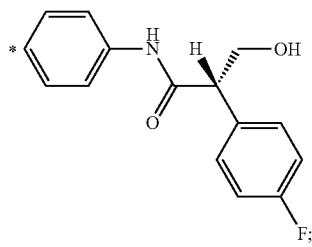

wherein * indicates the point of attachment of said groups with the rest of the molecule.

In another preferred embodiment, the invention relates to compounds of formula (I), supra, wherein $R^1$ represents

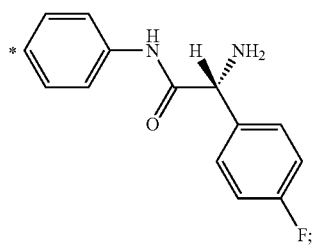

wherein * indicates the point of attachment of said groups with the rest of the molecule.

In another preferred embodiment, the invention relates to compounds of formula (I), wherein $R^2$ represents

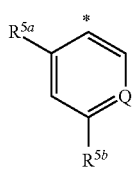

wherein * indicates the point of attachment of said groups with the rest of the molecule and wherein $R^{5a}$ represents methoxy-. Q preferably represents CH.

In another preferred embodiment, the invention relates to compounds of formula (I), wherein $R^2$ represents

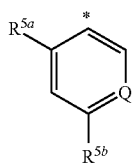

wherein * indicates the point of attachment of said groups with the rest of the molecule and wherein $R^{5a}$ represents $F_3C$—$CH_2$—O—. Q preferably represents CH.

In another preferred embodiment, the invention relates to compounds of formula (I), supra, wherein $R^2$ represents a group selected from:

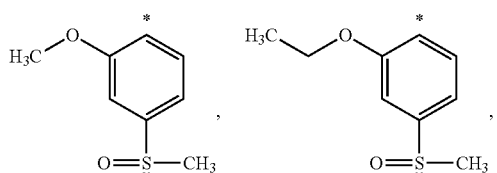

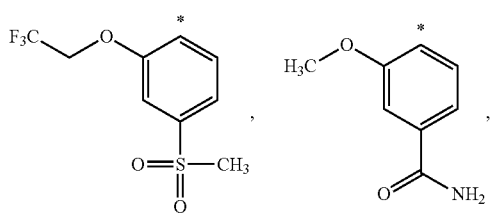

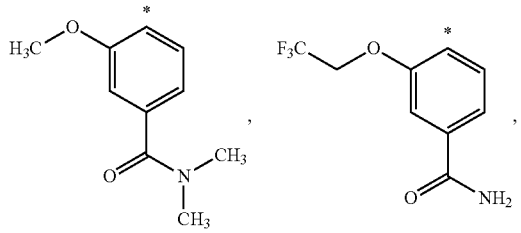

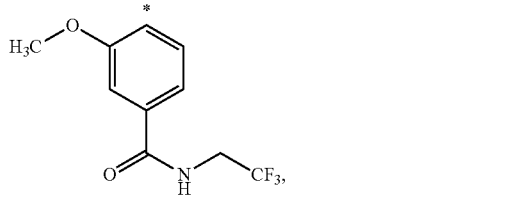

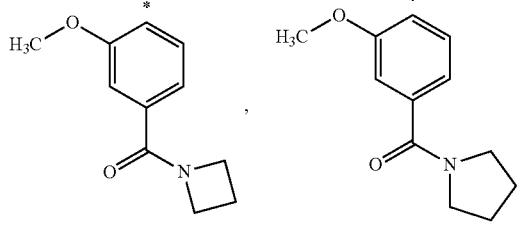

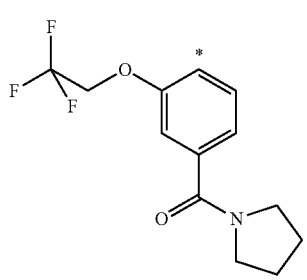

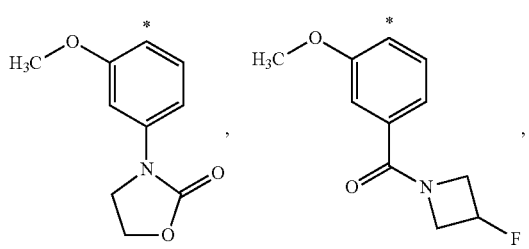

-continued

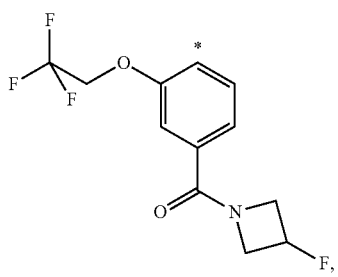

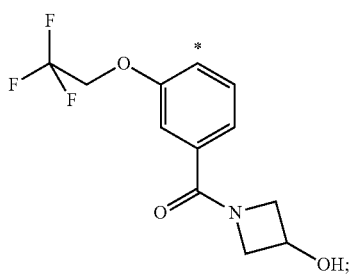

wherein * indicates the point of attachment of said groups with the rest of the molecule.

In another preferred embodiment, the invention relates to compounds of formula (I), supra, wherein R² represents

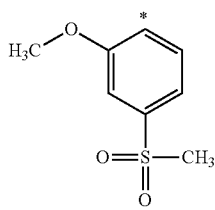

wherein * indicates the point of attachment of said groups with the rest of the molecule.

In another preferred embodiment, the invention relates to compounds of formula (I), supra, wherein R² represents

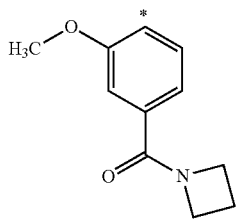

wherein * indicates the point of attachment of said groups with the rest of the molecule.

In another preferred embodiment, the invention relates to compounds of formula (I), supra, wherein R² represents

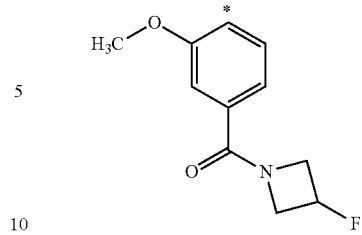

wherein * indicates the point of attachment of said groups with the rest of the molecule.

In another preferred embodiment, the invention relates to compounds of formula (I), supra, wherein R² represents

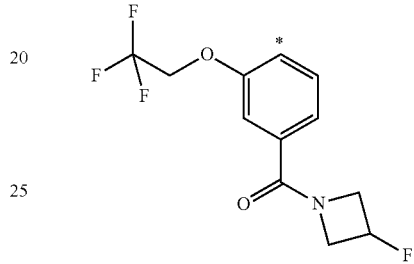

wherein * indicates the point of attachment of said groups with the rest of the molecule.

In another preferred embodiment, the invention relates to compounds of formula (I), supra, wherein R² represents

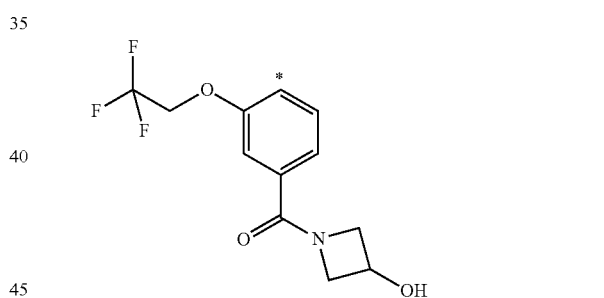

wherein * indicates the point of attachment of said groups with the rest of the molecule.

In another preferred embodiment, the invention relates to compounds of formula (I), supra, wherein R² represents

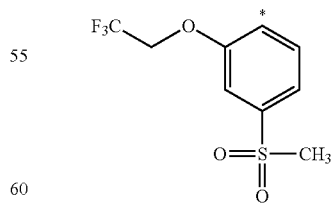

wherein * indicates the point of attachment of said groups with the rest of the molecule.

In another preferred embodiment, the invention relates to compounds of formula (I), supra, wherein R⁵ represents a hydrogen atom or a methyl- group.

In another preferred embodiment, the invention relates to compounds of formula (I), supra, wherein $R^5$ represents a hydrogen atom.

In another preferred embodiment, the invention relates to compounds of formula (I), supra, wherein $R^{5a}$ represents a group selected from: $C_1$-$C_3$-alkoxy-, halo-$C_1$-$C_3$-alkoxy-, $C_1$-$C_3$-alkyl-.

In another preferred embodiment, the invention relates to compounds of formula (I), supra, wherein $R^{5a}$ represents a group selected from: $C_1$-$C_2$-alkoxy-, halo-$C_1$-$C_2$-alkoxy-, $C_1$-$C_2$-alkyl-.

In another preferred embodiment, the invention relates to compounds of formula (I), supra, wherein $R^{5a}$ represents a group selected from: $C_1$-$C_3$-alkoxy-, halo-$C_1$-$C_3$-alkoxy-.

In another preferred embodiment, the invention relates to compounds of formula (I), supra, wherein $R^{5a}$ represents a group selected from: $C_1$-$C_2$-alkoxy-, halo-$C_1$-$C_2$-alkoxy-.

In another preferred embodiment, the invention relates to compounds of formula (I), supra, wherein $R^{5a}$ represents a methoxy- or ethoxy- group which is optionally substituted, one or more times, identically or differently, with a halogen atom. The preferred halogen atom is F.

In another preferred embodiment, the invention relates to compounds of formula (I), supra, wherein $R^{5a}$ represents a group selected from: methoxy-, ethoxy-, $F_3C$—$CH_2$—O—.

In another preferred embodiment, the invention relates to compounds of formula (I), supra, wherein $R^{5a}$ represents a group selected from: methoxy-, $F_3C$—$CH_2$—O—.

In another preferred embodiment, the invention relates to compounds of formula (I), supra, wherein $R^{5a}$ represents methoxy-.

In another preferred embodiment, the invention relates to compounds of formula (I), supra, wherein $R^{5a}$ represents $F_3C$—$CH_2$—O—.

In another preferred embodiment, the invention relates to compounds of formula (I), supra, wherein $R^{5b}$ represents $R^7$—$S(=O)_2$—; in which $R^7$ represents a $C_1$-$C_3$-alkyl- group.

In another preferred embodiment, the invention relates to compounds of formula (I), supra, wherein $R^{5b}$ represents a $R^7$—$S(=O)_2$— group; in which $R^7$ represents a methyl- group.

In another preferred embodiment, the invention relates to compounds of formula (I), supra, wherein $R^{5b}$ represents —C(=O)N(H)R^8$; in which $R^8$ represents a hydrogen atom or a $C_1$-$C_3$-alkyl- or $C_3$-$C_6$-cycloalkyl- group, wherein said $C_1$-$C_3$-alkyl- or $C_3$-$C_6$-cycloalkyl- group is optionally substituted, one or more times, with a halogen atom. The preferred halogen atom is F.

In another preferred embodiment, the invention relates to compounds of formula (I), supra, wherein $R^{5b}$ represents —C(=O)N(H)R^8$; in which $R^8$ represents a hydrogen atom or a $C_1$-$C_3$-alkyl- group, wherein said $C_1$-$C_3$-alkyl- group is optionally substituted, one or more times, with a halogen atom. The preferred halogen atom is F.

In another preferred embodiment, the invention relates to compounds of formula (I), supra, wherein $R^{5b}$ represents —C(=O)N(H)R^8$; in which $R^8$ represents a group selected from: —$CH_3$, —$CF_3$, —$C_2H_5$, —$CH_2CF_3$.

In another preferred embodiment, the invention relates to compounds of formula (I), supra, wherein $R^{5b}$ represents —C(=O)NR^8R^7$; in which $R^7$ and $R^8$ together with the N atom they are attached to represent a 4- to 6-membered heterocyclic ring, which is optionally substituted, one or more times, identically or differently, with a halogen atom, a $C_1$-$C_3$-alkyl- or a halo-$C_1$-$C_3$-alkyl- group.

In another preferred embodiment, the invention relates to compounds of formula (I), supra, wherein $R^{5b}$ represents —C(=O)NR^8R^7$; in which $R^7$ and $R^8$ together with the N atom they are attached to represent a 4-membered heterocyclic ring, which is optionally substituted, one or more times, identically or differently, with a halogen atom, a $C_1$-$C_3$-alkyl- or a halo-$C_1$-$C_3$-alkyl- group.

In another preferred embodiment, the invention relates to compounds of formula (I), supra, wherein $R^{5b}$ represents —C(=O)NR^8R^7$; in which $R^7$ and $R^8$ together with the N atom they are attached to represent a 4- to 6-membered heterocyclic ring, which is optionally substituted, one or more times, identically or differently, with a halogen atom.

In another preferred embodiment, the invention relates to compounds of formula (I), supra, wherein $R^{5b}$ represents —C(=O)NR^8R^7$; in which $R^7$ and $R^8$ together with the N atom they are attached to represent a 4-membered heterocyclic ring, which is optionally substituted, one or more times, with a fluorine atom.

In another preferred embodiment, the invention relates to compounds of formula (I), supra, wherein $R^{5b}$ represents —N(R^7)C(=O)OR^8$; in which $R^7$ and $R^8$ together with the molecular fragment they are attached to represent a 4- to 6-membered heterocyclic ring, which is optionally substituted, one or more times, identically or differently, with a halogen atom, a $C_1$-$C_3$-alkyl- or a halo-$C_1$-$C_3$-alkyl- group.

In another preferred embodiment, the invention relates to compounds of formula (I), supra, wherein $R^{5b}$ represents —N(R^7)C(=O)OR^8$; in which $R^7$ and $R^8$ together with the molecular fragment they are attached to represent a 5-membered heterocyclic ring, which is optionally substituted, one or more times, identically or differently, with a halogen atom, a $C_1$-$C_3$-alkyl- or a halo-$C_1$-$C_3$-alkyl- group.

In another preferred embodiment, the invention relates to compounds of formula (I), supra, wherein $R^{5b}$ represents —N(R^7)C(=O)OR^8$; in which $R^7$ and $R^8$ together with the molecular fragment they are attached to represent a 5-membered heterocyclic ring.

In another preferred embodiment, the invention relates to compounds of formula (I), supra, wherein $R^{5b}$ is selected from:

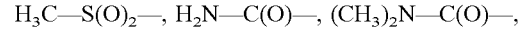

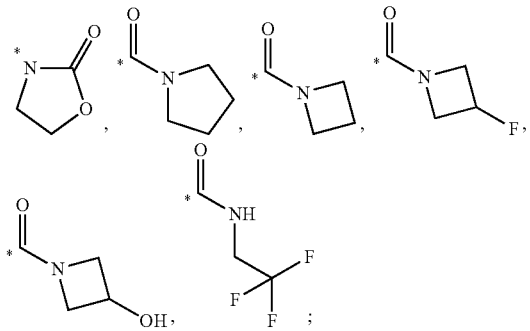

wherein * indicates the point of attachment of said groups with the rest of the molecule.

In another preferred embodiment, the invention relates to compounds of formula (I), supra, wherein $R^{5b}$ represents $H_3C$—$S(O)_2$—.

In another preferred embodiment, the invention relates to compounds of formula (I), supra, wherein $R^{5b}$ represents

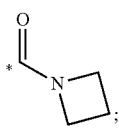

wherein * indicates the point of attachment of said groups with the rest of the molecule.

In another preferred embodiment, the invention relates to compounds of formula (I), supra, wherein $R^{5b}$ represents

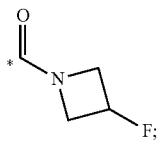

wherein * indicates the point of attachment of said groups with the rest of the molecule.

In another preferred embodiment, the invention relates to compounds of formula (I), supra, wherein $R^{5b}$ represents

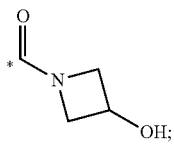

wherein * indicates the point of attachment of said groups with the rest of the molecule.

In another preferred embodiment, the invention relates to compounds of formula (I), supra, wherein $R^{5b}$ represents

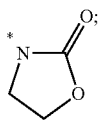

wherein * indicates the point of attachment of said groups with the rest of the molecule.

In another preferred embodiment, the invention relates to compounds of formula (I), supra, wherein $R^6$ represents a

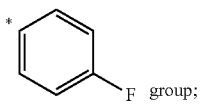

wherein * indicates the point of attachment of said group with the rest of the molecule.

In another preferred embodiment, the invention relates to compounds of formula (I), supra, wherein $R^7$ represents a $C_1$-$C_3$-alkyl- group.

In another preferred embodiment, the invention relates to compounds of formula (I), supra, wherein $R^7$ represents a methyl- group.

In another preferred embodiment, the invention relates to compounds of formula (I), supra, wherein $R^8$ represents a hydrogen atom or a $C_1$-$C_6$-alkyl-group, wherein said $C_1$-$C_6$-alkyl- group is optionally substituted, one or more times, with a halogen atom.

In another preferred embodiment, the invention relates to compounds of formula (I), supra, wherein $R^8$ represents a hydrogen atom or a $C_1$-$C_3$-alkyl-group, wherein said $C_1$-$C_3$-alkyl- group is optionally substituted, one or more times, with a halogen atom.

In another preferred embodiment, the invention relates to compounds of formula (I), supra, wherein $R^9$ represents a group selected from: $C_1$-$C_3$-alkyl-, hydroxy-$C_1$-$C_3$-alkyl-, —N(H)$R^8$, N(H)($R^8$)—$C_1$-$C_3$-alkyl-.

In another preferred embodiment, the invention relates to compounds of formula (I), supra, wherein $R^9$ represents a group selected from: $C_1$-$C_3$-alkyl-, hydroxy-$C_1$-$C_3$-alkyl-, —N($R^{10}$)$R^{10}$, —$C_1$-$C_2$-alkyl-N($R^{10}$)$R^{10}$; in which $R^{10}$ represents a hydrogen atom or a methyl- group.

In another preferred embodiment, the invention relates to compounds of formula (I), supra, wherein $R^9$ represents a group selected from: methyl-, hydroxy-$C_1$-$C_2$-alkyl-, —N($R^{10}$)$R^{10}$, —$C_1$-$C_2$-alkyl-N($R^{10}$)$R^{10}$; in which $R^{10}$ represents a hydrogen atom or a methyl- group.

In another preferred embodiment, the invention relates to compounds of formula (I), supra, wherein $R^9$ represents a group selected from: methyl-, HO—$CH_2$—, $H_2N$—$CH_2$—, —$NH_2$.

In another preferred embodiment, the invention relates to compounds of formula (I), supra, wherein $R^9$ represents a group selected from: methyl-, HO—$CH_2$—, —$NH_2$.

In another preferred embodiment, the invention relates to compounds of formula (I), supra, wherein $R^9$ represents a methyl- group.

In another preferred embodiment, the invention relates to compounds of formula (I), supra, wherein $R^9$ represents a HO—$CH_2$— group.

In another preferred embodiment, the invention relates to compounds of formula (I), supra, wherein $R^9$ represents a —$NH_2$ group.

In another preferred embodiment, the invention relates to compounds of formula (I), supra, wherein Q represents CH.

As one of ordinary skill in the art knows, the molecular weight of a compound very often has an influence on the bioavailability; see e.g. Lipinski's *Rule of five* (Lipinski, C. A.; Lombardo, F.; Dominy, B. W.; Feeney, P. J.; Adv. Drug Deliver. Rev. 1997, 23, 3). As experimentally proven there is no clear cutoff at a molecular weight of 500 separating compounds with poor bioavailability from those with acceptable values—however, it is proven that higher bioavailability is indeed associated with lower molecular weight (see e.g. Veber et al., J. Med. Chem. 2002, 45, 2615-2623). In a preferred embodiment, therefore the invention relates to compounds of formula (I), supra, wherein the molecular weight is less than 655. In another preferred embodiment, the molecular weight of the compound of formula (I), supra, is less than 630, more preferably less than 600, most preferably less than 590.

It is to be understood that the present invention relates also to any combination of the preferred embodiments described above.

Some examples of combinations are given hereinafter. However, the invention is not limited to these combinations.

In a preferred embodiment, the invention relates to compounds of formula (I)

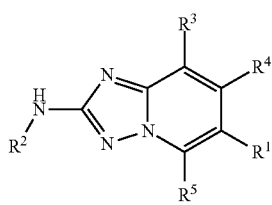
(I)

in which:
R¹ represents

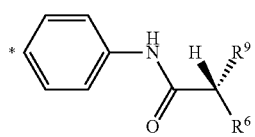

wherein * indicates the point of attachment of said group with the rest of the molecule;
R² represents

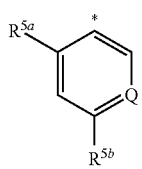

wherein * indicates the point of attachment of said group with the rest of the molecule;
R³ represents a hydrogen atom;
R⁴ represents a hydrogen atom;
R⁵ represents a hydrogen atom;
$R^{5a}$ represents a group selected from: $C_1$-$C_4$-alkoxy-, halo-$C_1$-$C_4$-alkoxy-, $C_1$-$C_4$-alkyl;
$R^{5b}$ represents a group selected from:
—C(=O)N(H)R⁸, —C(=O)NR⁸R⁷, —N(R⁷)C(=O)OR⁸, R⁷—S(=O)₂—;
R⁶ represents a

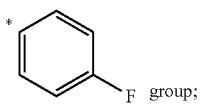

wherein * indicates the point of attachment of said group with the rest of the molecule;
wherein said group is optionally substituted, one or more times, identically or differently, with a halogen atom or a methyl- group;
R⁷ represents a $C_1$-$C_3$-alkyl- or a cyclopropyl- group;
R⁸ represents a hydrogen atom or a $C_1$-$C_6$-alkyl- or $C_3$-$C_6$-cycloalkyl- group; wherein said $C_1$-$C_6$-alkyl- or $C_3$-$C_6$-cycloalkyl- group is optionally substituted, one or more times, with a halogen atom;
or
R⁷ and R⁸ together with the molecular fragment they are attached to represent a 4- to 6-membered heterocyclic ring, which is optionally substituted, one or more times, identically or differently, with a halogen atom, a $C_1$-$C_3$-alkyl-, halo-$C_1$-$C_3$-alkyl- or $C_1$-$C_3$-alkoxy- group;

R⁹ represents a group selected from: $C_1$-$C_3$-alkyl-, hydroxy-$C_1$-$C_3$-alkyl-, —N(H)R⁸; —N(R⁷)R⁸, N(H)(R⁸)—$C_1$-$C_3$-alkyl-, N(R⁷)(R⁸)—$C_1$-$C_3$-alkyl-;
and
Q represents CH or N;
or a tautomer, an N-oxide, a hydrate, a solvate, or a salt thereof, or a mixture of same.

In another preferred embodiment, the invention relates to compounds of formula (I)

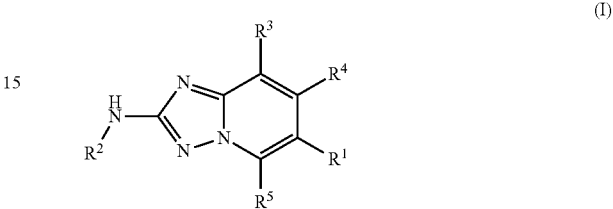
(I)

in which:
R¹ represents

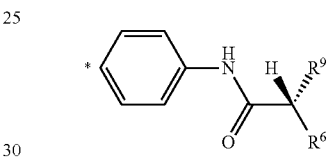

wherein * indicates the point of attachment of said group with the rest of the molecule;
R² represents

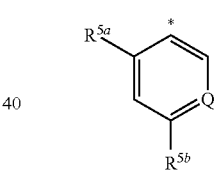

wherein * indicates the point of attachment of said group with the rest of the molecule;
R³ represents a hydrogen atom;
R⁴ represents a hydrogen atom;
R⁵ represents a hydrogen atom;
$R^{5a}$ represents a group selected from: $C_1$-$C_4$-alkoxy-, halo-$C_1$-$C_4$-alkoxy-, $C_1$-$C_4$-alkyl;
$R^{5b}$ represents a group selected from:
—C(=O)N(H)R⁸, —C(=O)NR⁸R⁷, —N(R⁷)C(=O)OR⁸, R⁷—S(=O)₂—;
R⁶ represents a

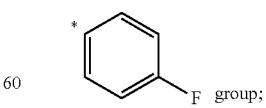

wherein * indicates the point of attachment of said group with the rest of the molecule;
wherein said group is optionally substituted, one or more times, identically or differently, with a halogen atom or a methyl- group;

$R^7$ represents a $C_1$-$C_3$-alkyl- or a cyclopropyl- group;
$R^8$ represents a hydrogen atom or a $C_1$-$C_6$-alkyl- or $C_3$-$C_6$-cycloalkyl- group, wherein said $C_1$-$C_6$-alkyl- or $C_3$-$C_6$-cycloalkyl- group is optionally substituted, one or more times, with a halogen atom;
or
$R^7$ and $R^8$ together with the molecular fragment they are attached to represent a 4- to 6-membered heterocyclic ring, which is optionally substituted, one or more times, identically or differently, with a halogen atom, a $C_1$-$C_3$-alkyl-, halo-$C_1$-$C_3$-alkyl- or $C_1$-$C_3$-alkoxy- group;
$R^9$ represents a group selected from: $C_1$-$C_3$-alkyl-, hydroxy-$C_1$-$C_3$-alkyl-, —N(H)$R^8$; —N($R^7$)$R^8$, N(H)($R^8$)—$C_1$-$C_3$-alkyl-, N($R^7$)($R^8$)—$C_1$-$C_3$-alkyl-;
and
Q represents CH;
or a tautomer, an N-oxide, a hydrate, a solvate, or a salt thereof, or a mixture of same.

In another preferred embodiment, the invention relates to compounds of formula (I)

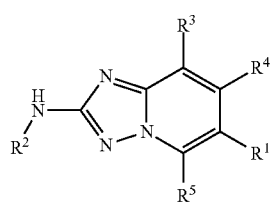
(I)

in which:
$R^1$ represents

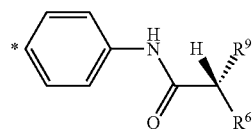

wherein * indicates the point of attachment of said group with the rest of the molecule;
$R^2$ represents

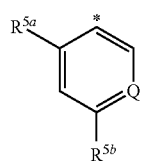

wherein * indicates the point of attachment of said group with the rest of the molecule;
$R^3$ represents a hydrogen atom;
$R^4$ represents a hydrogen atom;
$R^5$ represents a hydrogen atom;
$R^{5a}$ represents a group selected from: $C_1$-$C_2$-alkoxy-, halo-$C_1$-$C_2$-alkoxy-;
$R^{5b}$ represents a group selected from:
—C(=O)N(H)$R^8$, —C(=O)N$R^8R^7$, —N($R^7$)C(=O)O$R^8$, $R^7$—S(=O)$_2$—;

$R^6$ represents a

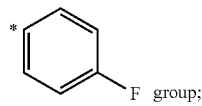
F group;

wherein * indicates the point of attachment of said group with the rest of the molecule;
wherein said group is optionally substituted, one or more times, identically or differently, with a halogen atom or a methyl- group;
$R^7$ represents a $C_1$-$C_3$-alkyl- or a cyclopropyl- group;
$R^8$ represents a hydrogen atom or a $C_1$-$C_6$-alkyl- or $C_3$-$C_6$-cycloalkyl- group, wherein said $C_1$-$C_6$-alkyl- or $C_3$-$C_6$-cycloalkyl- group is optionally substituted, one or more times, with a halogen atom;
or
$R^7$ and $R^8$ together with the molecular fragment they are attached to represent a 4- to 6-membered heterocyclic ring, which is optionally substituted, one or more times, identically or differently, with a halogen atom, a $C_1$-$C_3$-alkyl-, halo-$C_1$-$C_3$-alkyl- or $C_1$-$C_3$-alkoxy- group;
$R^9$ represents a group selected from: $C_1$-$C_3$-alkyl-, hydroxy-$C_1$-$C_3$-alkyl-, —N(H)$R^8$; —N($R^7$)$R^8$, N(H)($R^8$)—$C_1$-$C_3$-alkyl-, N($R^7$)($R^8$)—$C_1$-$C_3$-alkyl-;
and
Q represents CH;
or a tautomer, an N-oxide, a hydrate, a solvate, or a salt thereof, or a mixture of same.

In another preferred embodiment, the invention relates to compounds of formula (I)

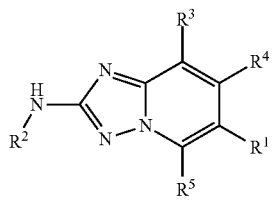
(I)

in which:
$R^1$ represents

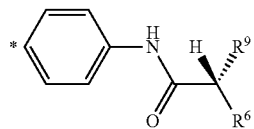

wherein * indicates the point of attachment of said group with the rest of the molecule;
$R^2$ represents

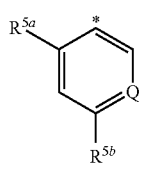

wherein * indicates the point of attachment of said group with the rest of the molecule;
R³ represents a hydrogen atom;
R⁴ represents a hydrogen atom;
R⁵ represents a hydrogen atom;
R⁵ᵃ represents a group selected from: $C_1$-$C_2$-alkoxy-, halo-$C_1$-$C_2$-alkoxy-;
R⁵ᵇ represents a group selected from:
—C(=O)N(H)R⁸, —C(=O)NR⁸R⁷, —N(R⁷)C(=O)OR⁸, R⁷—S(=O)₂—;
R⁶ represents a

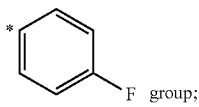
F group;

wherein * indicates the point of attachment of said group with the rest of the molecule;
R⁷ represents a $C_1$-$C_3$-alkyl- or a cyclopropyl- group;
R⁸ represents a hydrogen atom or a $C_1$-$C_6$-alkyl- or $C_3$-$C_6$-cycloalkyl- group, wherein said $C_1$-$C_6$-alkyl- or $C_3$-$C_6$-cycloalkyl- group is optionally substituted, one or more times, with a halogen atom;
or
R⁷ and R⁸ together with the molecular fragment they are attached to represent a 4- to 6-membered heterocyclic ring, which is optionally substituted, one or more times, identically or differently, with a halogen atom, a $C_1$-$C_3$-alkyl-, halo-$C_1$-$C_3$-alkyl- or $C_1$-$C_3$-alkoxy- group;
R⁹ represents a group selected from: $C_1$-$C_3$-alkyl-, hydroxy-$C_1$-$C_3$-alkyl-, —N(R¹⁰)R¹⁰, —$C_1$-$C_2$-alkyl-N(R¹⁰)R¹⁰;
R¹⁰ represents a hydrogen atom or a methyl- group;
and
Q represents CH;
or a tautomer, an N-oxide, a hydrate, a solvate, or a salt thereof, or a mixture of same.

In another preferred embodiment, the invention relates to compounds of formula (I)

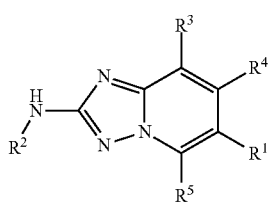

(I)

in which:
R¹ represents

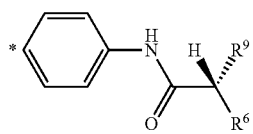

wherein * indicates the point of attachment of said group with the rest of the molecule;

R² represents

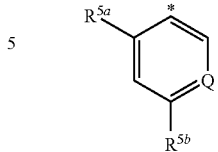

wherein * indicates the point of attachment of said group with the rest of the molecule;
R³ represents a hydrogen atom;
R⁴ represents a hydrogen atom;
R⁵ represents a hydrogen atom;
R⁵ᵃ represents a group selected from: $C_1$-$C_2$-alkoxy-, halo-$C_1$-$C_2$-alkoxy-;
R⁵ᵇ represents a group selected from:
—C(=O)N(H)R⁸, —C(=O)NR⁸R⁷, —N(R⁷)C(=O)OR⁸, R⁷—S(=O)₂—;
R⁶ represents a

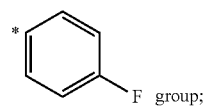
F group;

wherein * indicates the point of attachment of said group with the rest of the molecule;
R⁷ represents a $C_1$-$C_3$-alkyl- or a cyclopropyl- group;
R⁸ represents a hydrogen atom or a $C_1$-$C_6$-alkyl- or $C_3$-$C_6$-cycloalkyl- group, wherein said $C_1$-$C_6$-alkyl- or $C_3$-$C_6$-cycloalkyl- group is optionally substituted, one or more times, with a halogen atom;
or
R⁷ and R⁸ together with the molecular fragment they are attached to represent a 4- to 6-membered heterocyclic ring, which is optionally substituted, one or more times, identically or differently, with a halogen atom, a $C_1$-$C_3$-alkyl-, halo-$C_1$-$C_3$-alkyl- or $C_1$-$C_3$-alkoxy- group;
R⁹ represents a group selected from: methyl-, hydroxy-$C_1$-$C_2$-alkyl-, —N(R¹⁰)R¹⁰, —$C_1$-$C_2$-alkyl-N(R¹⁰)R¹⁰;
R¹⁰ represents a hydrogen atom or a methyl- group;
and
Q represents CH;
or a tautomer, an N-oxide, a hydrate, a solvate, or a salt thereof, or a mixture of same.

In another preferred embodiment, the invention relates to compounds of formula (I)

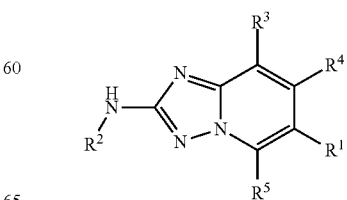

(I)

in which:

R¹ represents

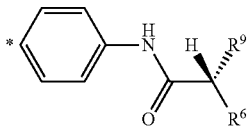

wherein * indicates the point of attachment of said group with the rest of the molecule;

R² represents

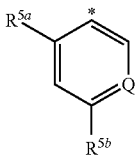

wherein * indicates the point of attachment of said group with the rest of the molecule;

R³ represents a hydrogen atom;
R⁴ represents a hydrogen atom;
R⁵ represents a hydrogen atom;
R$^{5a}$ represents a group selected from: $C_1$-$C_2$-alkoxy-, halo-$C_1$-$C_2$-alkoxy-;
R$^{5b}$ represents a group selected from:
—C(=O)N(H)R⁸, —C(=O)NR⁸R⁷, —N(R⁷)C(=O)OR⁸, R⁷—S(=O)₂—;
R⁶ represents a

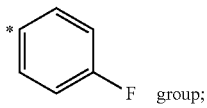

wherein * indicates the point of attachment of said group with the rest of the molecule;

R⁷ represents a $C_1$-$C_3$-alkyl- or a cyclopropyl- group;
R⁸ represents a hydrogen atom or a $C_1$-$C_6$-alkyl- or $C_3$-$C_6$-cycloalkyl- group, wherein said $C_1$-$C_6$-alkyl- or $C_3$-$C_6$-cycloalkyl- group is optionally substituted, one or more times, with a halogen atom;

or

R⁷ and R⁸ together with the molecular fragment they are attached to represent a 4- to 6-membered heterocyclic ring, which is optionally substituted, one or more times, identically or differently, with a halogen atom, a $C_1$-$C_3$-alkyl-, halo-$C_1$-$C_3$-alkyl- or $C_1$-$C_3$-alkoxy- group;

R⁹ represents a group selected from: methyl-, hydroxymethyl-, —NH₂;

and

Q represents CH;

or a tautomer, an N-oxide, a hydrate, a solvate, or a salt thereof, or a mixture of same.

In another preferred embodiment, the invention relates to compounds of formula (I), wherein:

R¹ represents

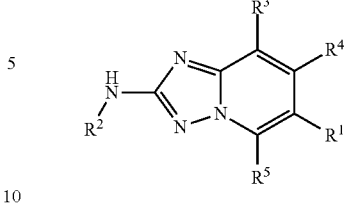

in which:

R¹ represents

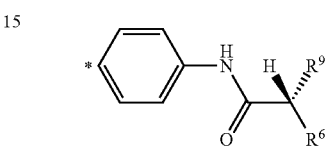

wherein * indicates the point of attachment of said group with the rest of the molecule;

R² represents

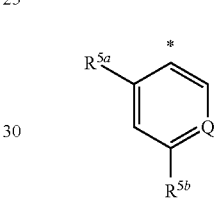

wherein * indicates the point of attachment of said group with the rest of the molecule;

R³ represents a hydrogen atom;
R⁴ represents a hydrogen atom;
R⁵ represents a hydrogen atom;
R$^{5a}$ represents a group selected from: $C_1$-$C_4$-alkoxy-, halo-$C_1$-$C_4$-alkoxy-, $C_1$-$C_4$-alkyl;
R$^{5b}$ represents a group selected from:
—C(=O)N(H)R⁸, —C(=O)NR⁸R⁷;
R⁶ represents a

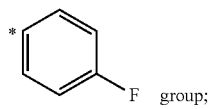

wherein * indicates the point of attachment of said group with the rest of the molecule;
wherein said group is optionally substituted, one or more times, identically or differently, with a halogen atom or a methyl- group;

R⁷ represents a $C_1$-$C_3$-alkyl- group;
R⁸ represents a hydrogen atom or a $C_1$-$C_3$-alkyl- group;
wherein said $C_1$-$C_3$-alkyl- group is optionally substituted, one or more times, with a halogen atom;

or

R⁷ and R⁸ together with the molecular fragment they are attached to represent a 4- to 6-membered heterocyclic ring, which is optionally substituted, one or more times, identically or differently, with a halogen atom;

R⁹ represents a group selected from: $C_1$-$C_3$-alkyl-, hydroxy-$C_1$-$C_3$-alkyl-, —N(R¹⁰)R¹⁰, —$C_1$-$C_2$-alkyl-N(R¹⁰)R¹⁰;

$R^{10}$ represents a hydrogen atom or a methyl- group;
and
Q represents CH or N;
or a tautomer, an N-oxide, a hydrate, a solvate, or a salt thereof, or a mixture of same.

In another preferred embodiment, the invention relates to compounds of formula (I)

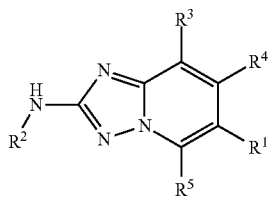
(I)

in which:
$R^1$ represents

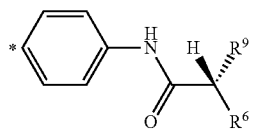

wherein * indicates the point of attachment of said group with the rest of the molecule;
$R^2$ represents

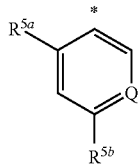

wherein * indicates the point of attachment of said group with the rest of the molecule;
$R^3$ represents a hydrogen atom;
$R^4$ represents a hydrogen atom;
$R^5$ represents a hydrogen atom;
$R^{5a}$ represents a group selected from: $C_1$-$C_4$-alkoxy-, halo-$C_1$-$C_4$-alkoxy-, $C_1$-$C_4$-alkyl;
$R^{5b}$ represents a —N($R^7$)C(=O)O$R^8$ group;
$R^6$ represents a

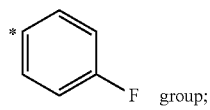
group;

wherein * indicates the point of attachment of said group with the rest of the molecule;
wherein said group is optionally substituted, one or more times, identically or differently, with a halogen atom or a methyl- group;
$R^7$ and $R^8$ together with the molecular fragment they are attached to represent a 4- to 6-membered heterocyclic ring;

$R^9$ represents a group selected from: methyl-, hydroxy-$C_1$-$C_2$-alkyl-, —NH$_2$, —N($R^{10}$)$R^{10}$, —$C_1$-$C_2$-alkyl-N($R^{10}$)$R^{10}$;
$R^{10}$ represents a hydrogen atom or a methyl- group;
and
Q represents CH or N;
or a tautomer, an N-oxide, a hydrate, a solvate, or a salt thereof, or a mixture of same.

In another preferred embodiment, the invention relates to compounds of formula (I)

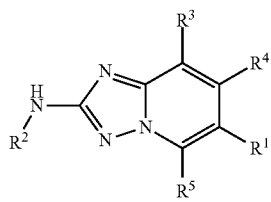
(I)

in which:
$R^1$ represents

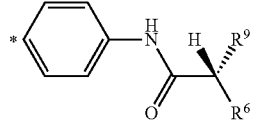

wherein * indicates the point of attachment of said group with the rest of the molecule;
$R^2$ represents

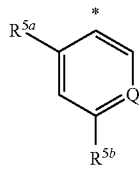

wherein * indicates the point of attachment of said group with the rest of the molecule;
$R^3$ represents a hydrogen atom;
$R^4$ represents a hydrogen atom;
$R^5$ represents a hydrogen atom;
$R^{5a}$ represents a group selected from: $C_1$-$C_4$-alkoxy-, halo-$C_1$-$C_4$-alkoxy-, $C_1$-$C_4$-alkyl;
$R^{5b}$ represents a $R^7$—S(=O)$_2$— group;
$R^6$ represents a

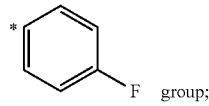
group;

wherein * indicates the point of attachment of said group with the rest of the molecule;
wherein said group is optionally substituted, one or more times, identically or differently, with a halogen atom or a methyl- group;
$R^7$ represents a $C_1$-$C_3$-alkyl- group;

$R^8$ represents a hydrogen atom or a $C_1$-$C_6$-alkyl- or $C_3$-$C_6$-cycloalkyl- group, wherein said $C_1$-$C_6$-alkyl- or $C_3$-$C_6$-cycloalkyl- group is optionally substituted, one or more times, with a halogen atom;

$R^9$ represents a group selected from: methyl-, hydroxy-$C_1$-$C_2$-alkyl-, —$NH_2$, —$N(R^{10})R^{10}$, —$C_1$-$C_2$-alkyl-$N(R^{10})R^{10}$;

$R^{10}$ represents a hydrogen atom or a methyl- group;

and

Q represents CH or N;

or a tautomer, an N-oxide, a hydrate, a solvate, or a salt thereof, or a mixture of same.

In another preferred embodiment, the invention relates to compounds of formula (I)

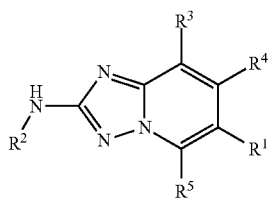

(I)

in which:

$R^1$ represents

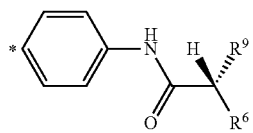

wherein * indicates the point of attachment of said group with the rest of the molecule;

$R^2$ represents

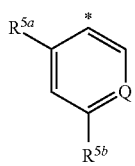

wherein * indicates the point of attachment of said group with the rest of the molecule;

$R^3$ represents a hydrogen atom;

$R^4$ represents a hydrogen atom;

$R^5$ represents a hydrogen atom;

$R^{5a}$ represents a group selected from: $C_1$-$C_2$-alkoxy-, halo-$C_1$-$C_2$-alkoxy-;

$R^{5b}$ represents a group selected from:
—C(=O)N(H)$R^8$, —C(=O)N$R^8R^7$, —N($R^7$)C(=O)O$R^8$, $R^7$—S(=O)$_2$—;

$R^6$ represents a

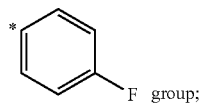

F group;

wherein * indicates the point of attachment of said group with the rest of the molecule;

$R^7$ represents a $C_1$-$C_3$-alkyl- group;

$R^8$ represents a hydrogen atom or a $C_1$-$C_3$-alkyl- group, wherein said $C_1$-$C_3$-alkyl- group is optionally substituted, one or more times, with a halogen atom;

or $R^7$ and $R^8$ together with the molecular fragment they are attached to represent a 4- to 6-membered heterocyclic ring, which is optionally substituted, one or more times, identically or differently, with a halogen atom;

$R^9$ represents a group selected from: methyl-, hydroxy-$C_1$-$C_2$-alkyl-, —$N(R^{10})R^{10}$, —$C_1$-$C_2$-alkyl-$N(R^{10})R^{10}$;

$R^{10}$ represents a hydrogen atom or a methyl- group;

and

Q represents CH or N;

or a tautomer, an N-oxide, a hydrate, a solvate, or a salt thereof, or a mixture of same.

In another preferred embodiment, the invention relates to compounds of formula (I)

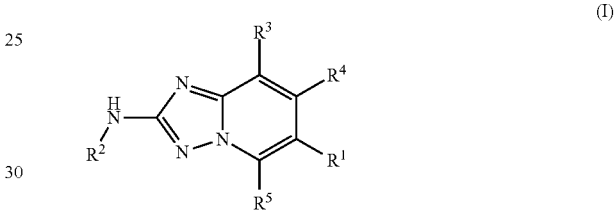

(I)

in which:

$R^1$ represents a group selected from:

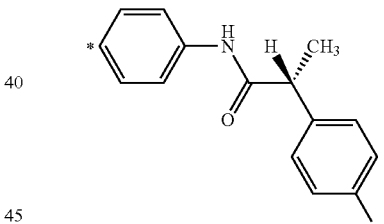

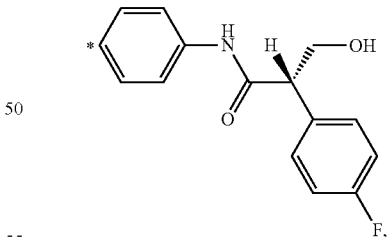

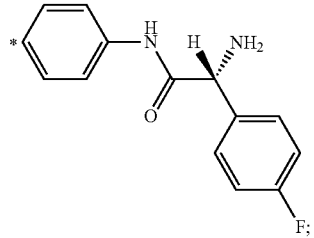

wherein * indicates the point of attachment of said group with the rest of the molecule;

R² represents

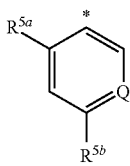

wherein * indicates the point of attachment of said group with the rest of the molecule;
R³ represents a hydrogen atom;
R⁴ represents a hydrogen atom;
R⁵ represents a hydrogen atom;
R⁵ᵃ represents a group selected from: methoxy-, ethoxy-, F₃C—CH₂—O—;
R⁵ᵇ represents a group selected from:
H₃C—S(O)₂—, H₂N—C(O)—, (CH₃)₂N—C(O)—,

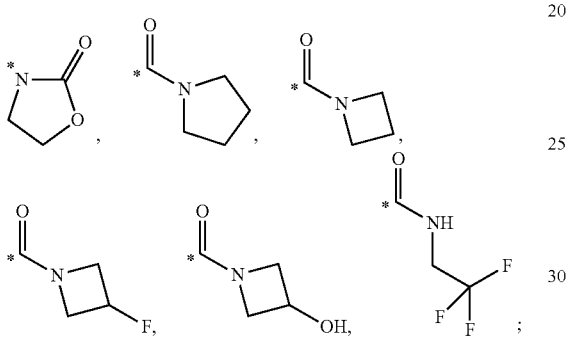

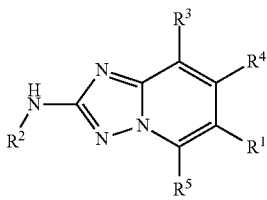

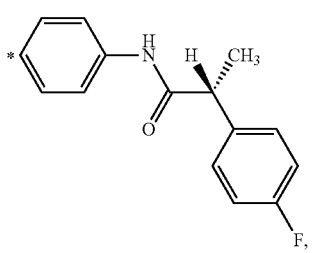

wherein * indicates the point of attachment of said group with the rest of the molecule;
and
Q represents CH;
or a tautomer, an N-oxide, a hydrate, a solvate, or a salt thereof, or a mixture of same.

In another preferred embodiment, the invention relates to compounds of formula (I)

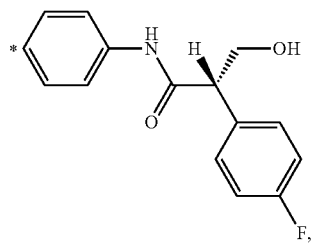

(I)

in which:
R¹ represents a group selected from:

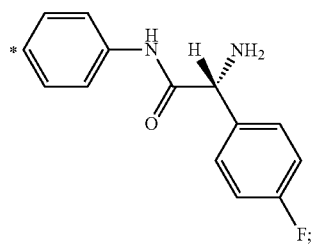

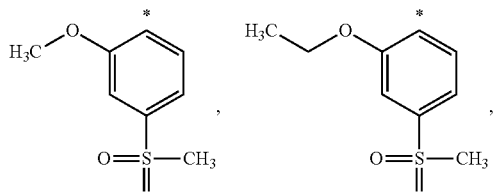

wherein * indicates the point of attachment of said group with the rest of the molecule;
R² represents a group selected from:

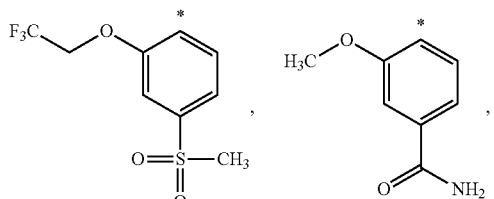

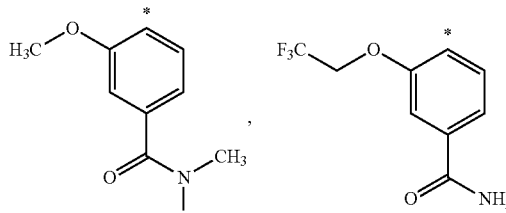

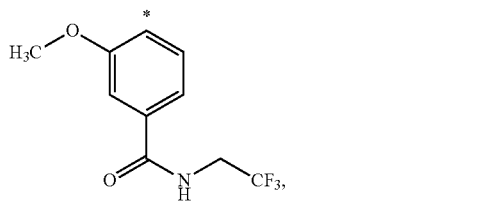

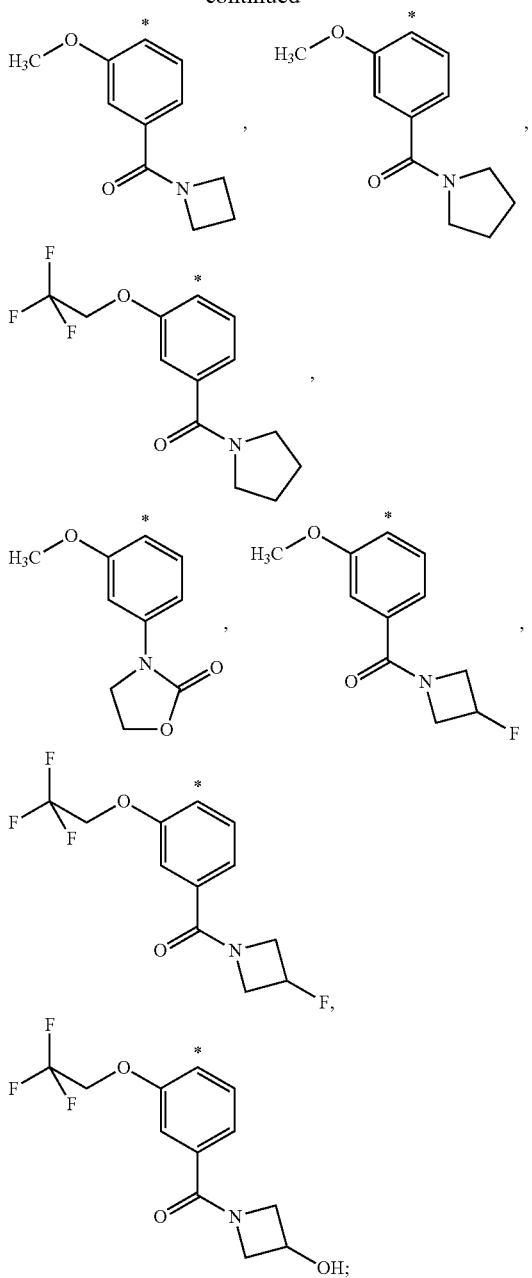

wherein * indicates the point of attachment of said group with the rest of the molecule;
R³ represents a hydrogen atom;
R⁴ represents a hydrogen atom; and
R⁵ represents a hydrogen atom;
or a tautomer, an N-oxide, a hydrate, a solvate, or a salt thereof, or a mixture of same.

It is to be understood that the present invention relates to any sub-combination within any embodiment of the present invention of compounds of general formula (I), supra.

More particularly still, the present invention covers compounds of general formula (I) which are disclosed in the Example section of this text, infra.

In accordance with another aspect, the present invention covers methods of preparing compounds of the present invention, said methods comprising the steps as described in the Experimental Section herein.

In a preferred embodiment, the present invention relates to a method of preparing compounds of general formula (I), supra, in which method an intermediate compound of general formula (5):

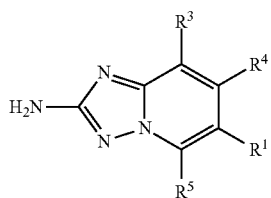

(5)

in which $R^1$, $R^3$, $R^4$, and $R^5$ are as defined for the compounds of general formula (I), supra, is allowed to react with an aryl compound of general formula (5a):

$$R^2—Y \qquad (5a)$$

in which $R^2$ is as defined for the compounds of general formula (I), supra, and Y represents a leaving group, such as a halogen atom or a trifluoromethylsulphonyloxy or nonafluorobutylsulphonyloxy group for example, thus providing a compound of general formula (I):

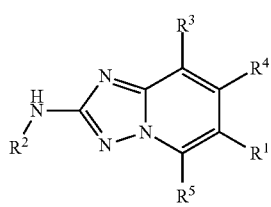

(I)

in which $R^1$, $R^2$, $R^3$, $R^4$, and $R^5$ are as defined for the compounds of general formula (I), supra.

In a more preferred embodiment, the present invention relates to a method of preparing compounds of general formula (I), supra, in which method an intermediate compound of general formula (5):

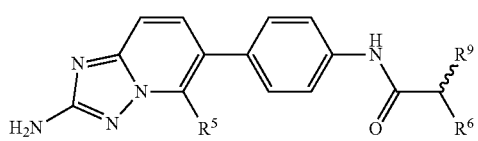

(5)

in which $R^5$, $R^6$, and $R^9$ are as defined for the compounds of general formula (I), supra, is allowed to react with an aryl compound of general formula (5a):

$$R^2—Y \qquad (5a)$$

in which $R^2$ is as defined for the compounds of general formula (I), supra, and Y represents a leaving group, such as a halogen atom or a trifluoromethylsulphonyloxy or nonafluorobutylsulphonyloxy group for example, thus providing a compound of general formula (Ia):

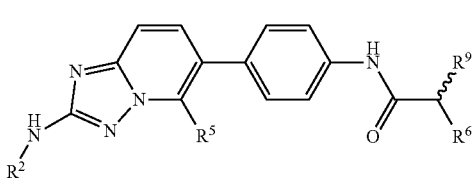 (Ia)

in which R², R⁵, R⁶, and R⁹ are as defined for the compounds of general formula (I), supra;
and
optionally: in which a compound of formula (I):

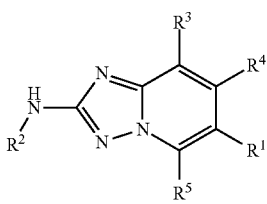 (I)

in which R¹, R², R³, R⁴, and R⁵ are as defined for the compounds of general formula (I), supra,
is separated from a compound of formula (Ib):

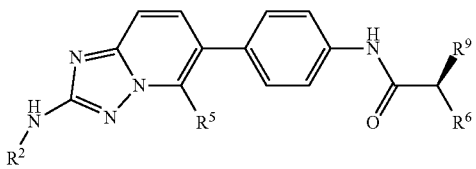 (Ib)

in which R², R⁵, R⁶, and R⁹ are as defined for the compounds of general formula (I), supra.

In another preferred embodiment, the present invention relates to a method of preparing compounds of general formula (I), supra, in which method an intermediate compound of general formula (7):

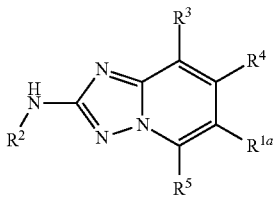 (7)

in which R², R³, R⁴, and R⁵ are as defined for the compounds of general formula (I), supra, and R¹ᵃ is a phenyl group to which an —NH₂ substituent is bound in the para position, is allowed to react with a compound of general formula (7a):

R¹ᵇ—X (7a)

wherein R¹ᵇ—X represents

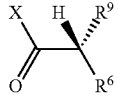

in which R⁹ and R⁶ are as defined for the compounds of general formula (I), supra, and X is a suitable functional group (e.g. an —OH, —O—C₁-C₆-alkyl group, or a halogen atom), via which the R¹ᵇ of the R¹ᵇ—X compound (7a) can be coupled, via a coupling reaction, such as an amide coupling reaction for example, onto the —NH₂ substituent bound to the phenyl group R¹ᵃ of compound (7),
thus providing a compound of general formula (I):

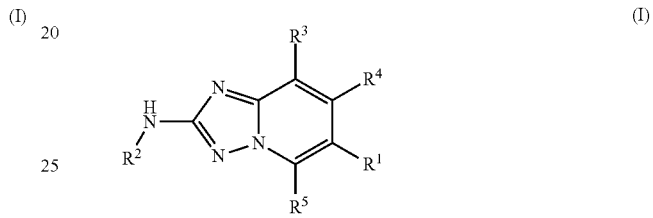 (I)

in which R¹, R², R³, R⁴, and R⁵ are as defined for the compounds of general formula (I), supra.

In another preferred embodiment, the present invention relates to a method of preparing compounds of general formula (I), supra, in which method an intermediate compound of general formula (7):

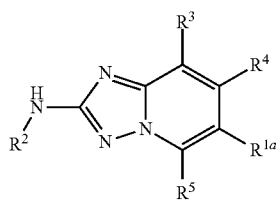 (7)

in which R², R³, R⁴, and R⁵ are as defined for the compounds of general formula (I), supra, and R¹ᵃ is a phenyl group to which an —NH₂ substituent is bound in the para position, is allowed to react with a compound of general formula (7a):

R¹ᵇ—X (7a)

wherein R¹ᵇ—X represents

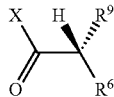

in which R⁹ and R⁶ are as defined for the compounds of general formula (I), supra, and X is a suitable functional group (e.g. an —OH), via which the R¹ᵇ of the R¹ᵇ—X compound (7a) can be coupled, via a coupling reaction, such as an amide coupling reaction using a coupling reagent like for example HATU, and a base like for example sodium bicarbonate in an inert solvent like for example THF, DMF, DCM, NMP or mixtures thereof, onto the —NH₂ substituent bound to the phenyl group $R^{1a}$ of compound (7), thus providing a compound of general formula (I):

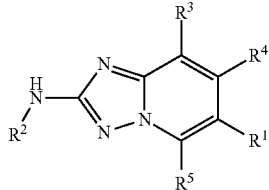
(I)

in which $R^1$, $R^2$, $R^3$, $R^4$, and $R^5$ are as defined for the compounds of general formula (I), supra.

In another embodiment, the present invention relates to a method of preparing compounds of general formula (I), supra, in which method an intermediate compound of general formula (7):

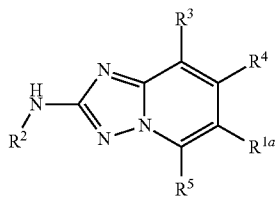
(7)

in which $R^2$, $R^3$, $R^4$, and $R^5$ are as defined for the compounds of general formula (I), supra, and $R^{1a}$ is a phenyl group to which an —NH₂ substituent is bound in the para position, is allowed to react with a compound of general formula (7a):

$R^{1b}$—X  (7a)

wherein $R^{1b}$—X represents

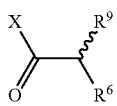

in which $R^9$ and $R^6$ are as defined for the compounds of general formula (I), supra, and X is a suitable functional group (e.g. an —OH, —O—$C_1$-$C_6$-alkyl group, or a halogen atom), via which the $R^{1b}$ of the $R^{1b}$—X compound (7a) can be coupled, via a coupling reaction, such as an amide coupling reaction for example, onto the —NH₂ substituent bound to the phenyl group $R^{1a}$ of compound (7), thus providing a compound of general formula (Ia):

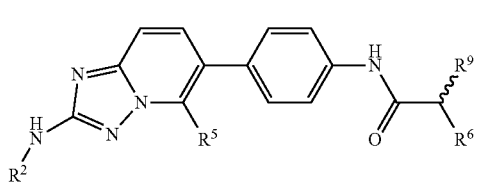
(Ia)

in which $R^2$, $R^5$, $R^6$, and $R^9$ are as defined for the compounds of general formula (I), supra;

and
optionally: in which a compound of formula (I):

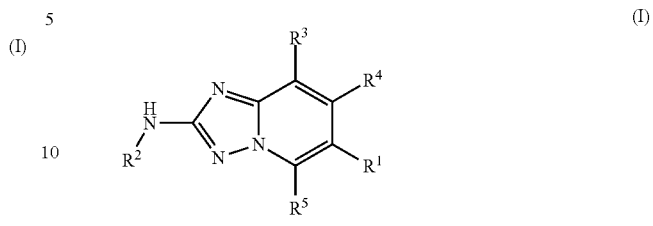
(I)

in which $R^1$, $R^2$, $R^3$, $R^4$, and $R^5$ are as defined for the compounds of general formula (I), supra, is separated from a compound of formula (Ib):

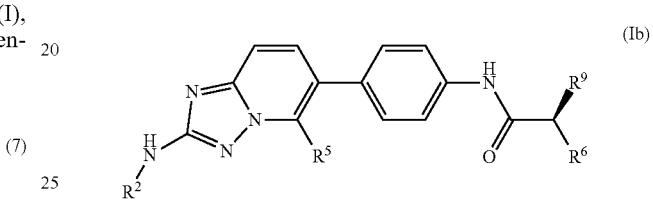
(Ib)

in which $R^2$, $R^5$, $R^6$, and $R^9$ are as defined for the compounds of general formula (I), supra.

In another embodiment, the present invention relates to a method of preparing compounds of general formula (I), supra, in which method an intermediate compound of general formula (4):

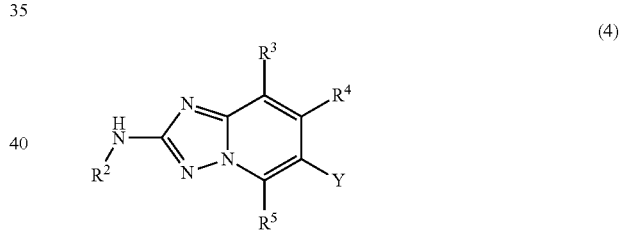
(4)

in which $R^2$, $R^3$, $R^4$, and $R^5$ are as defined for the compound of general formula (I), supra, and Y represents a leaving group, such as a halogen atom or a trifluoromethylsulphonyloxy or nonafluorobutylsulphonyloxy group for example, is allowed to react with a compound of general formula:

$R^1$—Z in which $R^1$ is as defined for the compounds of general formula (I), supra, and Z represents a suitable functional group like for example a boronic acid or a boronic ester, thus providing a compound of general formula (I):

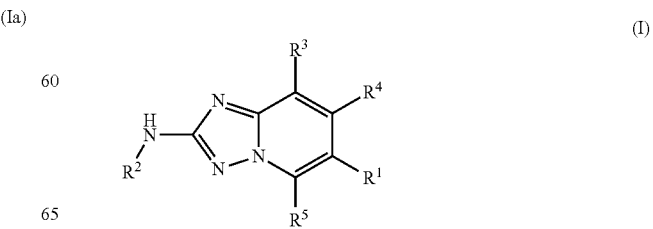
(I)

in which $R^1$, $R^2$, $R^3$, $R^4$, and $R^5$ are as defined for the compounds of general formula (I), supra.

In another embodiment, the present invention relates to a method of preparing compounds of general formula (I), supra, in which method an intermediate compound of general formula (4):

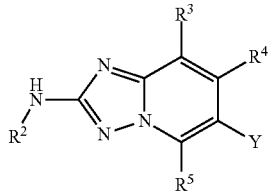

(4)

in which $R^2$, $R^3$, $R^4$, and $R^5$ are as defined for the compound of general formula (I), supra, and Y represents a leaving group, such as a halogen atom or a trifluoromethylsulphonyloxy or nonafluorobutylsulphonyloxy group for example, is allowed to react with a compound of general formula:

$R^1$—Z in which $R^1$ represents

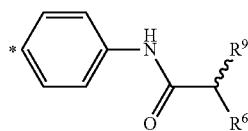

wherein * indicates the point of attachment of said group with the rest of the molecule, $R^6$ and $R^9$ are is as defined for the compounds of general formula (I), supra, and Z represents a suitable functional group like for example a boronic acid or a boronic ester, thus providing a compound of general formula (Ia):

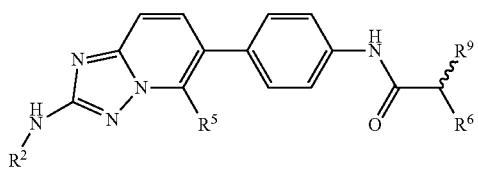

(Ia)

in which $R^2$, $R^5$, $R^6$, and $R^9$ are as defined for the compounds of general formula (I), supra;
and
optionally: in which a compound of formula (I):

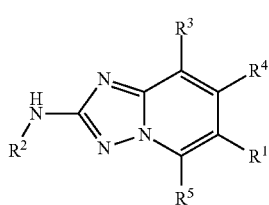

(I)

in which $R^1$, $R^2$, $R^3$, $R^4$, and $R^5$ are as defined for the compounds of general formula (I), supra,
is separated from a compound of formula (Ib):

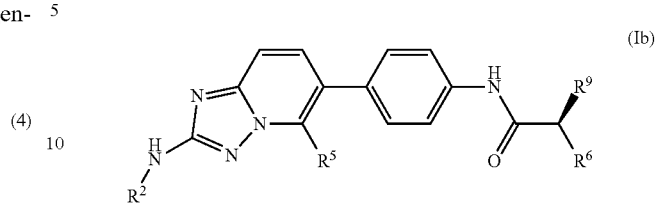

(Ib)

in which $R^2$, $R^5$, $R^6$, and $R^9$ are as defined for the compounds of general formula (I), supra.

For elucidation purposes:
A compound of formula (Ia)

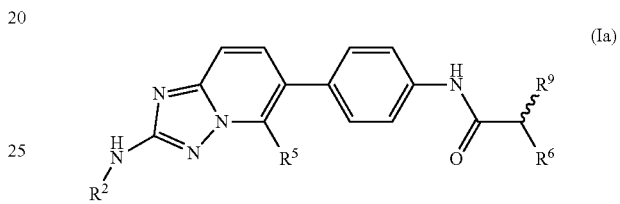

(Ia)

is a mixture of a compound of formula (Ib)

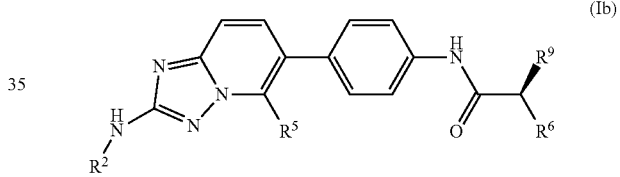

(Ib)

and a compound of formula (Ic)

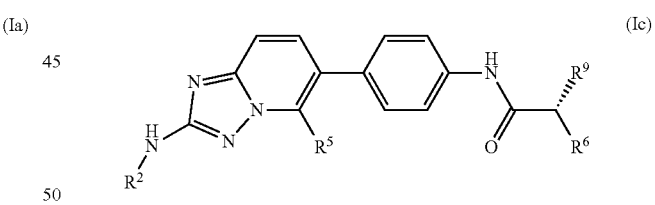

(Ic)

in any ratio.

Usually, a compound of formula (Ia) is a racemic mixture, which means, it contains equal amounts of a compound of formula (Ib) and of a compound of formula (Ic). However, it should not be limited to a racemic mixture, but can be of any ratio.

The same applies to other compounds comprising the moiety:

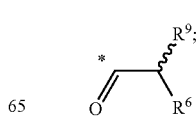

wherein * indicates the point of attachment of said group with the rest of the molecule, and $R^6$ and $R^9$ are as defined for the compounds of general formula (I), supra.

In accordance with a further aspect, the present invention covers intermediate compounds which are useful in the preparation of compounds of the present invention of general formula (I), particularly in the method described herein. In particular, the present invention covers compounds of general formula (5):

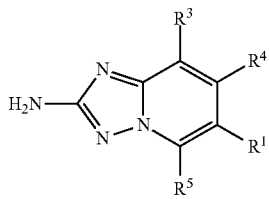

(5)

in which $R^1$, $R^3$, $R^4$, and $R^5$ are as defined for the compounds of general formula (I), supra, or a stereoisomer, a tautomer, an N-oxide, a hydrate, a solvate, or a salt thereof, or a mixture of same.

In accordance with yet another aspect, the present invention covers the use of the intermediate compounds:

(a) of general formula (5):

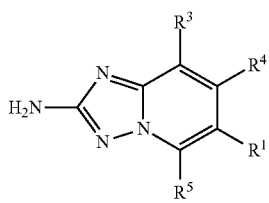

(5)

in which $R^1$, $R^3$, $R^4$, and $R^5$ are as defined for the compounds of general formula (I), supra, or (b) of general formula (7):

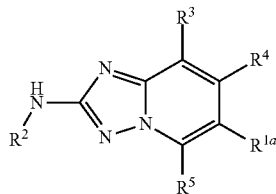

(7)

in which $R^2$, $R^3$, $R^4$, and $R^5$ are as defined for the compounds of general formula (I), supra, and $R^{1a}$ is a phenyl group to which an —NH$_2$ substituent is bound in para position, or (c) of general formula (4):

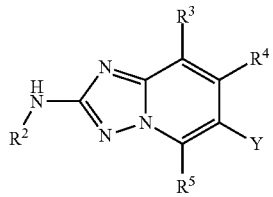

(4)

in which $R^2$, $R^3$, $R^4$, and $R^5$ are as defined for the compounds of general formula (I), supra, and Y represents a leaving group, such as a halogen atom or a trifluoromethylsulphonyloxy or nonafluorobutylsulphonyloxy group for example, for the preparation of compounds of general formula (I).

As one of ordinary skill in the art is aware of, the methods described above may comprise further steps like e.g. the introduction of a protecting group and the cleavage of the protecting group. Particularly, if $R^1$ or $R^9$ comprises an H$_2$N— group or a HO— group, these groups usually will be protected by suitable protecting groups PG$^1$ and PG$^2$, as described herein, prior to the respective coupling reactions. The protecting group will be removed after the coupling reaction.

EXPERIMENTAL SECTION

The following Table lists the abbreviations used in this paragraph, and in the Examples section. NMR peak forms are stated as they appear in the spectra, possible higher order effects have not been considered.

| Abbreviation | Meaning |
|---|---|
| Ac | acetyl |
| BINAP | 2,2'-bis(diphenylphosphino)-1,1'-binaphthyl |
| Boc | tert-butyloxycarbonyl |
| br | broad |
| Brett-Phos | 2-(dicyclohexylphosphino)-3,6-dimethoxy-2'-4'-6'-tri-i-propyl-1,1'-biphenyl |
| c- | cyclo- |
| d | doublet |
| dd | doublet of doublets |
| DCM | dichloromethane |
| DME | 1,2-dimethoxyethane |
| DIPE | diisopropylether |
| DIPEA | N,N-diisopropylethylamine |
| DMF | N,N-dimethylformamide |
| DMSO | dimethyl sulfoxide |
| Dppf | 1,1'-bis(diphenylphosphino)ferrocene |
| Eq | equivalent |
| ESI | electrospray ionisation |
| HATU | N-[(dimethylamino)(3H-[1,2,3]triazolo[4,5-b]pyridin-3-yloxy)-methylene]-N-methylmethanaminium hexafluorophosphate |
| Hünig Base | N,N-diisopropylethylamine |
| m | multiplet |
| m.p. | melting point in ° C. |

-continued

| Abbreviation | Meaning |
|---|---|
| MS | mass spectrometry |
| MW | molecular weight |
| NaOtBu | sodium tert-butoxide; sodium 2-methylpropan-2-olate |
| NMP | N-methylpyrrolidinone |
| NMR | nuclear magnetic resonance spectroscopy: chemical shifts ($\delta$) are given in ppm. |
| $PdCl_2(PPh_3)_2$ | dichlorobis(triphenylphosphine)palladium(II) |
| $Pd(dba)_2$ | bis-(dibenzylideneacetone)palladium(0) complex |
| $Pd_2(dba)_3$ | tris-(dibenzylideneacetone)dipalladium(0) chloroform complex |
| $Pd(dppf)Cl_2$ | dichloro[1,1'-bis(diphenylphosphino)ferrocene]palladium(II) |
| $Pd(dppf)Cl_2 \cdot CH_2Cl_2$ | dichloro[1,1'-bis(diphenylphosphino)ferrocene]palladium(II) dichloromethane adduct |
| Pd-Brett-Phos-pre-cat | chloro[2-(dicyclohexylphosphino)-3,6-dimethoxy-2'-4'-6'-tri-iso-propyl-1,1'-biphenyl][2-(2-aminoethyl)phenyl]palladium(II) |
| Pd-tBu-X-Phos-pre-cat | chloro(2-di-tert-butylphosphino-2',4',6'-tri-isopropyl-1,1'-biphenyl)[2-(2-aminoethyl)phenyl] palladium(II), |
| Pd-X-Phos-pre-cat | chloro(2-dicyclohexylphosphino-2',4',6'-tri-isopropyl-1,1'-biphenyl)[2-(2-aminoethyl)phenyl] palladium(II) methyl-tert-butylether adduct |
| $PPh_3$ | triphenylphosphine |
| $P(oTol)_3$ | tri-o-tolylphosphine |
| q | quartet |
| quin | quintett |
| Rac | racemic |
| Rt | room temperature |
| r.t. | room temperature |
| RT | retention time in minutes |
| s | singlet |
| t | triplet |
| TBAF | tetrabutylammoniumfluoride |
| tBu-X-Phos | 2-di-tert-butylphosphino-2',4',6'-tri-isopropyl-1,1'-biphenyl |
| TBDPS | tert-butyldiphenylsilyl |
| TBTU | N-[(1H-benzotriazol-1-yloxy)(dimethylamino)methylene]-N-methylmethanaminium tetrafluoroborate |
| TEA | triethylamine |
| TFA | trifluoroacetic acid |
| THF | tetrahydrofuran |
| TMS | trimethylsilyl |
| Ts | para toluenesulfonyl; (tosyl) |
| UPLC | ultra performance liquid chromatography |
| X-Phos | 2-dicyclohexylphosphino-2',4',6'-triisopropylbiphenyl |

The schemes and procedures described below illustrate general synthetic routes to the compounds of general formula (I) of the invention and are not intended to be limiting. It is clear to the person skilled in the art that the order of transformations as exemplified in the schemes can be modified in various ways. The order of transformations exemplified in the schemes is therefore not intended to be limiting. In addition, interconversion of any of the substituents, in particular of $R^1$ or $R^2$, can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, $3^{rd}$ edition, Wiley 1999). Specific examples are described in the subsequent paragraphs.

A first reaction scheme is outlined infra:

Synthesis of Compounds of General Formula (I) of the Present Invention

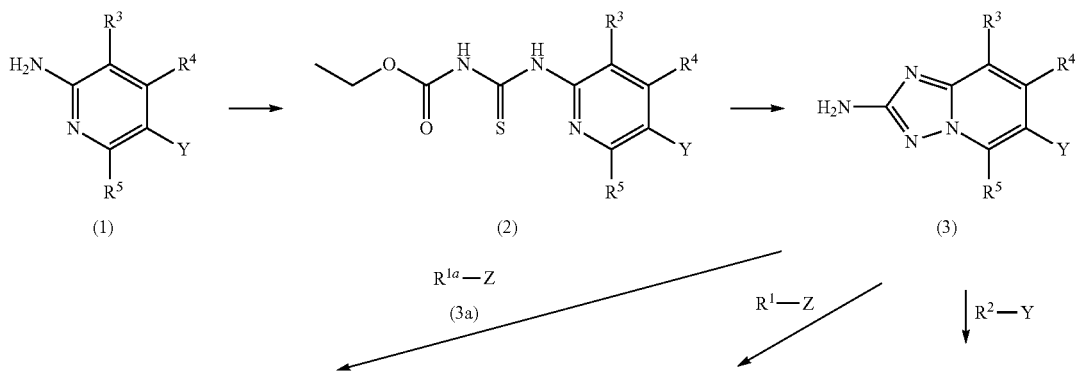

-continued

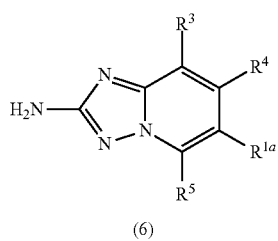
(6)

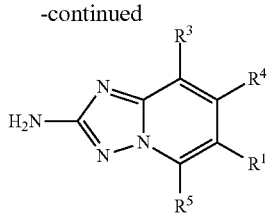
(5)

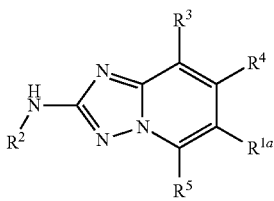
(4)

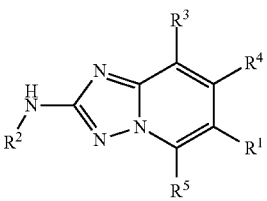
(7)

(I)

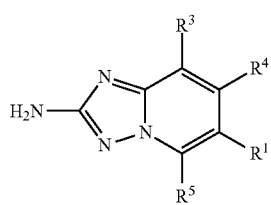
(5)

In scheme 1:
R¹ represents either

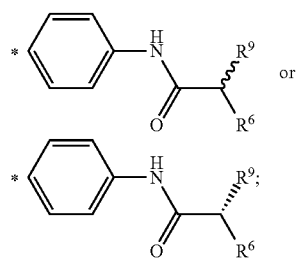
or $R^{1a}$ is a phenyl group to which an —NH₂ substituent or a protected amino group (protected by PG² as defined above, e.g. by a Boc group) is bound in para position;
$R^{1b}$ represents either

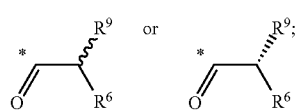

wherein * indicates the point of attachment of said groups with the rest of the molecule;
$R^2$, $R^3$, $R^4$, $R^5$, and $R^6$ are as defined for the compounds of general formula (I), supra;

$R^9$ is as defined for the compounds of general formula (I), supra, whereas, if $R^9$ comprises a OH or NH₂ moiety, $R^9$ represents the respective protected group (protected by PG¹ or PG² as defined herein), as known to the person of ordinary skill in the art (see e.g. examples Example01.10 and Example01.11 as well as intermediates Int08.143 and Int08.150);

X represents a suitable functional group (e.g. an —OH or —O—$C_1$-$C_6$-alkyl group, or a halogen atom), via which the $R^{1b}$ group of $R^{1b}$—X can be coupled, via a coupling reaction onto the —NH₂ substituent bound to the phenyl group of $R^{1a}$, thus providing a compound of general formula (I);

Y represents a leaving group, such as a halogen atom or a trifluoromethylsulphonyloxy or nonafluorobutylsulphonyloxy group for example; and Z represents a suitable functional group via which the R¹ of the R¹—Z compound can be coupled, by a coupling reaction, onto the Y-bearing carbon atom of a compound (4), such as a halogen atom or a trifluoromethylsulphonyloxy or nonafluorobutylsulphonyloxy group for example, thereby replacing said Y with said R¹ moiety.

In case of R¹ being

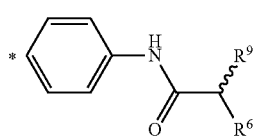

a separation step may be required after the reaction steps
(4)→(I),
(5)→(I), and
(7)→(I),
in order to separate the desired compound of formula (Ic):

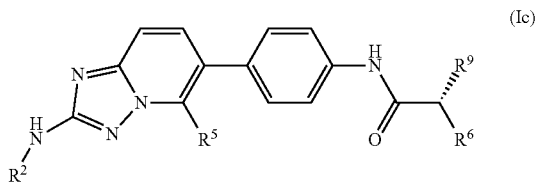

from the respective antipode of formula (Ib):

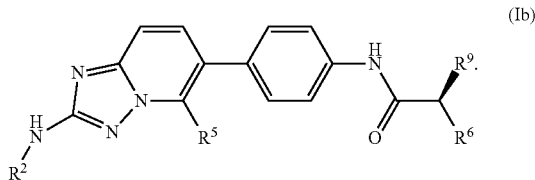

The optical isomers can be obtained by resolution of the racemic mixtures according to conventional processes, for example, by the formation of diastereoisomeric salts using an optically active acid or base or formation of covalent diastereomers. Mixtures of diastereoisomers can be separated into their individual diastereomers on the basis of their physical and/or chemical differences by methods known in the art, for example, by chromatography or fractional crystallisation. The optically active isomers are then liberated from the separated diastereomeric salts or from the covalent diastereomers. A different process for separation of optical isomers involves the use of chiral chromatography (e.g., chiral HPLC columns), with or without conventional derivatisation, optimally chosen to maximise the separation of the enantiomers. Suitable chiral HPLC columns are e.g. Chiracel OD and Chiracel OJ among many others, alt routinely selectable. Enzymatic separations, with or without derivatisation, are also useful. The optically active compounds of this invention can likewise be obtained by chiral syntheses utilizing optically active starting materials or chiral auxiliaries as described in the literature (e.g. Jiang, Y; Chen, C A; Lu, K; Daniewska, I; De Leon, J; Kong, R; Forray, C; Li, B; Hegde, L G; Wolinsky, T D; Craig, D A; Wetzel, J M; Andersen, K; Marzabadi, M R: J. Med. Chem. 2007, 50, 3870).

Compounds of general formula (I) can be synthesised according to the procedures depicted in scheme 1.

Many aryl halides of the formula $R^2$—Y may be obtained commercially. Reagents of the general structure $R^{1a}$—Z and $R^1$—Z can for example be aryl boronic acids or aryl boronic esters. Many such reagents of the general structures $R^{1a}$—Z and $R^1$—Z are also commercially available. Reagents of the general structures $R^{1a}$—Z and $R^1$—Z can be prepared from aryl halides [see for example K. L. Billingslay, T. E. Barde, S. L Buchwald, Angew. Chem. 2007, 119, 5455 or T. Graening, Nachrichten aus der Chemie, January 2009, 57, 34].

The person skilled in the art will recognise that there are many precedented methods for synthesising suitable 3,4,6-substituted 5-halo-pyridin-2-ylamines of general formula (1); some 3,4,6-substituted 5-halo-pyridin-2-ylamines may be obtained commercially.

A suitably substituted 5-halo-pyridin-2-ylamine intermediate of general formula (1) is converted to the corresponding intermediate of general formula (2) by reaction with a suitable oxycarbonylisothiocyanat, such as for example ethoxycarbonylisothiocyanat at temperatures ranging from room temperature to the boiling point of the solvent, preferably room temperature [see for example M. Nettekoven, B. Püllmann, S. Schmitt, Synthesis 2003, 1643-1652].

Intermediates of general formula (2) may be converted to 6-Halo-[1,2,4]triazolo[1,5-a]pyridin-2-ylamine intermediates of general formula (3) by reaction with a suitable reagent, for example hydroxylamine hydrochloride, in presence of a suitable base, such as, for example DIPEA in a suitable solvent system, such as, for example, methanol, ethanol, 1-propanol, 2-propanol or mixtures of these solvents at elevated temperatures, e.g. 60° C. [see for example M. Nettekoven, B. Püllmann, S. Schmitt, Synthesis 2003, 1643-1652].

Intermediates of general formula (3) can be converted to intermediates of general formula (4) by reaction with suitable aryl compounds $R^2$—Y, preferably aryl bromides, or aryl iodides or for example aryl trifluoromethylsulphonates or aryl nonafluorobutylsulphonates in the presence of a suitable base, such as, for example NaOtBu or cesium carbonate or potassium phosphate, and a suitable catalyst/ligand system, such as for example $Pd_2(dba)_3$/rac-BINAP, $Pd_2dba_3$/X-Phos, $Pd_2dba_3$/tBu-X-Phos, $Pd_2dba_3$/Brett-Phos, Pd—X-Phos-pre-cat/X-Phos, Pd-tBu-X-Phos-pre-cat/tBu-X-Phos, Pd-Brett-Phos-pre-cat/Brett-Phos in a suitable solvent such as THF, toluene, xylene, DME, or NMP, or mixtures of these solvents at temperatures ranging from room temperature to 200° C. The person skilled in the art will recognise that the appropriate choice of reaction conditions, such as temperature, choice of solvent and catalyst system is critical for preferred derivatization at the amino group of intermediates of general formula (3).

Intermediates of general formula (4) can be converted to compounds of general formula (I) by reaction with a suitable reagent $R^1$—Z, like for example a boronic acid derivative in the presence of a suitable catalyst system, like for example $Pd(OAc)_2$ and $P(oTol)_3$, or $PdCl_2(PPh_3)_2$ and $PPh_3$ and a suitable base, like for example aqueous potassium carbonate in a suitable solvent, like for example THF, DME, ethanol or 1-propanol or mixtures of these solvents at temperatures ranging from room temperature to 200° C., preferably the boiling point of the used solvent.

In an alternative route for the synthesis of compounds of general formula (I), intermediates of general formula (3) can be reacted with a suitable reagent $R^1$—Z, like for example a boronic acid derivative in the presence of a suitable catalyst system, like for example $Pd(OAc)_2$ and $P(oTol)_3$, or $PdCl_2(PPh_3)_2$ and $PPh_3$ and a suitable base, like for example aqueous potassium carbonate in a suitable solvent, like for example THF, DME, ethanol or 1-propanol or mixtures of these solvents at temperatures ranging from room temperature to 200° C., preferably the boiling point of the used solvent to furnish intermediates of the general formula (5).

Intermediates of general formula (5) can be converted to compounds of general formula (I) by reaction with suitable aryl compounds $R^2$—Y, preferably aryl bromides, or aryl iodides or for example aryl trifluoromethylsulphonates or aryl nonafluorobutylsulphonates in the presence of a suitable base, such as, for example NaOtBu or cesium carbonate or potassium phosphate, and a suitable catalyst/ligand system, such as for example Pd$_2$(dba)$_3$/rac-BINAP, Pd$_2$dba$_3$/X-Phos, Pd$_2$dba$_3$/tBu-X-Phos, Pd$_2$dba$_3$/Brett-Phos, Pd—X-Phos-pre-cat/X-Phos, Pd-tBu-X-Phos-pre-cat/tBu-X-Phos, Pd-Brett-Phos-pre-cat/Brett-Phos in a suitable solvent such as THF, toluene, xylene, DME, or NMP, or mixtures of these solvents at temperatures ranging from room temperature to the 200° C.

Also as depicted in scheme 1, is a further alternative route for the synthesis of compounds of general formula (I): Intermediates of general formula (3) can be converted to intermediates of general formula (6) by a coupling reaction with a reagent R$^{1a}$—Z as described supra for synthesis of intermediate of general formula (5), thereby replacing said Y of intermediates of general formula (3) with said R$^{1a}$ moiety.

Intermediates of general formula (6) can then be converted to intermediates of general formula (7) by a coupling reaction with a reagent R$^2$—Y as described supra for synthesis of intermediates of general formula (4), thereby forming a bond between NH and said R$^2$ moiety.

Intermediates of general formula (7) can then be converted to compounds of general formula (I) by one or more further transformations. These can be modifications such as cleavage of protecting groups, reduction or oxidation of functional groups, halogenation, metallation, substitution or other reactions known to the person skilled in the art, for example the formation of an amide bond, thereby converting R$^{1a}$ to said R$^1$ moiety.

Also as depicted in Scheme 1, is a further alternative route for the synthesis of compounds of general formula (I): Intermediates of general formula (3) can be converted to intermediates of general formula (6) by a coupling reaction with a reagent R$^{1a}$—Z as described supra for synthesis of intermediate of general formula (5), thereby replacing said Y of intermediates of general formula (3) with said R$^{1a}$ moiety.

Intermediates of general formula (6) can then be converted to intermediates of general formula (5) by one or more further transformations. These can be modifications such as cleavage of protecting groups, reduction or oxidation of functional groups, halogenation, metallation, substitution or other reactions known to the person skilled in the art, for example the formation of an amide bond, thereby converting R$^{1a}$ to said R$^1$ moiety.

Intermediates of general formula (5) can then be converted to compounds of general formula (I) by a coupling reaction with a reagent R$^2$—Y as described supra for synthesis of intermediates of general formula (4), thereby forming a bond between NH and said R$^2$ moiety.

Each of the Schemes 2-3, infra, illustrates specific transformations for the synthesis of some selected compounds according to general formula (I).

Scheme 2: Synthesis of compounds of general formula (11)

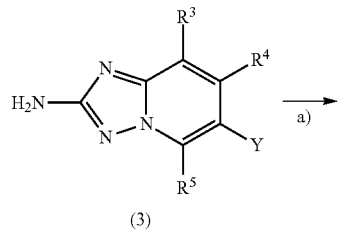

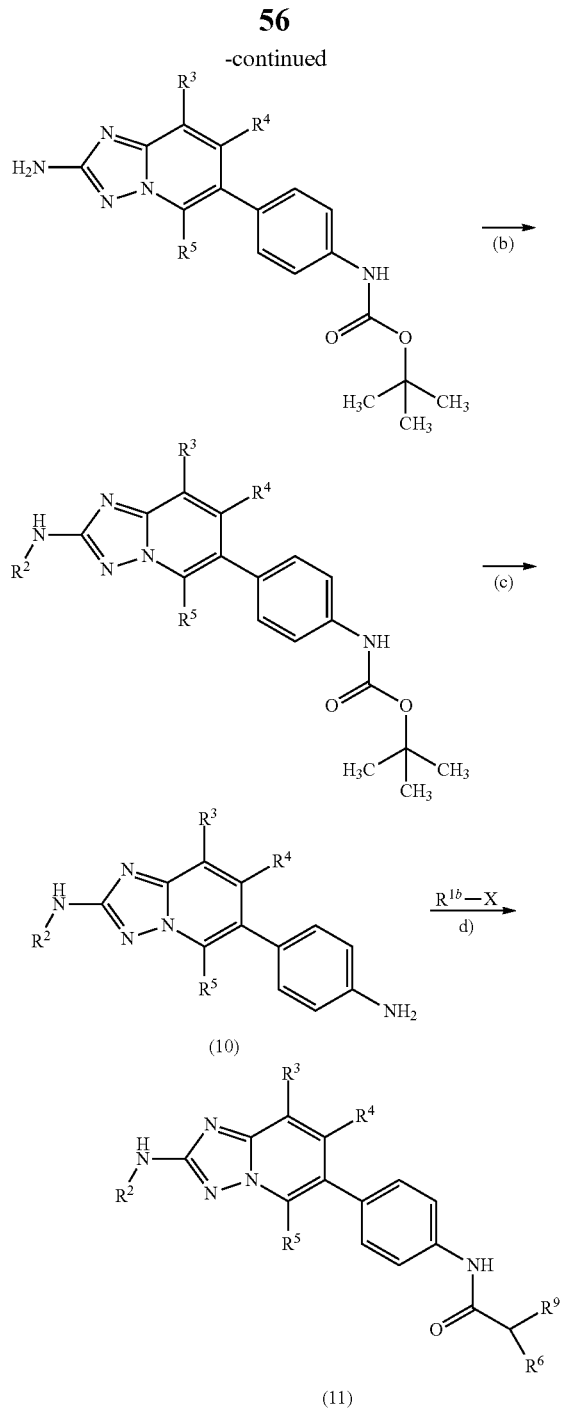

Scheme 2: Synthesis of compounds of general formula (11), wherein R$^2$, R$^3$, R$^4$, R$^5$ and R$^6$ are as defined for the compounds of general formula (I), supra. Y is a leaving group, e.g. a halogen.

R$^9$ represents a group selected from: C$_1$-C$_3$-alkyl-, hydroxy-C$_1$-C$_3$-alkyl-, —N(H)R$^8$, —N(R$^7$)R$^8$, N(H)(R$^8$)—C$_1$-C$_3$-alkyl-, N(R$^7$)(R$^8$)—C$_1$-C$_3$-alkyl-, PG$^1$-O—C$_1$-C$_3$-alkyl-, —N(PG$^2$)R$^8$, N(PG$^2$)(R$^8$)—C$_1$-C$_3$-alkyl-.

a) coupling reaction using conditions as described herein for synthesis of intermediates of general formula (6);
b) coupling reaction using conditions as described herein for synthesis of intermediates of general formula (7);
c) removal of a Boc-protecting group using conditions known to the person skilled in the art (see for example T. W.

Greene and P. G. M. Wuts in *Protective Groups in Organic Synthesis*, 3$^{rd}$ edition, Wiley 1999);

d) conditions for the formation of an amide bond, e.g. using coupling reagents like for example HATU or TBTU and a base like for example potassium carbonate, sodium bicarbonate or DIPEA in an inert solvent like for example THF, DMF, DCM, NMP or mixtures thereof. Optionally, the removal of a protecting group is included in step d) if R$^9$ represents PG$^1$-O—C$_1$-C$_3$-alkyl-, —N(PG$^2$)R$^8$, or N(PG$^2$) (R$^8$)—C$_1$-C$_3$-alkyl- (see for example T. W. Greene and P. G. M. Wuts in *Protective Groups in Organic Synthesis*, 3$^{rd}$ edition, Wiley 1999).

Preferably, in step d) a chiral compound of formula 7a:

R$^{1b}$—X  (7a)

in which R$^{1b}$ represents

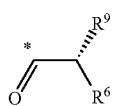

wherein * indicates the point of attachment of said group with the rest of the molecule; R$^9$ represents a group selected from:

C$_1$-C$_3$-alkyl-, hydroxy-C$_1$-C$_3$-alkyl-, —N(H)R$^8$; —N(R$^7$)R$^8$, N(H)(R$^8$)—C$_1$-C$_3$-alkyl-, N(R$^7$)(R$^8$)—C$_1$-C$_3$-alkyl-, PG$^1$-O—C$_1$-C$_3$-alkyl-, —N(PG$^2$)R$^8$, N(PG$^2$)(R$^8$)—C$_1$-C$_3$-alkyl-; and R$^6$, R$^7$ and R$^8$ are as defined for the compounds of general formula (I), supra, and X represents a suitable functional group (e.g. an —OH or —O—C$_1$-C$_6$-alkyl group, or a halogen atom), via which the R$^{1b}$ group of R$^{1b}$—X can be coupled, via a coupling reaction onto the —NH$_2$ substituent bound to the phenyl group of R$^{1a}$, thus providing a compound of general formula (I), supra, is used for the formation of the amide bond.

Otherwise, a separation step may be required in order to separate the desired chiral compound of formula (I) from its respective antipode.

Scheme 3: Synthesis of compounds of general formula (11)

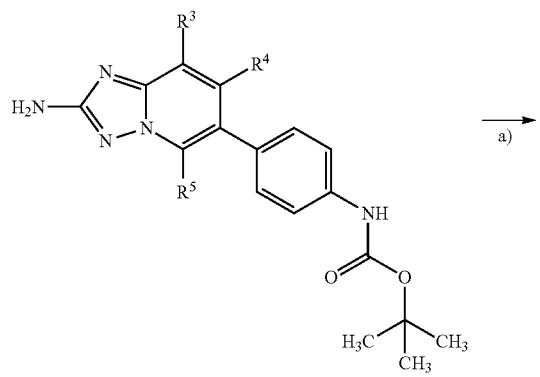

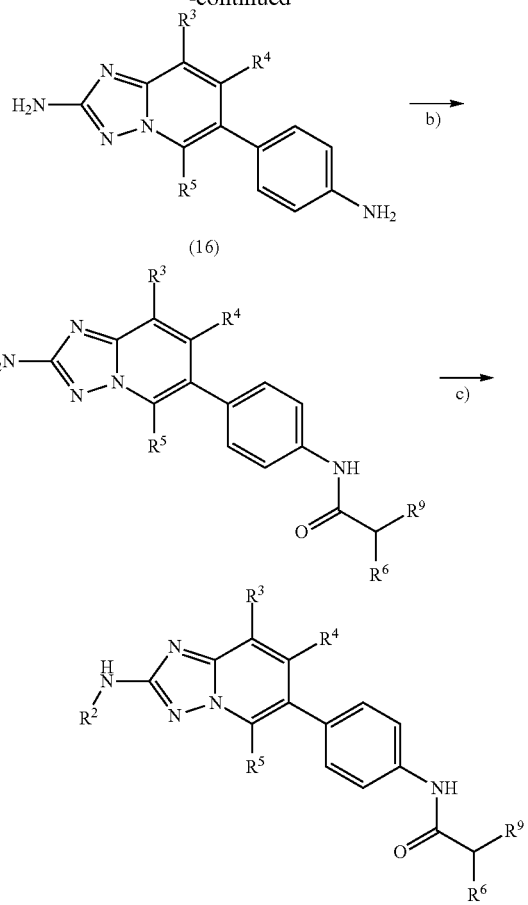

Scheme 3: Synthesis of compounds of general formula (11), wherein

R$^9$ represents a group selected from: C$_1$-C$_3$-alkyl-, hydroxy-C$_1$-C$_3$-alkyl-, —N(H)R$^8$, —N(R$^7$)R$^8$, N(H)(R$^8$)—C$_1$-C$_3$-alkyl-, N(R$^7$)(R$^8$)—C$_1$-C$_3$-alkyl-, PG$^1$-O—C$_1$-C$_3$-alkyl-, —N(PG$^2$)R$^8$, N(PG$^2$)(R$^8$)—C$_1$-C$_3$-alkyl-; and R$^2$, R$^3$, R$^4$, R$^5$, R$^6$, R$^7$, and R$^8$ are as defined for the compounds of general formula (I), supra.

a) removal of a Boc-protecting group using conditions known to the person skilled in the art (see for example T. W. Greene and P. G. M. Wuts in *Protective Groups in Organic Synthesis*, 3$^{rd}$ edition, Wiley 1999);

b) conditions for the formation of an amide bond, e.g. using coupling reagents like for example HATU or TBTU and a base like for example potassium carbonate, sodium bicarbonate or DIPEA in an inert solvent like for example THF, DMF, DCM, NMP or mixtures thereof;

c) coupling reaction using conditions as described supra for synthesis of intermediates of general formula (4). Optionally, the removal of a protecting group is included in step c) if R$^9$ represents PG$^1$-O—C$_1$-C$_3$-alkyl-, —N(PG$^2$)R$^8$, or N(PG$^2$)(R$^8$)—C$_1$-C$_3$-alkyl- (see for example T. W. Greene and P. G. M. Wuts in *Protective Groups in Organic Synthesis*, 3$^{rd}$ edition, Wiley 1999).

Preferably, steps b) and c) are performed with achiral compounds and a separation of the desired chiral compound of formula (I) from its respective antipode is conducted after the coupling reaction according to step c).

The compounds and intermediates produced according to the methods of the invention may require purification.

Purification of organic compounds is well known to the person skilled in the art and there may be several ways of purifying the same compound. In some cases, no purification may be necessary. In some cases, the compounds may be purified by crystallisation. In some cases, impurities may be stirred out using a suitable solvent. In some cases, the compounds may be purified by chromatography, particularly flash chromatography, using for example pre-packed silica gel cartridges, e.g. from Separtis such as Isolute® Flash silica gel (silica gel chromatography) or Isolute® Flash NH2 silica gel (aminophase-silica-gel chromatography) in combination with a suitable chromatographic system such as a Flashmaster II (Separtis) or an Isolera system (Biotage) and eluents such as, for example, gradients of hexane/ethyl acetate or DCM/methanol. In some cases, the compounds may be purified by preparative HPLC using, for example, a Waters autopurifier equipped with a diode array detector and/or on-line electrospray ionisation mass spectrometer in combination with a suitable pre-packed reverse phase column and eluants such as, for example, gradients of water and acetonitrile which may contain additives such as trifluoroacetic acid, formic acid or aqueous ammonia.

Analytical UPLC-MS was performed as follows:
Method A: System: UPLC Acquity (Waters) with PDA Detector and Waters ZQ mass spectrometer; Column: Acquity BEH C18 1.7 μm 2.1×50 mm; Temperature: 60° C.; Solvent A: Water+0.1% formic acid; Solvent B: acetonitrile; Gradient: 99% A→1% A (1.6 min)→1% A (0.4 min); Flow: 0.8 mL/min; Injection Volume: 1.0 μl (0.1 mg-1 mg/mL sample concentration); Detection: PDA scan range 210-400 nm—Fixed and ESI (+), scan range 170-800 m/z Synthesis of Intermediate Compounds Intermediate Example Int01.01

Ethyl [(5-bromopyridin-2-yl)carbamothioyl]carbamate

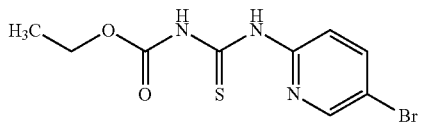 [SMILES: CCOC(=O)NC(=S)Nc1ccc(Br)cn1]

Ethoxycarbonylisothiocyanat (16.7 g) was added to a stirred solution of 2-amino-5-bromopyridine (20 g) in dioxane (200 mL). The mixture was stirred for 2 h at r.t. A white solid precipitated. Hexane (20 mL) was added and the white solid was collected by filtration.

Yield: 30.4 g of the title compound.
$^1$H-NMR (300 MHz, DMSO-d$_6$): δ [ppm]=1.22 (t, 3H), 4.19 (q, 2H), 8.08 (dd, 1H), 8.49 (d, 1H), 8.57 (br. d, 1H), 11.37-12.35 (m, 2H).

Intermediate Example Int01.02

6-Bromo[1,2,4]triazolo[1,5-a]pyridin-2-amine

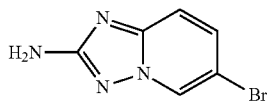 [SMILES: Nc1nc2ccc(Br)cn2n1]

Hydroxylammoniumchlorid (39.8 g) was suspended in methanol (200 mL) and ethanol (190 mL) and Hünig Base (59 mL) was added at r.t. The mixture was heated to 60° C., Int01.01 (30 g) was added portionwise, and the mixture was stirred at 60° C. for 2 h. The solvent was removed in vacuum and water (150 mL) was added. A solid was collected by filtration and was washed with water and dried in vacuum.

Yield: 19.3 g of the title compound.
$^1$H-NMR (300 MHz, DMSO-d$_6$): δ [ppm]=6.10 (s, 2H), 7.28 (dd, 1H), 7.51 (dd, 1H), 8.88 (dd, 1H).

Intermediate Example Int01.03 tert-butyl [4-(2-amino[1,2,4]triazolo[1,5-a]pyridin-6-yl)phenyl]carbamate

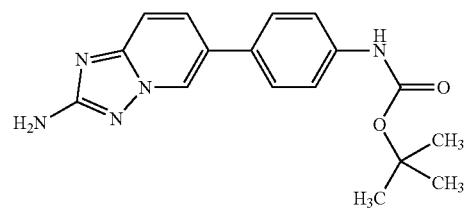 [SMILES: CC(C)(C)OC(=O)Nc1ccc(-c2ccc3nc(N)nn3c2)cc1]

To a stirred solution of Int01.02 (5.82 g) in 1-propanol (400 mL) was added 2M potassium carbonate solution (41 mL), {4-[(tert-butoxycarbonyl)amino]phenyl}boronic acid (8.6 g), triphenylphosphine (150 mg) and PdCl$_2$(PPh$_3$)$_2$ (1.9 g). The mixture was heated to reflux for 4 h, the solvent was removed in vacuum, water (150 mL) was added and the mixture was extracted with ethyl acetate (500 mL). The organic phase was dried (sodium sulfate), filtered through Celite and the solvent was removed in vacuum. The residue was triturated with DCM to give the title compound as a white solid. Yield: 7.2 g.
$^1$H-NMR (400 MHz, DMSO-d$_6$): δ [ppm]=1.37-1.55 (m, 9H), 5.99 (s, 2H), 7.36 (dd, 1H), 7.48-7.55 (m, 2H), 7.55-7.62 (m, 2H), 7.69 (dd, 1H), 8.78 (dd, 1H), 9.44 (s, 1H).

Intermediate Example Int01.04

6-(4-aminophenyl)[1,2,4]triazolo[1,5-a]pyridin-2-amine

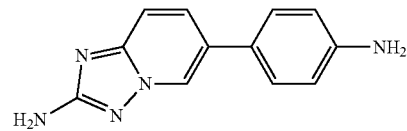 [SMILES: Nc1ccc(-c2ccc3nc(N)nn3c2)cc1]

To a stirred suspension of Int01.03 (7.05 g) in DCM (210 mL) was added TFA (66 mL). The mixture was stirred at r.t. for 1 h. The mixture was concentrated in vacuum. A saturated solution of potassium carbonate was added, until pH 10 was reached and the mixture was extracted for three times with DCM and methanol (10:1). The organic phase was dried (sodium sulfate) and the solvent was removed in vacuum to give 4.6 g of the title compound.
$^1$H-NMR (300 MHz, DMSO-d$_6$): δ [ppm]=5.26 (s, 2H), 5.95 (s, 2H), 6.64 (d, 2H), 7.29-7.45 (m, 3H), 7.64 (dd, 1H), 8.60-8.70 (m, 1H).

Intermediate Example Int01.05

N-[4-(2-amino[1,2,4]triazolo[1,5-a]pyridin-6-yl)phenyl]-2-(4-fluorophenyl)propanamide

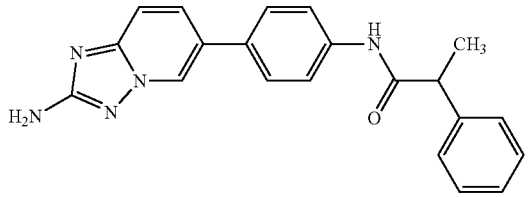 [SMILES: CC(C(=O)Nc1ccc(-c2ccc3nc(N)nn3c2)cc1)c1ccccc1]

To a stirred solution of Int01.04 (3.80 g) in DMF (350 mL) was added potassium carbonate (11.6 g), Int09.02 (5.67 g) and HATU (12.8 g). The mixture was stirred at room temperature for 2 h. Water was added, the mixture was stirred for 15 minutes and the mixture was extracted with ethyl acetate. The organic phase was washed with saturated sodium chloride solution, dried (sodium sulfate) and the solvent was removed in vacuum. The crude product was triturated with ethyl acetate to give 4.07 g of the title compound.

$^1$H-NMR (400 MHz, DMSO-d$_6$): δ [ppm]=1.39 (d, 3H), 3.83 (q, 1H), 5.98 (s, 2H), 7.08-7.17 (m, 2H), 7.32-7.44 (m, 3H), 7.60-7.67 (m, 4H), 7.70 (dd, 1H), 8.79 (d, 1H), 10.13 (s, 1H).

Intermediate Example Int02.01 methyl 4-bromo-3-methoxybenzoate

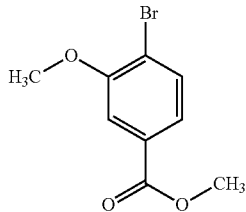

To a stirred solution of methyl 4-bromo-3-hydroxybenzoate (10.0 g) in DMF (50 mL) was added potassium carbonate (17.9 g) and iodomethane (9.2 mg). The mixture was stirred at room temperature for 2 h. Ethyl acetate was added and the mixture was washed with water. The organic phase was washed with saturated sodium chloride solution, dried (sodium sulfate) and the solvent was removed in vacuum to give 10 g of the title compound, that was used without further purification.

$^1$H-NMR (400 MHz, DMSO-d$_6$): δ [ppm]=3.82 (s, 3H), 3.87 (s, 3H), 7.41 (dd, 1H), 7.47 (d, 1H), 7.67 (d, 1H).

Intermediate Example Int02.02

4-bromo-3-methoxybenzoic acid

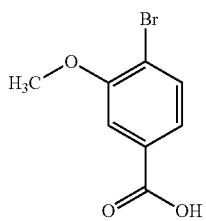

To a stirred solution of methyl 4-bromo-3-methoxybenzoate (11.2 g) in THF (130 mL), methanol (45 mL) and water (45 mL) was added a 1 M solution of lithium hydroxide in water (140 mL). The mixture was stirred at room temperature for 1 h. The solvent was removed in vacuum. Water was added and 1 N hydrochloric acid was added with ice bath cooling until pH 4 was reached. The precipitated solid was collected by filtration, washed with water and dried in vacuum to give 10.1 g of the title compound, that was used without further purification.

$^1$H-NMR (300 MHz, DMSO-d$_6$): δ [ppm]=3.87 (s, 3H), 7.42 (dd, 1H), 7.50 (d, 1H), 7.68 (d, 1H), 13.21 (br. s., 1H).

Intermediate Example Int02.03

4-bromo-3-methoxy-N-(2,2,2-trifluoroethyl)benzamide

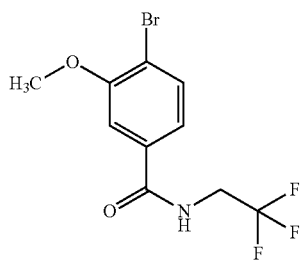 [SMILES: COc1cc(C(=O)NCC(F)(F)F)ccc1Br]

To a stirred suspension of 4-bromo-3-methoxybenzoic acid (2.0 g) in THF (100 mL) was added 2,2,2-trifluoroethylamine (1.26 g), HATU (3.87 g), and DIPEA (1.7 ml). The mixture was stirred at room temperature for 12 h. Water (350 ml) and saturated sodium bicarbonate solution (350 ml) were added. The organic phase was separated and the aqueous phase was extracted with ethyl acetate. The combined organic extracts were dried (sodium sulfate) and the solvent was removed in vacuum. Silica gel chromatography gave 2.57 g of the title compound.

$^1$H-NMR (400 MHz, DMSO-d$_6$): δ [ppm]=3.92 (s, 3H), 4.11 (qd, 2H), 7.43 (dd, 1H), 7.56 (d, 1H), 7.72 (d, 1H), 9.19 (t, 1H).

Intermediate Example Int02.04 azetidin-1-yl(4-bromo-3-methoxyphenyl)methanone

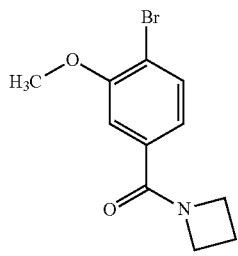

To a stirred solution of 4-bromo-3-methoxybenzoic acid (400 mg) in DMF (4.0 mL) was added potassium carbonate (720 mg), azetidine (148 mg) and TBTU (890 mg). The mixture was stirred at room temperature for 60 h. Water was added, the mixture was stirred for 15 minutes and the solvent was removed in vacuum. Water was added and the mixture was extracted with ethyl acetate. The organic phase was washed with saturated sodium chloride solution, dried (sodium sulfate) and the solvent was removed in vacuum. Silica gel chromatography gave 370 mg of the title compound.

$^1$H-NMR (400 MHz, DMSO-d$_6$): δ [ppm]=2.15-2.27 (m, 2H), 3.85 (s, 3H), 4.00 (t, 2H), 4.26 (t, 2H), 7.07 (dd, 1H), 7.21 (d, 1H), 7.61 (d, 1H).

Intermediate Example Int02.05

(4-Bromo-3-methoxyphenyl)(3-fluoroazetidin-1-yl)methanone

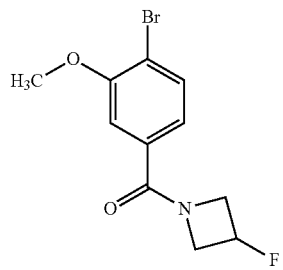 [SMILES: COc1cc(C(=O)N2CC(F)C2)ccc1Br]

To a stirred solution of 4-bromo-3-methoxybenzoic acid (1.4 g) in DMF (15 mL) was added potassium carbonate (2.51 g), 3-fluoroazetidine hydrochloride (1.01 g) and HATU (3.69 g). The mixture was stirred at room temperature for 18 h. Water was added, the mixture was stirred for 15 minutes and the solvent was removed in vacuum. Water was added and the mixture was extracted with ethyl acetate. The organic phase was washed with water, saturated sodium chloride solution, dried (sodium sulfate) and the solvent was removed in vacuum, to give 1.25 g of the title compound.

$^1$H-NMR (400 MHz, DMSO-d$_6$): δ [ppm]=3.90 (s, 3H), 3.99-4.16 (m, 1H), 4.31-4.65 (m, 3H), 5.36 (tt, 0.5H), 5.50 (tt, 0.5H), 7.14 (dd, 1H), 7.26 (d, 1H), 7.66 (d, 1H).

Intermediate Example Int02.06

4-bromo-3-methoxy-N,N-dimethylbenzamide

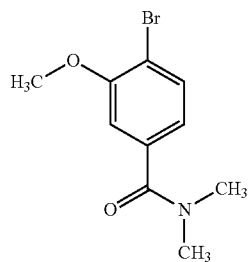

Starting with 4-bromo-3-methoxybenzoic acid and dimethyl amine, Int02.06 was prepared analogously to the procedure for the preparation of Int02.05.

Intermediate Example Int02.07

(4-bromo-3-methoxyphenyl)(pyrrolidin-1-yl)methanone

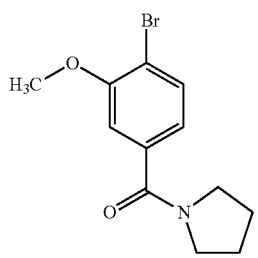 [SMILES: COc1cc(C(=O)N2CCCC2)ccc1Br]

Starting with 4-bromo-3-methoxybenzoic acid and pyrrolidin, Int02.07 was prepared analogously to the procedure for the preparation of Int02.04.

Intermediate Example Int03.01

1-bromo-2-methoxy-4-(methylsulfanyl)benzene

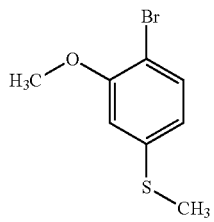

To a stirred solution of 1-bromo-4-fluoro-2-methoxybenzene (4.0 g) in DMF (40 mL) was added sodium methanethiolate (2.76 g). The mixture was stirred at room temperature for 30 minutes and at 85° C. for 2 h. Water was added and the mixture was extracted with ethyl acetate. The organic phase was washed with saturated sodium chloride solution, dried (sodium sulfate) and the solvent was removed in vacuum. Silica gel chromatography gave 280 mg of the title compound.

$^1$H-NMR (400 MHz, DMSO-d$_6$): δ [ppm]=2.46 (s, 3H), 3.82 (s, 3H), 6.74 (dd, 1H), 6.91 (d, 1H), 7.44 (d, 1H).

1-bromo-2-methoxy-4-(methylsulfanyl)benzene

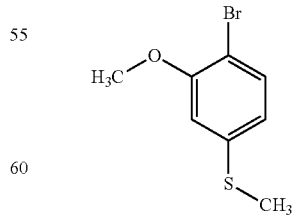

To a stirred solution of 1-bromo-4-fluoro-2-methoxybenzene (10.0 g) in DMF (100 mL) was added sodium methanethiolate (4.44 g). The mixture was stirred at 65° C. for 2 h. The mixture was cooled to 0° C. and methyl iodide (4.55 mL) was added. The mixture was stirred at room temperature for 1 h and further sodium methanethiolate (4.44 g) was added. The mixture was stirred at 65° C. for 1 h. The mixture was cooled to 0° C. and methyl iodide (4.55 mL) was added. The mixture was stirred at room temperature for 1 h. Water was added and the mixture was extracted with ethyl acetate. The organic phase was washed with saturated sodium chloride solution, dried (sodium sulfate) and the solvent was removed in vacuum. Silica gel chromatography gave 6.2 g of the title compound as a 2:1 mixture with the starting material. The mixture was used for the next step without purification.

Intermediate Example Int03.02

1-bromo-2-methoxy-4-(methylsulfonyl)benzene

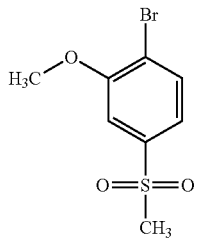

To a stirred solution of Int03.01 (265 mg) in chloroform (10 mL) was added 3-chlorobenzenecarboperoxoic acid (mCPBA) (890 mg). The mixture was stirred at room temperature for 1 h. A half-saturated solution of sodium bicarbonate was added and the mixture was extracted with dichloromethane. The organic phase was washed with saturated sodium chloride solution, dried (sodium sulfate) and the solvent was removed in vacuum. Silica gel chromatography gave 252 mg of the title compound.

$^1$H-NMR (300 MHz, DMSO-$d_6$): δ [ppm]=3.22 (s, 3H), 3.93 (s, 3H), 7.39 (dd, 1H), 7.50 (d, 1H), 7.84 (d, 1H).

Intermediate Example Int04.01

1-bromo-2-ethoxy-4-fluorobenzene

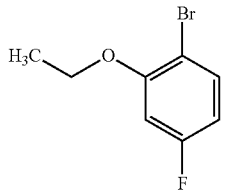

To a stirred solution of 2-bromo-5-fluorophenol (5.0 g) in DMF (30 mL) was added potassium carbonate (10.8 g) and iodoethane (6.12 g). The mixture was stirred at room temperature for 16 h. The solvent was removed in vacuum. Water was added and the mixture was extracted with a mixture of ethyl acetate and hexane (3:1). The organic phase was washed with saturated sodium chloride solution, dried (sodium sulfate) and the solvent was removed in vacuum, to give 5.06 g of th title compound as a crude product, that was used for the next step without purification.

$^1$H-NMR (400 MHz, DMSO-$d_6$): δ [ppm]=1.31 (t, 3H), 4.08 (q, 2H), 6.71 (td, 1H), 7.00 (dd, 1H), 7.55 (dd, 1H).

Intermediate Example Int04.02

1-bromo-2-ethoxy-4-(methylsulfanyl)benzene

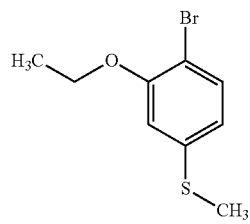

To a stirred solution of 1-bromo-2-ethoxy-4-fluorobenzene (2.0 g) in DMF (20 mL) was added sodium methanethiolate (1.66 g). The mixture was stirred for 2 h at 65° C. The mixture was cooled to room temperature and ethyl iodide (1.3 mL) was added. The mixture was stirred at room temperature for 1 h. Water was added and the mixture was extracted with ethyl acetate. The organic phase was washed with saturated sodium chloride solution, dried (sodium sulfate) and the solvent was removed in vacuum. Silica gel chromatography gave 1.65 g of the title compound.

$^1$H-NMR (400 MHz, DMSO-$d_6$): δ [ppm]=1.24-1.36 (m, 3H), 2.45 (s, 3H), 4.08 (q, 2H), 6.73 (dd, 1H), 6.89 (d, 1H), 7.43 (d, 1H).

Intermediate Example Int04.03

1-bromo-2-ethoxy-4-(methylsulfonyl)benzene

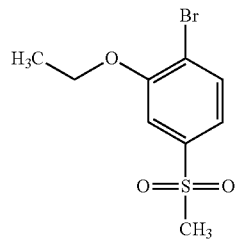

To a stirred solution of Int04.02 (1.65 g) in chloroform (65 mL) was added 3-chlorobenzenecarboperoxoic acid (mCPBA) (4.49 g). The mixture was stirred at room temperature for 16 h. With ice bath cooling, a half-saturated solution of sodium bicarbonate and a 0.2 M solution of sodium thiosulfate was added, the mixture was stirred for 30 minutes and the mixture was extracted with dichloromethane. The organic phase was washed with saturated sodium chloride solution, dried (sodium sulfate) and the solvent was removed in vacuum. Silica gel chromatography gave 1.35 g of the title compound.

$^1$H-NMR (300 MHz, DMSO-$d_6$): δ [ppm]=1.35 (t, 3H), 3.22 (s, 3H), 4.20 (q, 2H), 7.37 (dd, 1H), 7.48 (d, 1H), 7.84 (d, 1H).

Intermediate Example Int05.01

1-bromo-4-fluoro-2-(2,2,2-trifluoroethoxyl)benzene

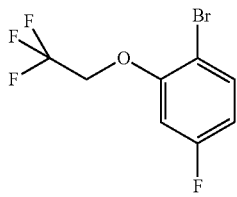 [SMILES: Fc1ccc(Br)c(OCC(F)(F)F)c1]

To a stirred solution of 2-bromo-5-fluorophenol (1.5 g) in acetonitrile (0.5 mL) and DMF (8.5 mL) in a microwave tube was added potassium carbonate (2.1 g) and 2,2,2-trifluoroethyl trifluoromethanesulfonate (2.37 g). The mixture was heated to 150° C. in a microwave oven for 30 minutes. In a second microwave tube the same reaction was repeated. Both mixtures were combined. The solvent was removed in vacuum, ethyl acetate and hexane (1:1) was added and the mixture was washed with water. The organic phase was washed with saturated sodium chloride solution, dried (sodium sulfate) and the solvent was removed in vacuum. Silica gel chromatography gave 4.0 g of the title compound.

$^1$H-NMR (300 MHz, CHLOROFORM-d): δ [ppm]=4.39 (q, 2H), 6.62-6.78 (m, 2H), 7.53 (dd, 1H).

Intermediate Example Int05.02

1-bromo-4-(methylsulfanyl)-2-(2,2,2-trifluoroethoxyl)benzene

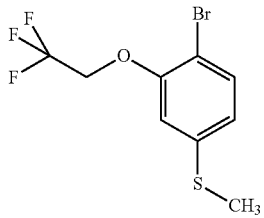

To a stirred solution of Int05.01 (4.0 g) in DMF (15 mL) was added sodium methanethiolate (1.0 g). The mixture was stirred for 2 h at 60° C. The mixture was cooled to room temperature. Water was added and the mixture was extracted with ethyl acetate. The organic phase was washed with saturated sodium chloride solution, dried (sodium sulfate) and the solvent was removed in vacuum to give 3.8 g of the crude title compound, that was used for the next step without purification.

$^1$H-NMR (300 MHz, CHLOROFORM-d): δ [ppm]=2.48 (s, 3H), 4.39 (q, 2H), 6.78-6.88 (m, 2H), 7.46 (d, 1H).

Intermediate Example Int05.03

1-bromo-4-(methylsulfonyl)-2-(2,2,2-trifluoroethoxyl)benzene

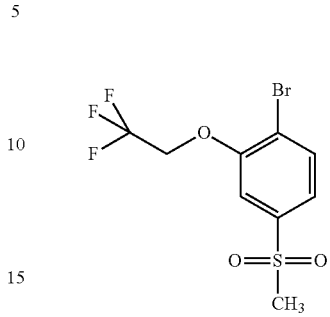

To a stirred solution of Int05.02 (3.8 g) in chloroform (100 mL) was added 3-chlorobenzenecarboperoxoic acid (mCPBA) (8.48 g). The mixture was stirred at room temperature for 16 h. With ice bath cooling, a half-saturated solution of sodium bicarbonate and a 0.2 M solution of sodium thiosulfate was added, the mixture was stirred for 30 minutes and the mixture was extracted with dichloromethane. The organic phase was washed with a 0.2 M solution of sodium thiosulfate and a saturated sodium chloride solution, dried (sodium sulfate) and the solvent was removed in vacuum. Silica gel chromatography gave a solid that was triturated with ether to give 2.1 g of the title compound.

$^1$H-NMR (400 MHz, CHLOROFORM-d): δ [ppm]=3.06 (s, 3H), 4.50 (q, 2H), 7.45 (d, 1H), 7.52 (dd, 1H), 7.81 (d, 1H).

Intermediate Example Int06.01 methyl 4-bromo-3-(2,2,2-trifluoroethoxyl)benzoate

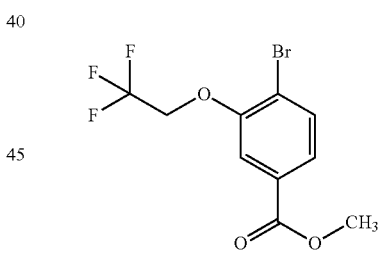

To a stirred solution of methyl 4-bromo-3-hydroxybenzoate (2.5 g) in acetonitrile (0.5 mL) and DMF (10 mL) in a microwave tube was added potassium carbonate (2.93 g) and 2,2,2-trifluoroethyl trifluoromethane-sulfonate (2.79 g). The mixture was heated to 150° C. in a microwave oven for 30 minutes. The solvent was removed in vacuum, ethyl acetate was added and the mixture was washed with water. The organic phase was washed with saturated sodium chloride solution, dried (sodium sulfate) and the solvent was removed in vacuum. Recrystallization of the residue from ethanol gave 1.2 g of the title compound. The mother liquor was concentrated in vacuum and purified by aminophase-silica-gel chromatography followed by recrystallized from methanol and water to give further 0.64 g of the title compound.

$^1$H-NMR (300 MHz, CHLOROFORM-d): δ [ppm]=3.93 (s, 3H), 4.47 (q, 2H), 7.56 (d, 1H), 7.58-7.70 (m, 2H).

Intermediate Example Int06.02

4-bromo-3-(2,2,2-trifluoroethoxyl)benzoic acid

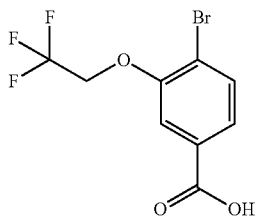 [SMILES: O=C(O)c1ccc(Br)c(OCC(F)(F)F)c1]

To a stirred solution of Int06.01 (1.83 g) in THF (30 mL), methanol (10 mL) and water (10 mL) was added a 1 M solution of lithium hydroxide in water (18 mL). The mixture was stirred at room temperature for 1 h. Water was added and 2 N hydrochloric acid was added until pH 4 was reached. The precipitated solid was collected by filtration, was washed with water. The solid was suspended with toluene and concentrated in vacuum. Trituration of the residue with hexane gave 1.6 g of the title compound.

$^1$H-NMR (300 MHz, DMSO-$d_6$): δ [ppm]=4.95 (q, 2H), 7.51 (dd, 1H), 7.65 (d, 1H), 7.74 (d, 1H), 13.29 (br. s., 1H).

Intermediate Example Int06.03

4-bromo-3-(2,2,2-trifluoroethoxyl)benzamide

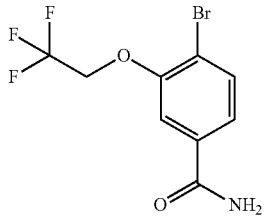 [SMILES: NC(=O)c1ccc(Br)c(OCC(F)(F)F)c1]

To a stirred suspension of Int06.02 (0.50 g) in THF (20 mL) was added DMF (0.2 mL) and oxalyl chloride (0.30 mL). The mixture was stirred at room temperature for 0.5 h. With ice bath cooling, ammonia gas was bubbled through the reaction mixture. A white solid precipitated. The mixture was stirred for further 15 minutes. Ethyl acetate was added and the mixture was washed with water and with a saturated solution of sodium chloride. The organic phase was dried (sodium sulfate) and the solvent was removed in vacuum to give a white solid. The solid was triturated with toluene and washed with toluene and hexanes to give 0.27 g of the title compound.

$^1$H-NMR (300 MHz, DMSO-$d_6$): δ [ppm]=4.88 (q, 2H), 7.45 (dd, 1H), 7.50 (br. s., 1H), 7.64 (d, 1H), 7.69 (d, 1H), 8.00 (br. s., 1H).

Intermediate Example Int06.04

[4-bromo-3-(2,2,2-trifluoroethoxy)phenyl](3-fluoro-azetidin-1-yl)methanone

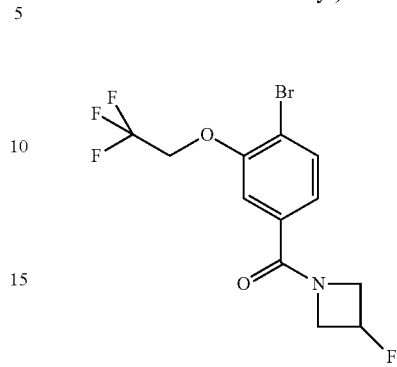

Starting with 4-bromo-3-(2,2,2-trifluoroethoxyl)benzoic acid and 3-fluoroazetidine hydrochloride, Int06.04 was prepared analogously to the procedure for the preparation of Int02.06.

Intermediate Example Int06.05

[4-bromo-3-(2,2,2-trifluoroethoxy)phenyl](3-hydroxyazetidin-1-yl)methanone

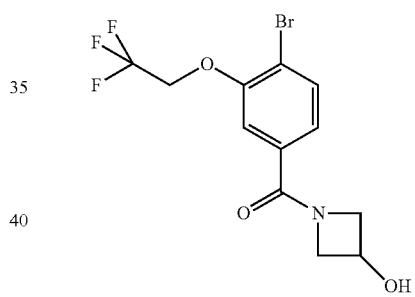

Starting with 4-bromo-3-(2,2,2-trifluoroethoxy)benzoic acid and azetidin-3-ol hydrochloride, Int06.05 was prepared analogously to the procedure for the preparation of Int02.03.

Intermediate Example Int06.06

[4-bromo-3-(2,2,2-trifluoroethoxy)phenyl](pyrrolidin-1-yl)methanone

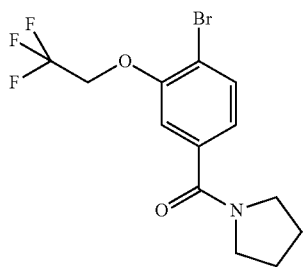 [SMILES: O=C(c1ccc(Br)c(OCC(F)(F)F)c1)N1CCCC1]

Starting with 4-bromo-3-(2,2,2-trifluoroethoxy)benzoic acid and pyrrolidin, Int06.06 was prepared analogously to the procedure for the preparation of Int02.05.

Intermediate Example Int07.01

3-(4-bromo-3-methoxyphenyl)-1,3-oxazolidin-2-one

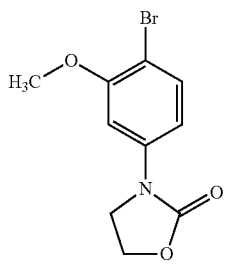

To a stirred solution of 4-Bromo-3-methoxy-aniline (10.0 g) in acetonitrile (176 mL) was added Hünig Base (25 mL) and 2-chloroethyl chloroformate (10.6 g). The mixture was stirred at room temperature for 0.5 h. The solvent was removed in vacuum. The residue was dissolved in tetrahydrofurane (250 mL), and potassium tert-butoxide (16.2 g) was added. The mixture was stirred at room temperature for 2 h. The solvent was removed in vacuum. The residue was dissolved in ethyl acetate and the mixture was washed with water and with saturated sodium chloride solution, dried (sodium sulfate) and the solvent was removed in vacuum. Silica gel chromatography gave a compound that was crystallized from ethanol. Yield: 7.7 g of the title compound. The mother liquor was concentrated in vacuum and aminophase-silica-get chromatography gave a solid that was recrystallized from ethanol to give further 2.3 g of the title compound.

$^1$H-NMR (300 MHz, CHLOROFORM-d): δ [ppm]=4.00-4.10 (m, 2H), 4.45-4.55 (m, 2H), 6.66 (dd, 1H), 7.49 (d, 1H), 7.63 (d, 1H).

Intermediate Example Int08.010 tert-butyl [4-(2-{[2-methoxy-4-(methylsulfonyl)phenyl]amino}[1,2,4]-triazolo[1,5-a]pyridin-6-yl)phenyl]carbamate

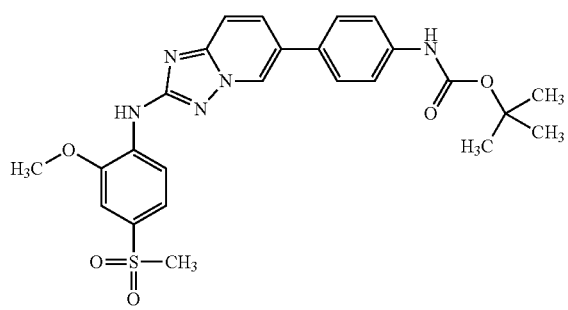 [SMILES: COc1cc(S(C)(=O)=O)ccc1Nc1nc2ccc(-c3ccc(NC(=O)OC(C)(C)C)cc3)cn2n1]

To a stirred suspension of Int01.03 (4.0 g) in toluene (250 mL) and NMP (25 mL) was added Int03.02 (8.31 g), chloro(2-dicyclohexylphosphino-2',4',6'-tri-isopropyl-1,1'-biphenyl)[2-(2-aminoethyl)phenyl] palladium(II) methyl-tert-butylether adduct (1.08 g), X-Phos (0.64 g) and powdered potassium phosphate (16.6 g). The flask was twice degassed and backfilled with argon. The mixture was heated to reflux for 16 h.

The reaction mixture was filtered through a microfilter and the solvent was removed in vacuum. The residue was triturated with dichloromethane to give 12.3 g of the title compound.

$^1$H-NMR (400 MHz, DMSO-d$_6$): δ [ppm]=1.46 (s, 9H), 3.16 (s, 3H), 3.96 (s, 3H), 7.43 (d, 1H), 7.48-7.59 (m, 3H), 7.63-7.72 (m, 3H), 7.92 (dd, 1H), 8.48 (d, 1H), 8.58 (s, 1H), 9.06-9.12 (m, 1H), 9.46 (s, 1H).

Intermediate Example Int08.011

6-(4-aminophenyl)-N-[2-methoxy-4-(methylsulfonyl)phenyl][1,2,4]-triazolo[1,5-a]pyridin-2-amine

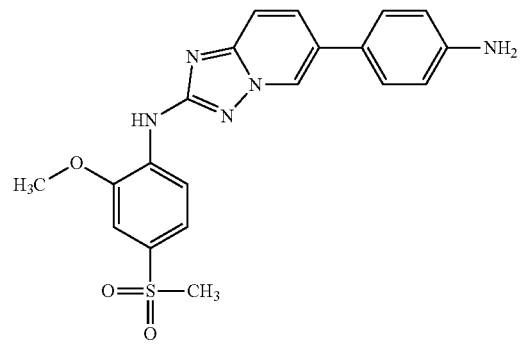 [SMILES: COc1cc(S(C)(=O)=O)ccc1Nc1nc2ccc(-c3ccc(N)cc3)cn2n1]

To a stirred suspension of Int08.010 (12.3 g) in dichloromethane (40 mL) was added TFA (46 mL). The mixture was stirred at room temperature for 16 h. Further TFA was added (1 mL) and the mixture was stirred at room temperature for 5 h. A saturated solution of potassium carbonate was added until pH 9 was reached. The mixture was extracted with dichloromethane and methanol (10:1 mixture). The solution was dried (sodium sulfate) and the solvent was removed in vacuum. The residue was triturated with ethanol to give 9.2 g of the title compound.

$^1$H-NMR (300 MHz, DMSO-d$_6$): δ [ppm]=3.16 (s, 3H), 3.95 (s, 3H), 5.30 (s, 2H), 6.63 (d, 2H), 7.38-7.46 (m, 3H), 7.51 (dd, 1H), 7.61 (d, 1H), 7.84 (dd, 1H), 8.48 (d, 1H), 8.55 (s, 1H), 8.93 (d, 1H).

Intermediate Example Int08.020 tert-butyl [4-(2-{[4-(methylsulfonyl)-2-(2,2,2-trifluoroethoxy)phenyl]-amino}[1,2,4]triazolo[1,5-a]pyridin-6-yl)phenyl]carbamate

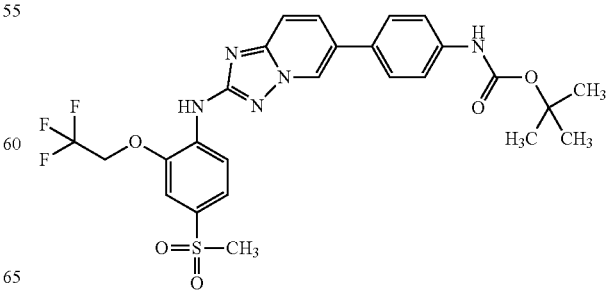

To a stirred suspension of Int01.03 (4.0 g) in toluene (77 mL) and NMP (7.7 mL) was added Int05.03 (4.91 g), chloro(2-dicyclohexylphosphino-2',4',6'-triisopropyl-1,1'-biphenyl)[2-(2-aminoethyl)phenyl] palladium(II) methyl-tert-butylether adduct (254 mg) and X-Phos (150 mg) and the flask was twice degassed and backfilled with argon. The mixture was stirred for 5 minutes at room temperature. Powdered potassium phosphate (9.13 g) was added and the flask was twice degassed and backfilled with argon. The mixture was heated to reflux for 1 h. The reaction mixture was filtered through an aminophase-silica-gel column and the solvent was removed in vacuum. Aminophase-silica-gel chromatography gave a solid that was triturated with a mixture of hexane and dichloromethane to give 6.05 g of the title compound.

¹H-NMR (400 MHz, DMSO-d₆): δ [ppm]=1.46 (s, 9H), 3.17 (s, 3H), 5.00 (q, 2H), 7.55 (d, 2H), 7.60-7.71 (m, 5H), 7.93 (dd, 1H), 8.50 (d, 1H), 8.54 (s, 1H), 9.09 (dd, 1H), 9.46 (s, 1H).

Intermediate Example Int08.021

6-(4-aminophenyl)-N-[4-(methylsulfonyl)-2-(2,2,2-trifluoroethoxy)phenyl]-[1,2,4]triazolo[1,5-a]pyridin-2-amine

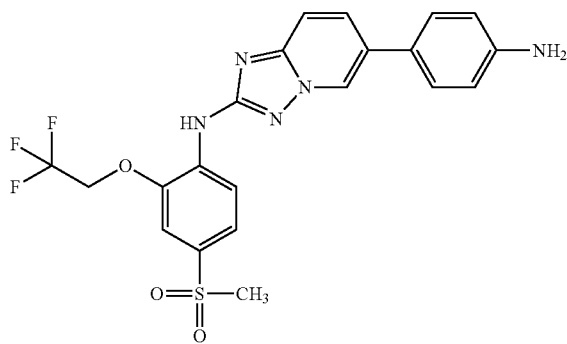 [SMILES: CS(=O)(=O)c1ccc(Nc2nc3ccc(-c4ccc(N)cc4)cn3n2)c(OCC(F)(F)F)c1]

To a stirred suspension of Int08.020 (11.9 g) in dichloromethane (80 mL) was added TFA (40 mL). The mixture was stirred at room temperature for 24 h. The solvent was removed in vacuum, and the residue was dissolved in ethyl acetate. A half-saturated solution of sodium bicarbonate was added until pH 9 was reached. The precipitated solid was collected by filtration to give 9.7 g of the title compound.

¹H-NMR (400 MHz, DMSO-d₆): δ [ppm]=3.16 (s, 3H), 5.00 (q, 2H), 5.34 (br. s., 2H), 6.60-6.68 (m, 2H), 7.39-7.48 (m, 2H), 7.57-7.66 (m, 3H), 7.85 (dd, 1H), 8.48 (s, 1H), 8.51 (d, 1H), 8.89-8.96 (m, 1H).

Intermediate Example Int08.030 tert-butyl {4-[2-({2-methoxy-4-[(2,2,2-trifluoroethyl)carbamoyl]phenyl}-amino)[1,2,4]triazolo[1,5-a]pyridin-6-yl]phenyl}carbamate

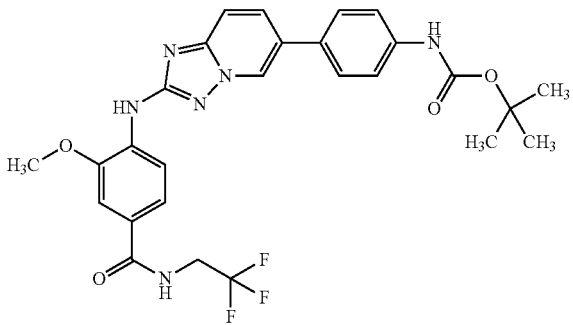 [SMILES: COc1cc(C(=O)NCC(F)(F)F)ccc1Nc1nc2ccc(-c3ccc(NC(=O)OC(C)(C)C)cc3)cn2n1]

To a stirred suspension of Int01.03 (500 mg) in toluene (10 mL) and NMP (0.5 mL) was added Int02.03 (576 mg), chloro(2-dicyclohexylphosphino-2',4',6'-tri-isopropyl-1,1'-biphenyl)[2-(2-aminoethyl)phenyl] palladium(II) methyl-tert-butylether adduct (64 mg), X-Phos (37 mg) and powdered potassium phosphate (1.14 g). The flask was twice degassed and backfilled with argon. The mixture was heated to reflux for 16 h. The solvent was removed in vacuum. Aminophase-silica-gel chromatography gave the title compound as a crude product (850 mg) that was used for the next step without further purification.

¹H-NMR (400 MHz, DMSO-d₆): δ [ppm]=1.46 (s, 9H), 3.93 (s, 3H), 4.01-4.15 (m, 2H), 7.51-7.60 (m, 4H), 7.62-7.71 (m, 3H), 7.90 (dd, 1H), 8.32 (s, 1H), 8.35 (d, 1H), 8.89 (t, 1H), 9.08 (d, 1H), 9.45 (s, 1H).

Intermediate Example Int08.031

4-{[6-(4-aminophenyl)[1,2,4]triazolo[1,5-a]pyridin-2-yl]amino}-3-methoxy-N-(2,2,2-trifluoroethyl)benzamide

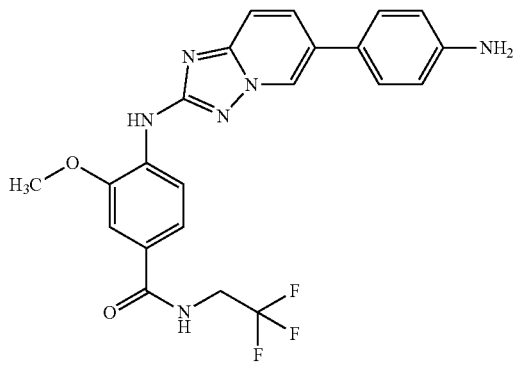 [SMILES: COc1cc(C(=O)NCC(F)(F)F)ccc1Nc1nc2ccc(-c3ccc(N)cc3)cn2n1]

To a stirred suspension of Int08.030 (850 mg) in dichloromethane (16 mL) was added TFA (3.0 mL). The mixture was stirred at room temperature for 4 h. Further TFA was added (1 mL) and the mixture was stirred at room temperature for 5 h. A saturated solution of potassium carbonate was added until pH 9 was reached. The mixture was extracted with dichloromethane and methanol (10:1 mixture). The solution was dried (sodium sulfate) and the solvent was removed in vacuum to give 690 mg of the title compound, that was used for the next step without further purification.

¹H-NMR (300 MHz, DMSO-d₆): δ [ppm]=3.92 (s, 3H), 3.98-4.16 (m, 2H), 5.29 (s, 2H), 6.63 (d, 2H), 7.43 (d, 2H), 7.50-7.62 (m, 3H), 7.82 (dd, 1H), 8.28 (s, 1H), 8.35 (d, 1H), 8.85-8.96 (m, 2H).

Intermediate Example Int08.040 tert-butyl (4-{2-[(4-carbamoyl-2-methoxyphenyl)amino][1,2,4]triazolo[1,5-a]pyridin-6-yl}phenyl)carbamate

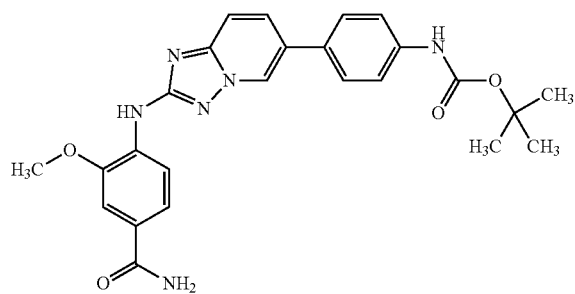 [SMILES: COc1cc(C(N)=O)ccc1Nc1nc2ccc(-c3ccc(NC(=O)OC(C)(C)C)cc3)cn2n1]

To a stirred suspension of Int01.03 (300 mg) in toluene (17 mL) and NMP (5.7 mL) was added 4-bromo-3-methoxy-benzamide (276 mg), chloro(2-dicyclohexylphosphino-2',4',6'-triisopropyl-1,1'-biphenyl)[2-(2-aminoethyl)-phenyl] palladium(II) methyl-tert-butylether adduct (38 mg) and X-Phos (22 mg) and the flask was twice degassed and backfilled with argon. The mixture was stirred for 5 minutes at room temperature. Powdered potassium phosphate (979 mg) was added and the flask was twice degassed and backfilled with argon. The mixture was heated to reflux for 1 h. The reaction mixture was filtered through an aminophase-silica-gel column and the solvent was removed in vacuum. Aminophase-silica-gel chromatography followed by preparative reverse phase HPLC gave a solid that was triturated with a mixture of dichloromethane and hexane to give 121 mg of the title compound.

$^1$H-NMR (400 MHz, DMSO-$d_6$): δ [ppm]=1.46 (s, 9H), 3.91 (s, 3H), 7.16 (br. s., 1H), 7.48-7.57 (m, 4H), 7.60-7.70 (m, 3H), 7.82 (br. s., 1H), 7.90 (dd, 1H), 8.22 (s, 1H), 8.31 (d, 1H), 9.03-9.13 (m, 1H), 9.45 (s, 1H).

Intermediate Example Int08.041

4-{[6-(4-aminophenyl)[1,2,4]triazolo[1,5-a]pyridin-2-yl]amino}-3-methoxy-benzamide

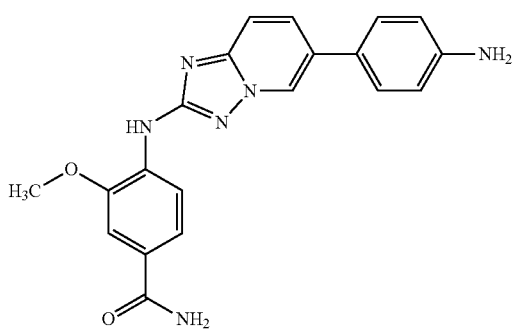 [SMILES: COc1cc(C(N)=O)ccc1Nc1nc2ccc(-c3ccc(N)cc3)cn2n1]

To a stirred suspension of Int08.040 (120 mg) in dichloromethane (3 mL) was added TFA (0.3 mL). The mixture was stirred at room temperature for 16 h. The solvent was removed in vacuum, and the residue was dissolved in ethyl acetate. A half-saturated solution of sodium bicarbonate was added until pH 9 was reached. The mixture was extracted with ethyl acetate. The organic phase was dried (sodium sulfate) and the solvent was removed in vacuum to give 84 mg of the title compound.

$^1$H-NMR (300 MHz, DMSO-$d_6$): δ [ppm]=3.90 (s, 3H), 5.29 (s, 2H), 6.63 (d, 2H), 7.18 (br. s., 1H), 7.43 (d, 2H), 7.47-7.62 (m, 3H), 7.75-7.89 (m, 2H), 8.19 (s, 1H), 8.31 (d, 1H), 8.93 (s, 1H).

Intermediate Example Int08.050 tert-butyl [4-(2-{[4-carbamoyl-2-(2,2,2-trifluoroethoxyl)phenyl]amino}-[1,2,4]triazolo[1,5-a]pyridin-6-yl)phenyl]carbamate

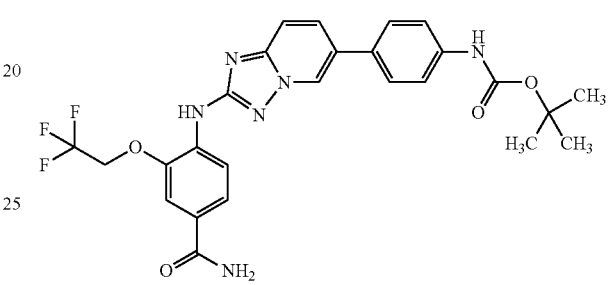

To a stirred suspension of Int01.03 (182 mg) in toluene (4 mL) and NMP (3 mL) was added chloro(2-dicyclohexylphosphino-2',4',6'-triisopropyl-1,1'-biphenyl)[2-(2-aminoethyl)phenyl] palladium(II) methyl-tert-butylether adduct (23 mg), X-Phos (13 mg) and powdered potassium phosphate (356 mg). The flask was twice degassed and backfilled with argon. The mixture was heated to reflux and Int06.03 (200 mg), dissolved in 1 mL NMP was added dropwise. The mixture was heated to reflux for 16 h. The solvent was removed in vacuum. Aminophase-silica-gel chromatography followed by preparative reverse phase HPLC gave 150 mg of the title compound.

$^1$H-NMR (300 MHz, DMSO-$d_6$): δ [ppm]=1.46 (s, 9H), 4.89 (q, 2H), 7.26 (br. s., 1H), 7.54 (d, 2H), 7.59-7.72 (m, 5H), 7.83 (br. s., 1H), 7.91 (dd, 1H), 8.22 (s, 1H), 8.34 (d, 1H), 9.11 (s, 1H), 9.48 (s, 1H).

Intermediate Example Int08.051

4-{[6-(4-aminophenyl)[1,2,4]triazolo[1,5-a]pyridin-2-yl]amino}-3-(2,2,2-trifluoroethoxyl)benzamide

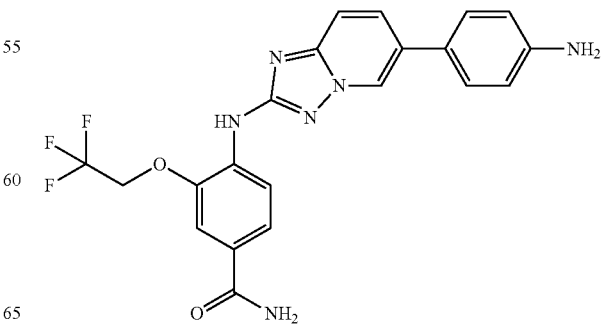

To a stirred suspension of Int08.050 (130 mg) in dichloromethane (10 mL) was added TFA (0.5 mL). The mixture was stirred at room temperature for 2 h. Further TFA was added (3 mL) and the mixture was stirred at room temperature for 2 h. A saturated solution of potassium carbonate was added until pH 9 was reached. The mixture was extracted with dichloromethane and methanol (10:1 mixture). The solution was filtered through an aminophase-silica-gel column and the solvent was removed in vacuum to give 70 mg of the title compound. The crude product was used for the next step without further purification.

Intermediate Example Int08.060 tert-butyl {4-[2-({4-[(3-fluoroazetidin-1-yl)carbonyl]-2-methoxyphenyl}-amino)[1,2,4]triazolo[1,5-a]pyridin-6-yl]phenyl}carbamate

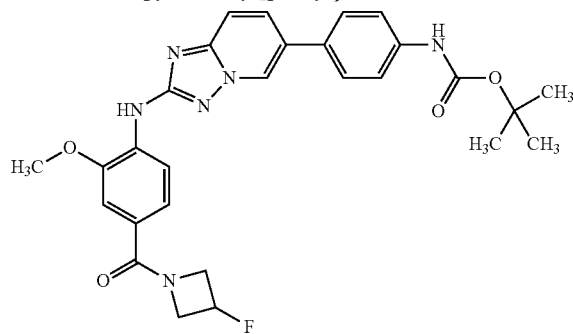

To a stirred suspension of Int01.03 (6.0 g) in toluene (350 mL) and NMP (29 mL) was added Int02.05 (6.91 g), chloro(2-dicyclohexylphosphino-2',4',6'-triisopropyl-1,1'-biphenyl)[2-(2-aminoethyl)phenyl] palladium(II) methyl-tert-butylether adduct (610 mg) and X-Phos (359 mg) and the flask was twice degassed and backfilled with argon. The mixture was stirred for 5 minutes at room temperature. Powdered potassium phosphate (13.7 g) was added and the flask was twice degassed and backfilled with argon. The mixture was heated to reflux for 1 h. The reaction mixture was filtered through an aminophase-silica-gel column and the solvent was removed in vacuum. Aminophase-silica-gel chromatography gave 7.9 g of the title compound.

$^1$H-NMR (300 MHz, DMSO-$d_6$): δ [ppm]=1.46 (s, 9H), 3.90 (s, 3H), 4.04-4.80 (m, 4H), 5.27-5.57 (m, 1H), 7.23 (d, 1H), 7.27 (dd, 1H), 7.54 (d, 2H), 7.59-7.71 (m, 3H), 7.89 (dd, 1H), 8.29 (s, 1H), 8.34 (d, 1H), 9.06 (d, 1H), 9.45 (s, 1H).

Intermediate Example Int08.061

(4-{[6-(4-aminophenyl)[1,2,4]triazolo[1,5-a]pyridin-2-yl]amino}-3-methoxyphenyl)(3-fluoroazetidin-1-yl)methanone

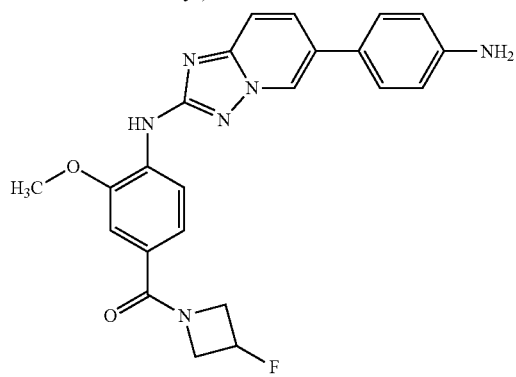

To a stirred suspension of Int08.060 (7.8 g) in dichloromethane (55 mL) was added TFA (28 mL). The mixture was stirred at room temperature for 16 h. The solvent was removed in vacuum and the residue was dissolved in ethyl acetate. A saturated solution of sodium bicarbonate was added until pH 9 was reached. The precipitated solid was collected by filtration to give 5.2 g of the title compound. The crude product was used for the next step without further purification.

$^1$H-NMR (300 MHz, DMSO-$d_6$): δ [ppm]=3.90 (s, 3H), 4.45 (br. s., 4H), 5.20-5.58 (m, 3H), 6.63 (d, 2H), 7.23 (d, 1H), 7.27 (dd, 1H), 7.42 (d, 2H), 7.52-7.61 (m, 1H), 7.81 (dd, 1H), 8.23 (s, 1H), 8.34 (d, 1H), 8.86-8.94 (m, 1H).

Intermediate Example Int08.070 tert-butyl [4-(2-{[4-(azetidin-1-ylcarbonyl)-2-methoxyphenyl]amino}-[1,2,4]triazolo[1,5-a]pyridin-6-yl)phenyl]carbamate

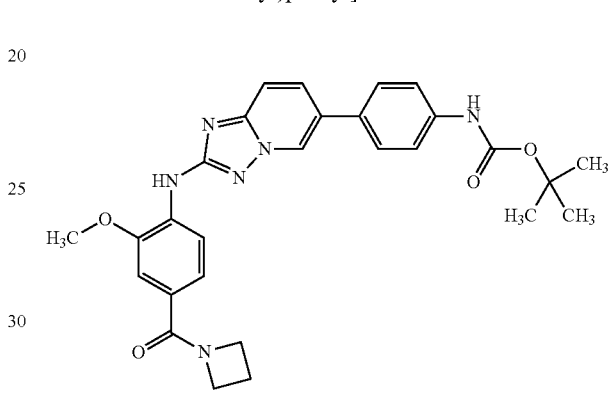

To a stirred suspension of Int01.03 (672 mg) in toluene (13 mL) and NMP (1.3 mL) was added Int02.04 (670 mg), chloro(2-dicyclohexylphosphino-2',4',6'-tri-isopropyl-1,1'-biphenyl)[2-(2-aminoethyl)phenyl] palladium(II) methyl-tert-butylether adduct (85 g), X-Phos (50 mg) and powdered potassium phosphate (1.32 g). The flask was twice degassed and backfilled with argon. The mixture was heated to reflux for 16 h. Aminophase-silica-gel chromatography of the crude mixture gave 600 mg of the title compound, which contained a small amount of Int08.071. The crude product was used for the next step without further purification.

Intermediate Example Int08.071

(4-{[6-(4-aminophenyl)[1,2,4]triazolo[1,5-a]pyridin-2-yl]amino}-3-methoxyphenyl)(azetidin-1-yl)methanone

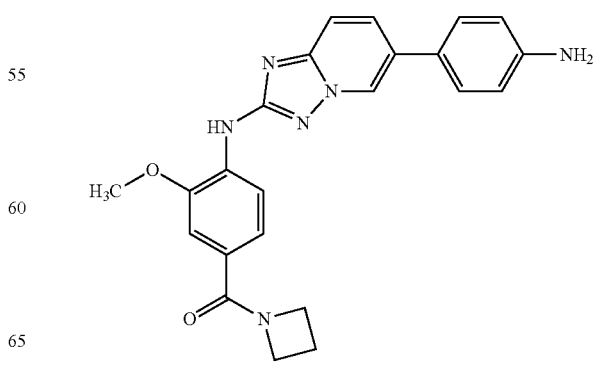

To a stirred suspension of Int08.070 (600 mg) in dichloromethane (12 mL) was added TFA (2.2 mL). The mixture was stirred at room temperature for 16 h. A saturated solution of potassium carbonate was added until pH 9 was reached. The mixture was extracted with dichloromethane and methanol (10:1 mixture). The reaction mixture was filtered through an aminophase-silica-gel column and the solvent was removed in vacuum. The residue was triturated with ethanol to give 475 mg of the title compound.

¹H-NMR (300 MHz, DMSO-d₆): δ [ppm]=2.23 (quin, 2H), 3.88 (s, 3H), 4.00 (br. s., 2H), 4.33 (br. s., 2H), 5.30 (s, 2H), 6.62 (d, 2H), 7.18-7.28 (m, 2H), 7.42 (d, 2H), 7.57 (d, 1H), 7.81 (dd, 1H), 8.23 (s, 1H), 8.32 (d, 1H), 8.90 (d, 1H).

Intermediate Example Int08.080 tert-butyl [4-(2-{[2-methoxy-4-(2-oxo-1,3-oxazolidin-3-yl)phenyl]amino}-[1,2,4]triazolo[1,5-a]pyridin-6-yl)phenyl]carbamate

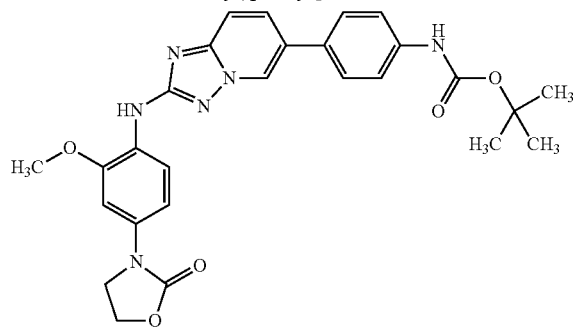

To a stirred suspension of Int01.03 (4.0 g) in toluene (80 mL) and NMP (8 mL) was added Int07.01 (4.4 g), chloro(2-dicyclohexylphosphino-2',4',6'-triiso-propyl-1,1'-biphenyl)[2-(2-aminoethyl)phenyl] palladium(II) methyl-tert-butylether adduct (1.02 g), X-Phos (586 mg) and powdered potassium phosphate (9.13 g). The flask was twice degassed and backfilled with argon. The mixture was heated to reflux for 16 h. Aminophase-silica-gel chromatography of the crude mixture gave 2.0 g of the title compound.

¹H-NMR (400 MHz, DMSO-d₆): δ [ppm]=1.46 (s, 9H), 3.84 (s, 3H), 4.04 (dd, 2H), 4.34-4.47 (m, 2H), 6.98 (dd, 1H), 7.39 (d, 1H), 7.50-7.60 (m, 3H), 7.61-7.70 (m, 2H), 7.80-7.89 (m, 1H), 7.96 (s, 1H), 8.14 (d, 1H), 9.01 (dd, 1H), 9.44 (s, 1H).

Intermediate Example Int08.081

3-(4-{[6-(4-aminophenyl)[1,2,4]triazolo[1,5-a]pyridin-2-yl]amino}-3-methoxyphenyl)-1,3-oxazolidin-2-one

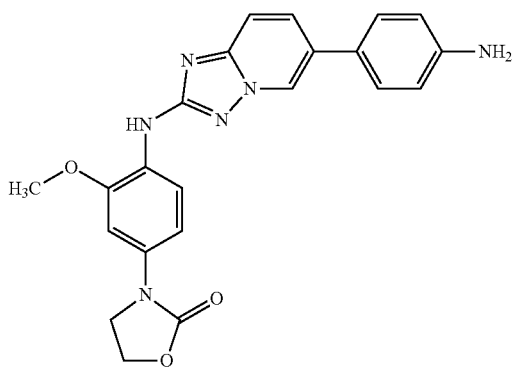 [SMILES: COc1cc(N2CCOC2=O)ccc1Nc1nc2ccc(-c3ccc(N)cc3)cn2n1]

To a stirred suspension of Int08.080 (2.0 g) in DCM (10 mL) was added TFA (6.3 mL). The mixture was stirred at room temperature for 16 h. Further dichloromethane (10 mL) and TFA (6.3 mL) were added, and the mixture was stirred at room temperature for 24 h. The solvent was removed in vacuum and the residue was dissolved in ethyl acetate. A saturated solution of sodium bicarbonate was added until pH 9 was reached. The precipitated solid was collected by filtration to give 1.44 g of the title compound.

¹H-NMR (300 MHz, DMSO-d₆): δ [ppm]=3.84 (s, 3H), 3.99-4.09 (m, 2H), 4.34-4.46 (m, 2H), 5.25 (s, 2H), 6.63 (d, 2H), 6.97 (dd, 1H), 7.34-7.45 (m, 3H), 7.51 (dd, 1H), 7.77 (dd, 1H), 7.88 (s, 1H), 8.15 (d, 1H), 8.84 (d, 1H).

Intermediate Example Int08.090 tert-butyl [4-(2-{[4-(dimethylcarbamoyl)-2-methoxyphenyl]amino}[1,2,4]triazolo[1,5-a]pyridin-6-yl)phenyl]carbamate

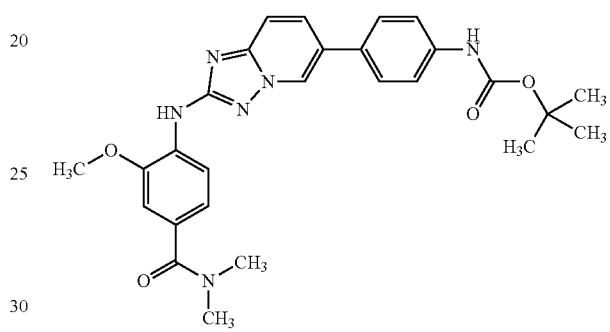

To a stirred suspension of Int01.03 (500 mg) in toluene (12 mL) and NMP (0.6 mL) was added Int02.06 (491 mg), chloro(2-dicyclohexylphosphino-2',4',6'-triisopropyl-1,1'-biphenyl)[2-(2-aminoethyl)phenyl] palladium(II) methyl-tert-butylether adduct (64 mg), X-Phos (37 mg) and powdered potassium phosphate (0.98 g). The flask was twice degassed and backfilled with argon. The mixture was heated to reflux for 16 h. The solvent was removed in vacuum. Aminophase-silica-gel chromatography gave a solid that was triturated with ether to give 650 mg of the title compound.

Intermediate Example Int08.091

4-{[6-(4-aminophenyl)[1,2,4]triazolo[1,5-a]pyridin-2-yl]amino}-3-methoxy-N,N-dimethylbenzamide

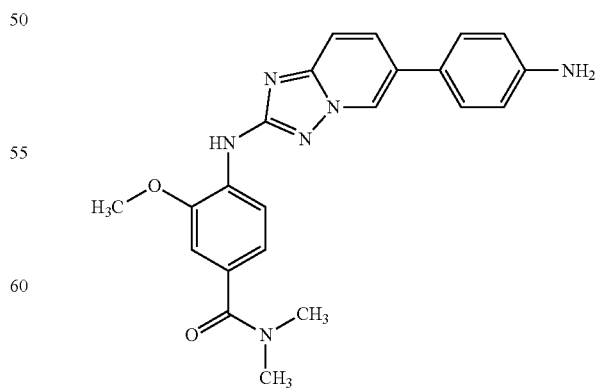

Starting with Int08.090, Int08.091 was prepared analogously to the procedure for the preparation of Int08.071.

Intermediate Example Int08.100 tert-butyl [4-(2-{[2-methoxy-4-(pyrrolidin-1-ylcarbonyl)phenyl]amino}[1,2,4]triazolo[1,5-a]pyridin-6-yl)phenyl]carbamate

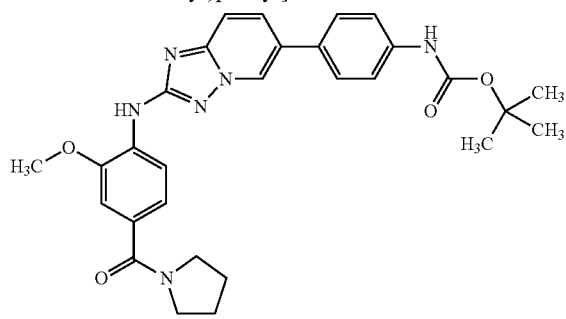

Starting with Int01.03 and Int02.07, Int08.100 was prepared analogously to the procedure for the preparation of Int08.090.

Intermediate Example Int08.101

(4-{[6-(4-aminophenyl)[1,2,4]triazolo[1,5-a]pyridin-2-yl]amino}-3-methoxyphenyl)(pyrrolidin-1-yl)methanone

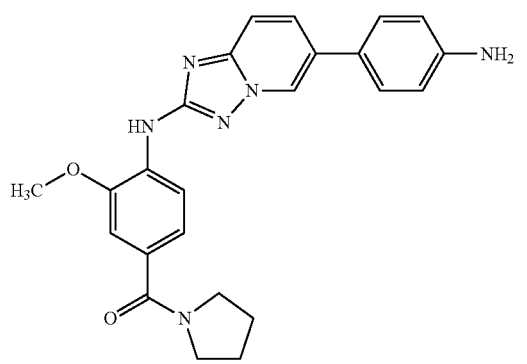 [SMILES: COc1cc(C(=O)N2CCCC2)ccc1Nc1nc2ccc(-c3ccc(N)cc3)cn2n1]

Starting with Int08.100, Int08.101 was prepared analogously to the procedure for the preparation of Int08.071.

Intermediate Example Int08.110 tert-butyl {4-[2-({4-[(3-fluoroazetidin-1-yl)carbonyl]-2-(2,2,2-trifluoroethoxyl)phenyl}amino)[1,2,4]triazolo[1,5-a]pyridin-6-yl]phenyl}carbamate

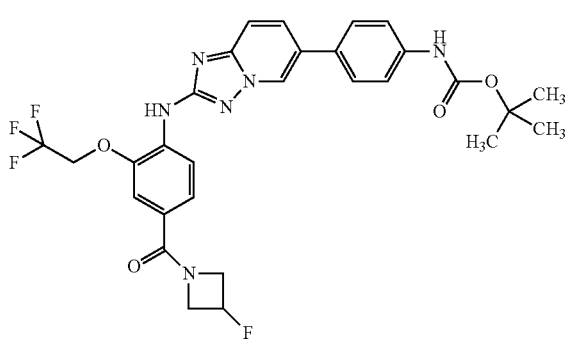 [SMILES: CC(C)(C)OC(=O)Nc1ccc(-c2ccc3nc(Nc4ccc(C(=O)N5CC(F)C5)cc4OCC(F)(F)F)nn3c2)cc1]

Starting with Int01.03 and Int06.04, Int08.110 was prepared analogously to the procedure for the preparation of Int08.090.

Intermediate Example Int08.111

[4-{[6-(4-aminophenyl)[1,2,4]triazolo[1,5-a]pyridin-2-yl]amino}-3-(2,2,2-trifluoroethoxy)phenyl](3-fluoroazetidin-1-yl)methanone

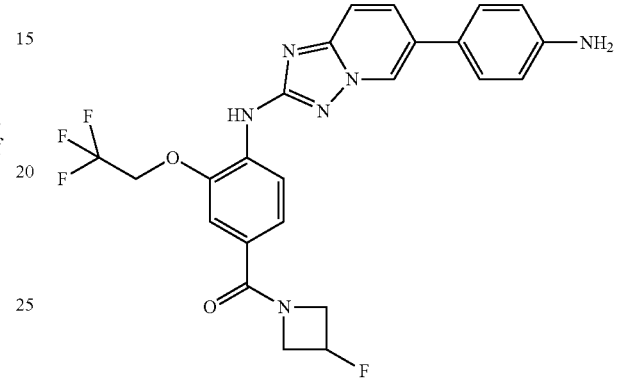

Starting with Int08.110, Int08.111 was prepared analogously to the procedure for the preparation of Int08.071.

Intermediate Example Int08.120 tert-butyl {4-[2-({4-[(3-hydroxyazetidin-1-yl)carbonyl]-2-(2,2,2-trifluoroethoxyl)phenyl}amino)[1,2,4]triazolo[1,5-a]pyridin-6-yl]phenyl}carbamate

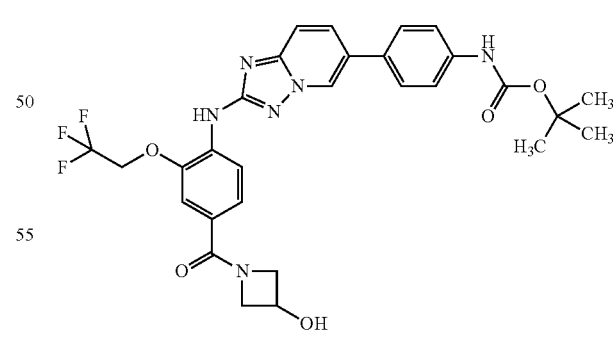

Starting with Int01.03 and Int06.05, Int08.120 was prepared analogously to the procedure for the preparation of Int08.090.

Intermediate Example Int08.121

[4-{[6-(4-aminophenyl)[1,2,4]triazolo[1,5-a]pyridin-2-yl]amino}-3-(2,2,2-trifluoroethoxy)phenyl](3-hydroxyazetidin-1-yl)methanone

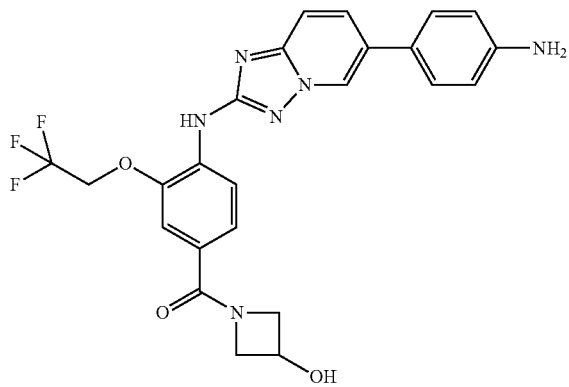 [SMILES: Nc1ccc(-c2ccc3nc(Nc4ccc(C(=O)N5CC(O)C5)cc4OCC(F)(F)F)nn3c2)cc1]

Starting with Int08.120, Int08.121 was prepared analogously to the procedure for the preparation of Int08.071.

Intermediate Example Int08.130 tert-butyl [4-(2-{[4-(pyrrolidin-1-ylcarbonyl)-2-(2,2,2-trifluoroethoxy)phenyl]amino}[1,2,4]triazolo[1,5-a]pyridin-6-yl)phenyl]carbamate

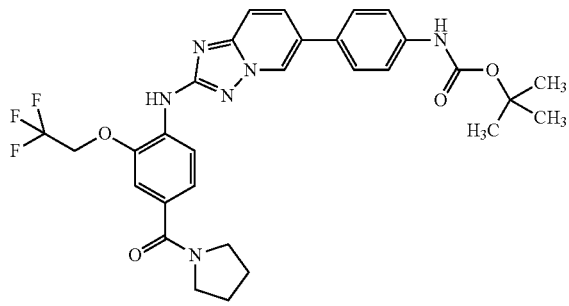 [SMILES: CC(C)(C)OC(=O)Nc1ccc(-c2ccc3nc(Nc4ccc(C(=O)N5CCCC5)cc4OCC(F)(F)F)nn3c2)cc1]

Starting with Int01.03 and Int06.06, Int08.130 was prepared analogously to the procedure for the preparation of Int08.090.

Intermediate Example Int08.131

[4-{[6-(4-aminophenyl)[1,2,4]triazolo[1,5-a]pyridin-2-yl]amino}-3-(2,2,2-trifluoroethoxy)phenyl](pyrrolidin-1-yl)methanone

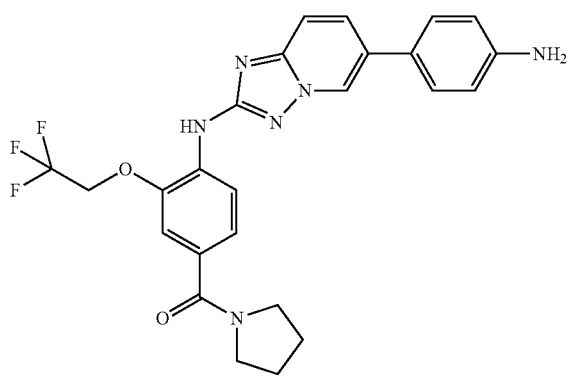 [SMILES: Nc1ccc(-c2ccc3nc(Nc4ccc(C(=O)N5CCCC5)cc4OCC(F)(F)F)nn3c2)cc1]

Starting with Int08.130, Int08.131 was prepared analogously to the procedure for the preparation of Int08.071.

Intermediate Example Int08.140 methyl 2-(4-fluorophenyl)-3-hydroxypropanoate

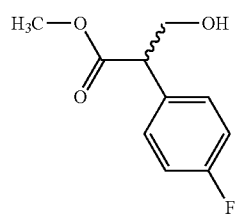

To a stirred solution of methyl (4-fluorophenyl)acetate (5.5 g) in DMSO (220 mL) was added 1,3,5-trioxane (3.24 g) and sodium methoxide (88 mg). The mixture was stirred at room temperature for 16 h. Water was added and the reaction mixture was extracted with ethyl acetate. The organic phase was washed with saturated sodium chloride solution, dried (sodium sulfate) and the solvent was removed in vacuum. Silicagel chromatography gave 3.8 g of the title compound.

$^1$H-NMR (400 MHz, DMSO-d$_6$): δ [ppm]=3.50-3.61 (m, 4H), 3.71-3.79 (m, 1H), 3.82-3.90 (m, 1H), 4.98 (t, 1H), 7.07-7.16 (m, 2H), 7.27-7.34 (m, 2H).

Intermediate Example Int08.141 methyl 3-{[tert-butyl(diphenyl)silyl]oxy}-2-(4-fluorophenyl)propanoate

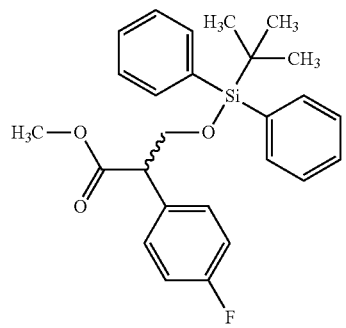 [SMILES: COC(=O)C(CO[Si](c1ccccc1)(c1ccccc1)C(C)(C)C)c1ccc(F)cc1]

To a stirred solution of imidazole (2.36 g) and tert-butyl (chloro)diphenylsilane (4.58 g) in DMF (90 mL) was added a solution of Int08.140 (2.75 g), dissolved in DMF (20 mL). The mixture was stirred at room temperature for 30 minutes. Water was added and the reaction mixture was extracted with ethyl acetate. The organic phase was washed with saturated sodium chloride solution, dried (sodium sulfate) and the solvent was removed in vacuum. Silicagel chromatography gave 5.3 g of the title compound.

¹H-NMR (300 MHz, DMSO-d₆): δ [ppm]=0.90 (s, 9H), 3.60 (s, 3H), 3.77 (dd, 1H), 3.92-4.00 (m, 1H), 4.02-4.11 (m, 1H), 7.05-7.16 (m, 2H), 7.24-7.33 (m, 2H), 7.33-7.46 (m, 6H), 7.46-7.57 (m, 4H).

Intermediate Example Int08.142

3-{[tert-butyl(diphenyl)silyl]oxy}-2-(4-fluorophenyl)propanoic acid

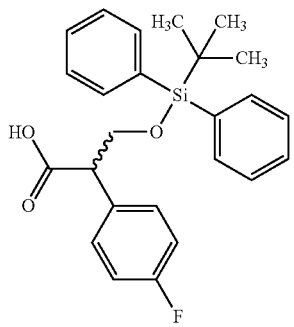 [SMILES: CC(C)(C)[Si](OCC(C(=O)O)c1ccc(F)cc1)(c1ccccc1)c1ccccc1]

To a stirred solution of Int08.141 (5.3 g) in 2-propanol (55 mL) was added a solution of sodium hydroxide (0.97 g), dissolved in water (18 mL). The mixture was stirred at 60° C. for 30 minutes. The solution was cooled to room temperature, saturated ammonium chloride solution was added and the reaction mixture was extracted with ethyl acetate. The organic phase was dried (sodium sulfate) and the solvent was removed in vacuum. Silicagel chromatography gave 5.3 g of the title compound.

¹H-NMR (300 MHz, DMSO-d₆): δ [ppm]=0.90 (s, 9H), 3.67-3.76 (m, 1H), 3.77-3.87 (m, 1H), 4.02-4.10 (m, 1H), 7.05-7.15 (m, 2H), 7.24-7.32 (m, 2H), 7.32-7.46 (m, 6H), 7.46-7.59 (m, 4H), 12.64 (br. s., 1H).

Intermediate Example Int08.143

3-{[tert-butyl(diphenyl)silyl]oxy}-2-(4-fluorophenyl)-N-[4-(2-{[4-(methyl-sulfonyl)-2-(2,2,2-trifluoroethoxy)phenyl]amino}[2,4]triazolo[1,5-a]-pyridin-6-yl)phenyl]propanamide

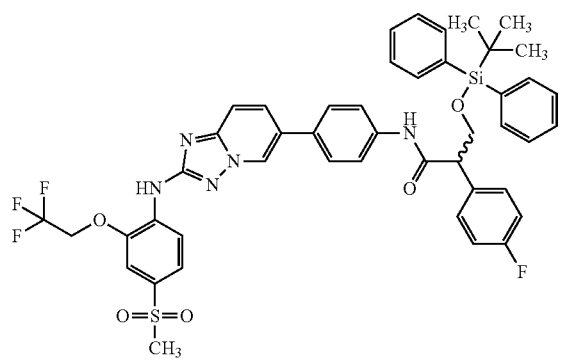 [SMILES: CC(C)(C)[Si](OCC(C(=O)Nc1ccc(-c2ccc3nc(Nc4ccc(S(C)(=O)=O)cc4OCC(F)(F)F)nn3c2)cc1)c1ccc(F)cc1)(c1ccccc1)c1ccccc1]

To a stirred solution of Int08.021 (400 mg) in DMF (10 mL) was added potassium carbonate (347 mg), Int08.142 (425 mg) and HATU (478 mg). The mixture was stirred at room temperature for 16 h. Water was added, the mixture was stirred for 15 minutes and the mixture was extracted with ethyl acetate. The organic phase was washed with saturated sodium chloride solution, dried (sodium sulfate) and the solvent was removed in vacuum. Aminophase-silicagel chromatography gave 346 mg of the title compound.

¹H-NMR (400 MHz, DMSO-d₆): δ [ppm]=0.91 (s, 9H), 3.17 (s, 3H), 3.74 (dd, 1H), 4.07 (dd, 1H), 4.21-4.32 (m, 1H), 5.00 (q, 2H), 7.08-7.17 (m, 2H), 7.32-7.47 (m, 8H), 7.50-7.56 (m, 2H), 7.58-7.66 (m, 4H), 7.66-7.78 (m, 5H), 7.95 (dd, 1H), 8.51 (d, 1H), 8.57 (s, 1H), 9.13 (d, 1H), 10.38 (s, 1H).

Intermediate Example Int08.144

3-{[tert-butyl(diphenyl)silyl]oxy}-2-(4-fluorophenyl)-N-[4-(2-{[2-methoxy-4-(methylsulfonyl)phenyl]amino}[1,2,4]triazolo[1,5-a]pyridin-6-yl)phenyl]propanamide

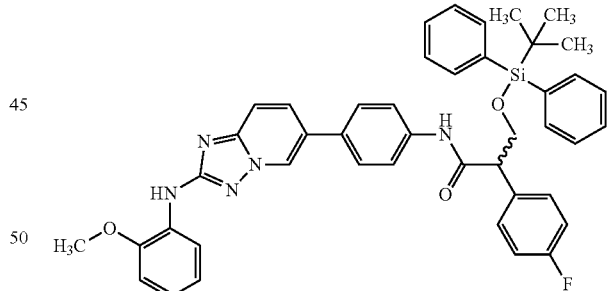

Starting with Int08.011 and Int08.142, Int08.144 was prepared analogously to the procedure for the preparation of Int08.143.

Intermediate Example Int08.145

3-{[tert-butyl(diphenyl)silyl]oxy}-N-{4-[2-({4-[(3-fluoroazetidin-1-yl)carbonyl]-2-(2,2,2-trifluoroethoxy)phenyl}amino)[1,2,4]triazolo[1,5-a]pyridin-6-yl]phenyl}-2-(4-fluorophenyl)propanamide

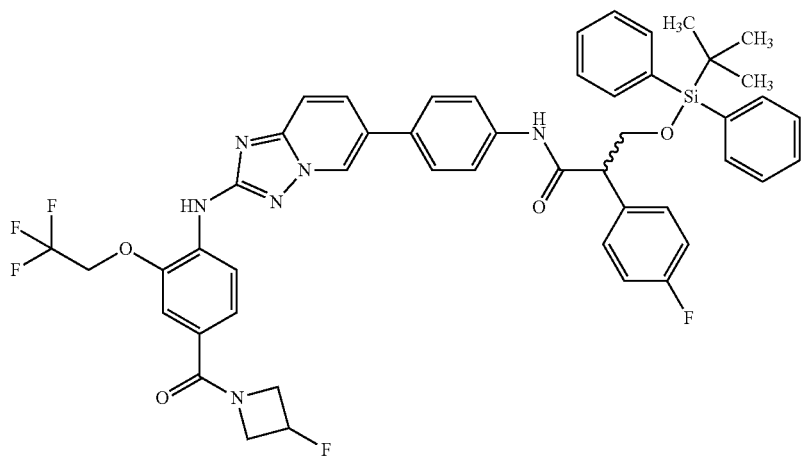 [SMILES: CC(C)(C)[Si](OCC(C(=O)Nc1ccc(-c2ccc3nc(Nc4ccc(C(=O)N5CC(F)C5)cc4OCC(F)(F)F)nn3c2)cc1)c1ccc(F)cc1)(c1ccccc1)c1ccccc1]

Starting with Int08.111 and Int08.142, Int08.145 was prepared analogously to the procedure for the preparation of Int08.143.

Intermediate Example Int08.146

(2S)-3-{[tert-butyl(diphenyl)silyl]oxy}-N-{4-[2-({4-[(3-fluoroazetidin-1-yl)carbonyl]-2-(2,2,2-trifluoroethoxyl)phenyl}amino)[1,2,4]triazolo[1,5-a]pyridin-6-yl]phenyl}-2-(4-fluorophenyl)propanamide

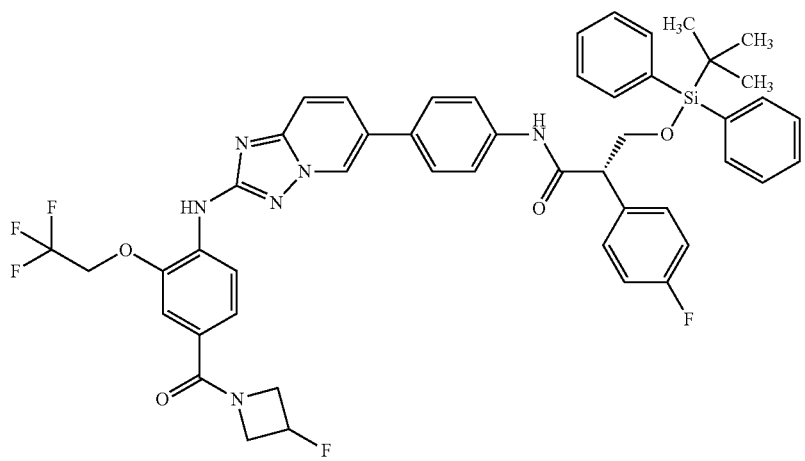 [SMILES: CC(C)(C)[Si](OC[C@@H](C(=O)Nc1ccc(-c2ccc3nc(Nc4ccc(C(=O)N5CC(F)C5)cc4OCC(F)(F)F)nn3c2)cc1)c1ccc(F)cc1)(c1ccccc1)c1ccccc1]

The enantiomers of 730 mg of Int08.145 were separated using chiral HPLC. Column: Chiralpak IA 5μ 250×30 mm; Flow: 50.0 mL/min; Solvent: A: Hexane, B: Ethanol; C: Formic acid; Solvent mixture: A:B:C=70:30:0.1. Retention time of the titel compound: 20.4-25.2 min (Peak 2). Yield: 295 mg.

Column: Chiralpak IA 5μ 150×4.6; Flow: 1.00 mL/min; Solvent: A: Hexane, B: Ethanol; C: Formic acid; Solvent mixture: A:B:C=70:30:0.1. Run Time: 40 min. Retention Time: 32.59 min; UV 254 nm; Enantiomeric Ratio: 2.1%: 97.9%.

Intermediate Example Int08.150 tert-butyl [(1R)-1-(4-fluorophenyl)-2-{[4-(2-{[2-methoxy-4-(methyl-sulfonyl)phenyl]amino}[1,2,4]triazolo[1,5-a]pyridin-6-yl)phenyl]amino}-2-oxo-ethyl]carbamate

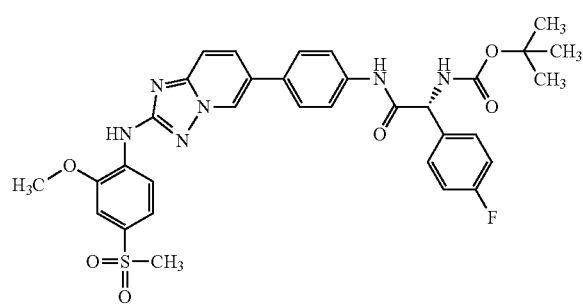 [SMILES: COc1cc(S(C)(=O)=O)ccc1Nc1nc2ccc(-c3ccc(NC(=O)[C@H](NC(=O)OC(C)(C)C)c4ccc(F)cc4)cc3)cn2n1]

To a stirred suspension of Int08.011 (200 mg) in DMF (1.6 mL) and dichloromethane (3.2 mL) was added sodium bicarbonate (82 mg), (2R)-[(tert-butoxycarbonyl)amino](4-fluorophenyl)acetic acid (166 mg) and HATU (279 mg). The mixture was stirred at room temperature for 4 h. Water was added, and the mixture was stirred for 30 minutes. A half-saturated solution of sodium bicarbonate was added and the mixture was extracted with ethyl acetate. The organic phase was washed with saturated sodium chloride solution, dried (sodium sulfate) and the solvent was removed in vacuum. Aminophase-silica-gel chromatography gave 300 mg of the title compound.

$^1$H-NMR (300 MHz, DMSO-d$_6$): δ [ppm]=1.36 (s, 9H), 3.16 (s, 3H), 3.95 (s, 3H), 5.34 (d, 1H), 7.17 (t, 2H), 7.42 (d, 1H), 7.47-7.55 (m, 3H), 7.58-7.78 (m, 6H), 7.92 (dd, 1H), 8.48 (d, 1H), 8.64 (s, 1H), 9.12 (d, 1H), 10.38 (s, 1H).

Intermediate Example Int08.151 tert-butyl [(1R)-1-(4-fluorophenyl)-2-{[4-(2-{[4-(methylsulfonyl)-2-(2,2,2-trifluoroethoxy)phenyl]amino}[1,2,4]triazolo[1,5-a]pyridin-6-yl)phenyl]amino}-2-oxoethyl]carbamate

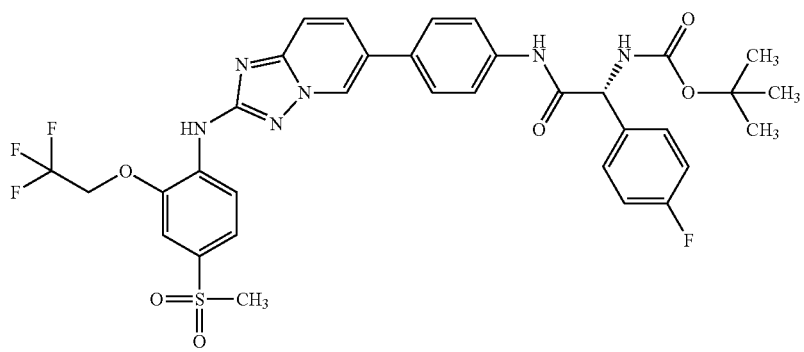 [SMILES: CC(C)(C)OC(=O)N[C@@H](C(=O)Nc1ccc(-c2ccc3nc(Nc4ccc(S(C)(=O)=O)cc4OCC(F)(F)F)nn3c2)cc1)c1ccc(F)cc1]

Starting with Int08.021, Int08.151 was prepared analogously to the procedure for the preparation of Int08.150.

Intermediate Example Int08.152 tert-butyl [(1R)-1-(4-fluorophenyl)-2-{[4-(2-{[2-methoxy-4-(2-oxo-1,3-oxazolidin-3-yl)phenyl]amino}[1,2,4]triazolo[1,5-a]pyridin-6-yl)phenyl]amino}-2-oxoethyl]carbamate

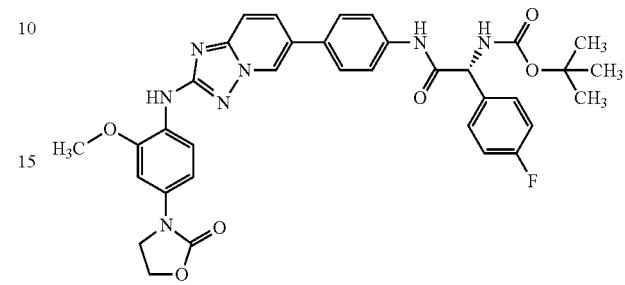

Starting with Int08.081, Int08.152 was prepared analogously to the procedure for the preparation of Int08.150.

Intermediate Example Int08.153 tert-butyl [(1R)-2-({4-[2-({4-[(3-fluoroazetidin-1-yl)carbonyl]-2-methoxyphenyl}amino)[1,2,4]triazolo[1,5-a]pyridin-6-yl]phenyl}amino)-1-(4-fluorophenyl)-2-oxoethyl]carbamate

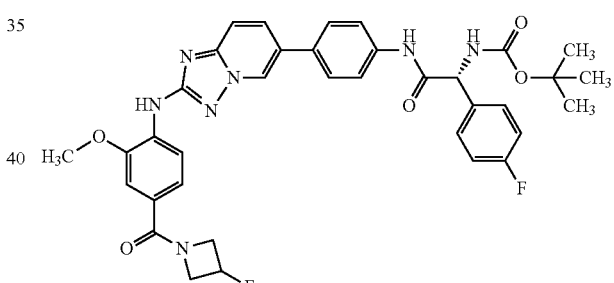

Starting with Int08.061, Int08.153 was prepared analogously to the procedure for the preparation of Int08.150.

Intermediate Example Int08.154 tert-butyl [(1R)-2-{[4-(2-{[4-(azetidin-1-ylcarbonyl)-2-methoxyphenyl]amino}[1,2,4]triazolo[1,5-a]pyridin-6-yl)phenyl]amino}-1-(4-fluorophenyl)-2-oxoethyl]carbamate

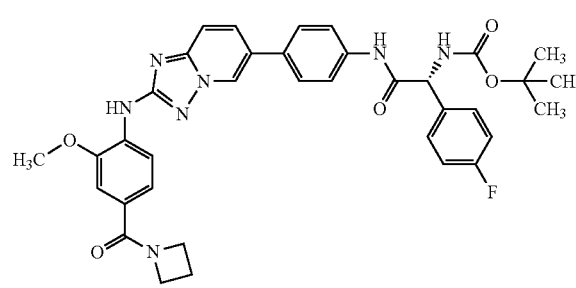 [SMILES: COc1cc(C(=O)N2CCC2)ccc1Nc1nc2ccc(-c3ccc(NC(=O)[C@H](NC(=O)OC(C)(C)C)c4ccc(F)cc4)cc3)cn2n1]

Starting with Int08.071, Int08.154 was prepared analogously to the procedure for the preparation of Int08.150.

Intermediate Example Int08.155 tert-butyl [(1R)-1-(4-fluorophenyl)-2-{[4-(2-{[2-methoxy-4-(pyrrolidin-1-ylcarbonyl)phenyl]amino}[1,2,4]triazolo[1,5-a]pyridin-6-yl)phenyl]amino}-2-oxoethyl]carbamate

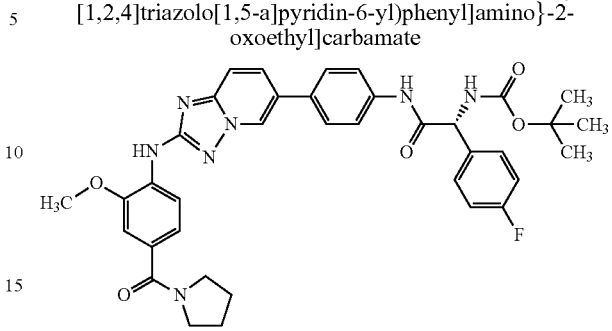

Starting with Int08.101, Int08.155 was prepared analogously to the procedure for the preparation of Int08.150.

Intermediate Example Int08.156 tert-butyl [(1R)-2-({4-[2-({4-[(3-fluoroazetidin-1-yl)carbonyl]-2-(2,2,2-trifluoroethoxyl)phenyl}amino)[1,2,4]triazolo[1,5-a]pyridin-6-yl]phenyl}amino)-1-(4-fluorophenyl)-2-oxoethyl]carbamate

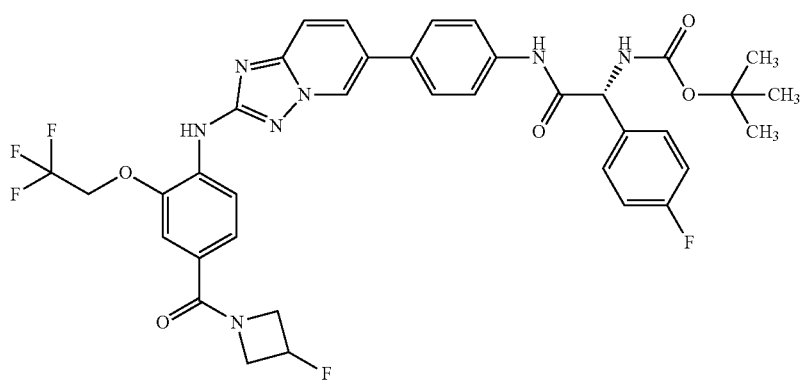 [SMILES: CC(C)(C)OC(=O)N[C@@H](C(=O)Nc1ccc(-c2ccc3nc(Nc4ccc(C(=O)N5CC(F)C5)cc4OCC(F)(F)F)nn3c2)cc1)c1ccc(F)cc1]

Starting with Int08.111, Int08.156 was prepared analogously to the procedure for the preparation of Int08.150.

Intermediate Example Int08.157 tert-butyl [(1R)-1-(4-fluorophenyl)-2-oxo-2-{[4-(2-{[4-(pyrrolidin-1-ylcarbonyl)-2-(2,2,2-trifluoroethoxyl)phenyl]amino}[1,2,4]triazolo[1,5-a]pyridin-6-yl)phenyl]amino}ethyl]carbamate

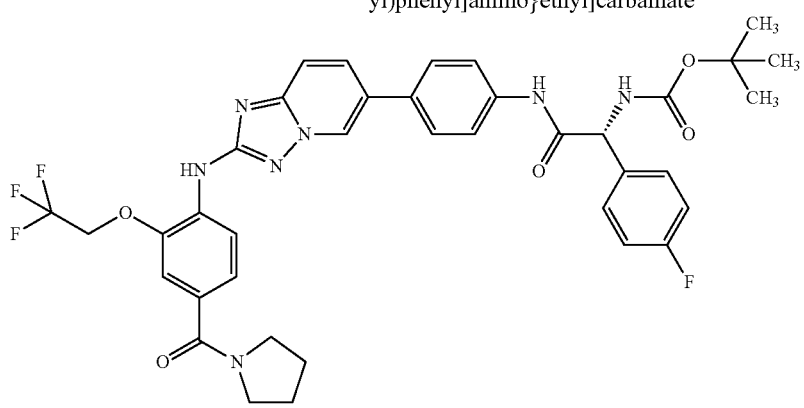

Starting with Int08.131, Int08.157 was prepared analogously to the procedure for the preparation of Int08.150.

Intermediate Example Int09.01

Rac-methyl 2-(4-fluorophenyl)propanoate

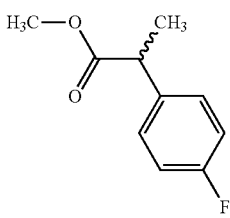

To a stirred solution of diisopropylamine (13.0 g) in tetrahydrofurane (160 mL) was added a solution of n-butyllithium in hexane (51.4 mL; c=2.5 M) at −78° C. The solution was stirred at 0° C. for 15 minutes. The solution was cooled to −78° C. and a solution of methyl (4-fluorophenyl) acetate (18.0 g), dissolved in tetrahydrofurane (40 mL) was added. The solution was stirred at −78° C. for 30 minutes. Methyl iodide (10.0 mL) was added at −78° C., and the solution was allowed to warm up to 0° C. within 1 h. Water was added and the reaction mixture was extracted with ethyl acetate. The organic phase was dried (sodium sulfate) and the solvent was removed in vacuum. Silicagel chromatography gave 18.9 g of the title compound.

$^1$H-NMR (400 MHz, DMSO-$d_6$): δ [ppm]=1.34 (d, 3H), 3.55 (s, 3H), 3.79 (q, 1H), 7.08-7.15 (m, 2H), 7.25-7.32 (m, 2H).

Intermediate Example Int09.02

Rac-2-(4-fluorophenyl)propanoic acid

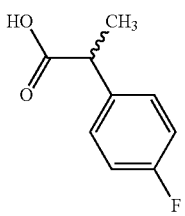

To a stirred solution of Int09.01 (18.9 g) in ethanol (200 mL) was added a solution of potassium hydroxide (35 g), dissolved in water (200 mL). The mixture was stirred at 0° C. for 4 h. Hydrochloric acid (c=4.0 M) was added until pH 5 was reached and the reaction mixture was extracted with ethyl acetate. The organic phase was separated and the solvent was removed in vacuum to give 15.64 g of the title product. The crude product was used without further purification.

$^1$H-NMR (300 MHz, DMSO-$d_6$): δ [ppm]=1.31 (d, 3H), 3.66 (q, 1H), 7.05-7.15 (m, 2H), 7.24-7.33 (m, 2H), 12.30 (s, 1H).

Intermediate Example Int09.03

(2R)-2-(4-fluorophenyl)propanoic acid

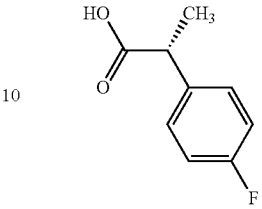

To a stirred solution of Int09.02 (23.6 g) in refluxing ethyl acetate (250 mL) was added a solution of (1S)-1-phenylethanamine (17.35 g) in ethyl acetate. The mixture was allowed to cool down to room temperature within 1 h. A white solid was collected by filtration, was washed with ethyl acetate and dried in vacuum to give 27.5 g of a solid. The solid was recrystallized from 400 mL refluxing ethyl acetate. The mixture was allowed to cool down to room temperature. A white solid was collected by filtration, was washed with ethyl acetate and dried in vacuum to give 18.3 g of a solid. The solid was twice recrystallized from refluxing ethyl acetate (350 mL; 300 mL). A white solid was collected by filtration, was washed with ethyl acetate and dried in vacuum to give 10.51 g of a solid. The solid was dissolved in water, hydrochloric acid (c=2.0 M) was added until pH 5 was reached and the reaction mixture was extracted with dichloromethane. The organic phase was dried (sodium sulfate) and the solvent was removed in vacuum to give 5.6 g of the title product. The crude product was used without further purification.

$^1$H-NMR (300 MHz, DMSO-$d_6$): δ [ppm]=1.31 (d, 3H), 3.66 (q, 1H), 7.05-7.16 (m, 2H), 7.24-7.33 (m, 2H), 12.28 (br. s., 1H).

$[α]_D^{20}$: −79.3° (in DMSO)

Column: Chiralcel OJ-H 150×4.6; Flow: 1.00 mL/min; Solvent: A: Hexane, B: 2-propanol with 0.1% formic acid; Solvent mixture: 80% A+20% B. Run Time: 30 min. Retention Time: 3.41 min; UV 254 nm; Enantiomeric Ratio: 99.8%:0.2%.

Intermediate Example Int10.01

1-bromo-2-(cyclopropyloxy)-4-fluorobenzene

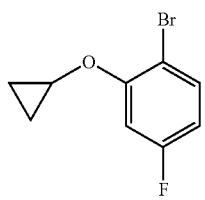 [SMILES: Fc1ccc(Br)c(OC2CC2)c1]

To a stirred solution of 2-bromo-5-fluorophenol (1.0 g) in DMF (15 mL) in a microwave tube was added cesium carbonate (5.0 g), potassium iodide (130 mg) and bromocyclopropane (1.82 g). The mixture was heated in a microwave oven to 180° C. for 1 h, to 200° C. for 1 h and to 220° C. for 1 h. Ethyl acetate was added and the mixture was washed with water. The organic phase was washed with saturated sodium chloride solution, dried (sodium sulfate) and the solvent was removed in vacuum. Silica gel chromatography gave 1.14 g of the title compound.

¹H-NMR (300 MHz, DMSO-d₆): δ [ppm]=0.62-0.88 (m, 4H), 3.90-4.00 (m, 1H), 6.77 (td, 1H), 7.23 (dd, 1H), 7.48-7.63 (m, 1H).

Intermediate Example Int10.02

1-bromo-2-(cyclopropyloxy)-4-(methylsulfanyl)benzene

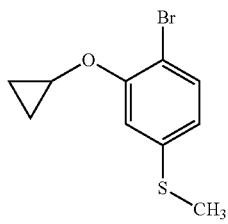

To a stirred solution of Int10.01 (1.4 g) in DMF (12 mL) was added sodium methanethiolate (546 mg). The mixture was for 2 h at 90° C. The mixture was cooled to room temperature, water was added and the mixture was extracted with ethyl acetate. The organic phase was washed with saturated sodium chloride solution, dried (sodium sulfate) and the solvent was removed in vacuum. Silica gel chromatography gave 1.17 g of the title compound.

¹H-NMR (300 MHz, DMSO-d₆): δ [ppm]=0.59-0.85 (m, 4H), 2.46 (s, 3H), 3.95 (tt, 1H), 6.77 (dd, 1H), 7.18 (d, 1H), 7.43 (d, 1H).

Intermediate Example Int10.03

1-bromo-2-(cyclopropyloxy)-4-(methylsulfonyl)benzene

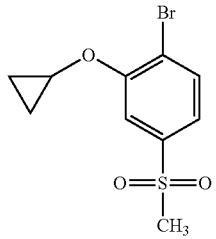

To a stirred solution of Int10.02 (1.15 g) in chloroform (45 mL) was added 3-chlorobenzenecarboperoxoic acid (mCPBA) (2.98 g). The mixture was stirred at room temperature for 2 h. With ice bath cooling, a half-saturated solution of sodium bicarbonate and a 0.2 M solution of sodium thiosulfate was added, the mixture was stirred for 30 minutes and the mixture was extracted with dichloromethane. The organic phase was washed with saturated sodium chloride solution, dried (sodium sulfate) and the solvent was removed in vacuum. Silica gel chromatography gave 0.91 g of the title compound.

¹H-NMR (300 MHz, DMSO-d₆): δ [ppm]=0.66-0.93 (m, 4H), 3.23 (s, 3H), 4.09 (tt, 1H), 7.43 (dd, 1H), 7.77 (d, 1H), 7.84 (d, 1H).

Synthesis of Examples

Compounds of the Present Invention

Example01.01

(2R)-2-(4-fluorophenyl)-N-[4-(2-{[2-methoxy-4-(methylsulfonyl)phenyl]-amino}[1,2,4]triazolo[1,5-a]pyridin-6-yl)phenyl]propanamide

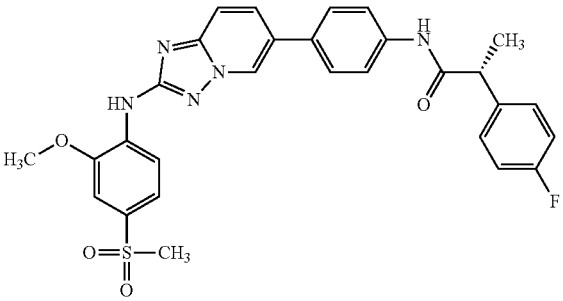 [SMILES: COc1cc(S(C)(=O)=O)ccc1Nc1nc2ccc(-c3ccc(NC(=O)C(C)c4ccc(F)cc4)cc3)cn2n1]

To a stirred suspension of Int08.011 (6.0 g) in DMF (48 mL) and dichloromethane (96 mL) was added sodium bicarbonate (3.69 g), (2R)-2-(4-fluorophenyl)propanoic acid (2.71 g) and HATU (8.36 g). The mixture was stirred at room temperature for 4 h. Water was added, and the mixture was stirred for 30 minutes. A half-saturated solution of sodium bicarbonate was added and the mixture was extracted with ethyl acetate. The organic phase was washed with saturated sodium chloride solution, dried (sodium sulfate) and the solvent was removed in vacuum. Silicagel chromatography gave a solid that was triturated with ethyl acetate to give 7.44 g of the title compound.

¹H-NMR (400 MHz, DMSO-d₆): δ [ppm]=1.40 (d, 3H), 3.16 (s, 3H), 3.84 (q, 1H), 3.96 (s, 3H), 7.09-7.18 (m, 2H), 7.36-7.44 (m, 3H), 7.51 (dd, 1H), 7.63-7.76 (m, 5H), 7.92 (dd, 1H), 8.48 (d, 1H), 8.60 (s, 1H), 9.10 (d, 1H), 10.16 (s, 1H).

[α]$_D^{20}$: −77.0° (in DMSO).

Column: Chiralcel OD-RH 150×4.6; Flow: 1.00 mL/min; Solvent: A: Water with 0.1% formic acid, B: Acetonitrile; Solvent mixture: 40% A+60% B. Run Time: 30 min. Retention Time: 12.83 min; UV 254 nm; Enantiomeric Ratio: <1%:>99%.

Racemate01.01.r

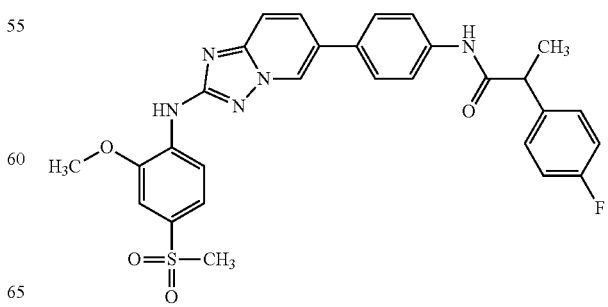

Starting with Int01.05 and Int03.02, Racemate01.01.r was prepared analogously to the procedure for the preparation of Int08.020.

Racemate01.02.r

N-[4-(2-{[2-ethoxy-4-(methylsulfonyl)phenyl]amino}[1,2,4]triazolo[1,5-a]-pyridin-6-yl)phenyl]-2-(4-fluorophenyl)propanamide

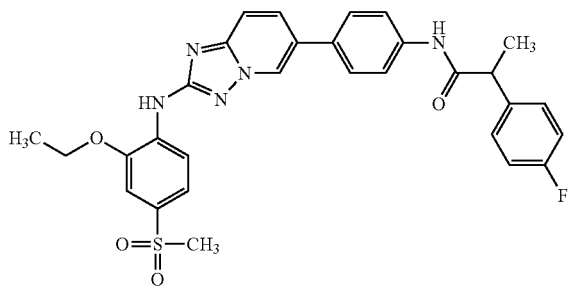 [SMILES: CCOc1cc(S(C)(=O)=O)ccc1Nc1nc2ccc(-c3ccc(NC(=O)C(C)c4ccc(F)cc4)cc3)cn2n1]

Starting with Int01.05 and Int04.03, Racemate01.02.r was prepared analogously to the procedure for the preparation of Int08.020.

Example01.02

(2R)—N-[4-(2-{[2-ethoxy-4-(methylsulfonyl)phenyl]amino}[1,2,4]-triazolo[1,5-a]pyridin-6-yl)phenyl]-2-(4-fluorophenyl)propanamide

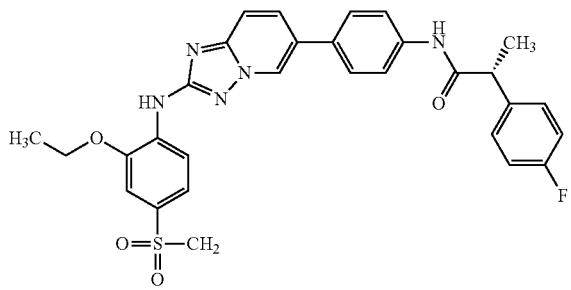 [SMILES: CCOc1cc(S(C)(=O)=O)ccc1Nc1nc2ccc(-c3ccc(NC(=O)[C@H](C)c4ccc(F)cc4)cc3)cn2n1]

The enantiomers of 180 mg of Racemate01.02.r were separated using chiral HPLC. Column: Chiralpak IA 5µ 250×30; Flow: 20.0 mL/min; Solvent: A: Ethanol with 0.1% formic acid; Solvent: 100% A. Retention time of the titel compound: 37.2-49.1 min (Peak 2). Yield: 74 mg.

$^1$H-NMR (300 MHz, DMSO-$d_6$): δ [ppm]=1.35-1.49 (m, 6H), 3.15 (s, 3H), 3.84 (q, 1H), 4.22 (q, 2H), 7.07-7.19 (m, 2H), 7.36-7.44 (m, 3H), 7.50 (dd, 1H), 7.61-7.78 (m, 5H), 7.93 (dd, 1H), 8.44-8.54 (m, 2H), 9.10 (d, 1H), 10.19 (s, 1H).

$[α]_D^{20}$: −72.7° (in DMSO).

Column: Chiralpak IA 5µ 150×4.6; Flow: 1.00 mL/min; Solvent: A: Ethanol with 0.1% formic acid; Solvent: 100% A. Run Time: 30 min. Retention Time: 14.3 min; UV 254 nm; Enantiomeric Ratio: <1%:>99%.

Example01.03

(2R)-2-(4-fluorophenyl)-N-[4-(2-{[4-(methylsulfonyl)-2-(2,2,2-trifluoro-ethoxy)phenyl]amino}[1,2,4]triazolo[1,5-a]pyridin-6-yl)phenyl]-propanamide

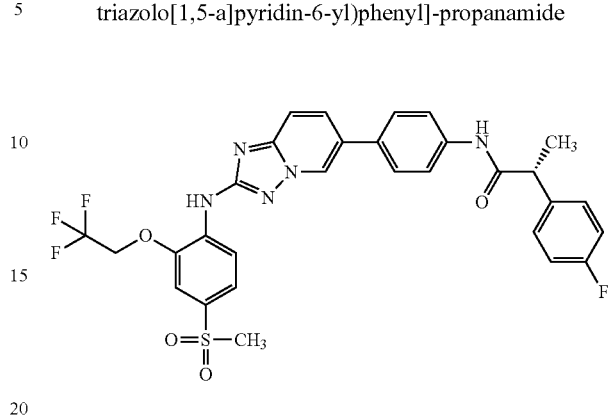

To a stirred suspension of Int08.021 (5.6 g) in DMF (45 mL) and dichloromethane (90 mL) was added sodium bicarbonate (1.97 g), (2R)-2-(4-fluorophenyl)propanoic acid (2.17 g) and HATU (6.69 g). The mixture was stirred at room temperature for 4 h. Water was added, and the mixture was stirred for 30 minutes. A half-saturated solution of sodium bicarbonate was added and the mixture was extracted with ethyl acetate. The organic phase was washed with saturated sodium chloride solution, dried (sodium sulfate) and the solvent was removed in vacuum. Aminophase-silica-gel chromatography gave a solid that was triturated with a mixture of ethyl acetate and cyclohexane to give 6.60 g of the title compound.

$^1$H-NMR (300 MHz, DMSO-$d_6$): δ [ppm]=1.39 (d, 3H), 3.17 (s, 3H), 3.83 (q, 1H), 5.00 (q, 2H), 7.08-7.19 (m, 2H), 7.35-7.45 (m, 2H), 7.58-7.76 (m, 7H), 7.93 (dd, 1H), 8.50 (d, 1H), 8.59 (s, 1H), 9.11 (d, 1H), 10.19 (s, 1H).

$[α]_D^{20}$: −69.3° (in DMSO).

Column: Chiralcel OD-RH 150×4.6; Flow: 1.00 mL/min; Solvent: A: Water with 0.1% formic acid, B: Acetonitrile; Solvent mixture: 40% A+60% B. Run Time: 20 min. Retention Time: 12.28 min; UV 254 nm; Enantiomeric Ratio: <1%:>99%.

Racemate01.03.r 2-(4-fluorophenyl)-N-[4-(2-{[4-(methylsulfonyl)-2-(2,2,2-trifluoroethoxy)-phenyl]amino}[1,2,4]triazolo[1,5-a]pyridin-6-yl)phenyl]propanamide

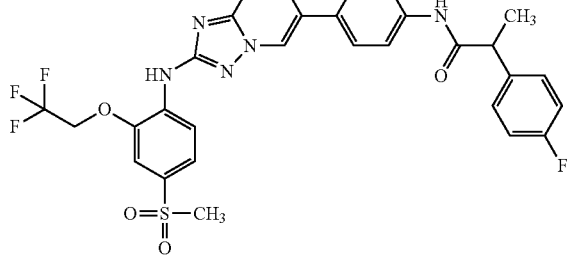

Starting with Int01.05 and Int05.03, Racemate01.03.r was prepared analogously to the procedure for the preparation of Int08.020.

Example01.04

4-{[6-(4-{[(2R)-2-(4-fluorophenyl)propanoyl]amino}phenyl)[1,2,4]-triazolo[1,5-a]pyridin-2-yl]amino}-3-methoxy-N-(2,2,2-trifluoro-ethyl)benzamide

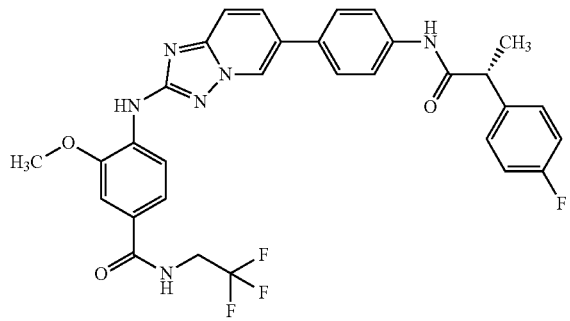 [SMILES: COc1cc(C(=O)NCC(F)(F)F)ccc1Nc1nc2ccc(-c3ccc(NC(=O)[C@H](C)c4ccc(F)cc4)cc3)cn2n1]

To a stirred suspension of Int08.031 (500 mg) in DMF (4.3 mL) and dichloromethane (8.6 mL) was added sodium bicarbonate (184 mg), (2R)-2-(4-fluorophenyl)propanoic acid (203 mg) and HATU (625 mg). The mixture was stirred at room temperature for 4 h. Water was added, and the mixture was stirred for 30 minutes. A half-saturated solution of sodium bicarbonate was added and the mixture was extracted with a mixture of dichloromethane and methanol (100:1). The organic phase was washed with saturated sodium chloride solution, dried (sodium sulfate) and the solvent was removed in vacuum. Aminophase-silica-gel chromatography gave a solid that was triturated with warm ethanol to give 300 mg of the title compound.

$^1$H-NMR (300 MHz, DMSO-$d_6$): δ [ppm]=1.39 (d, 3H), 3.83 (q, 1H), 3.92 (s, 3H), 3.99-4.16 (m, 2H), 7.09-7.18 (m, 2H), 7.36-7.44 (m, 2H), 7.51-7.60 (m, 2H), 7.62-7.76 (m, 5H), 7.91 (dd, 1H), 8.30-8.40 (m, 2H), 8.90 (t, 1H), 9.11 (d, 1H), 10.18 (s, 1H).

[α]$_D^{20}$: −70.5° (in DMSO).

Column: Chiralpak IA 5µ 150×4.6; Flow: 1.00 mL/min; Solvent: A: Ethanol, B: Methanol; Solvent mixture: 50% A+50% B. Run Time: 20 min. Retention Time: 6.67 min; UV 254 nm; Enantiomeric Ratio: <2%:>98%.

Racemate01.04.r

4-{[6-(4-{[2-(4-fluorophenyl)propanoyl]amino}phenyl)[1,2,4]triazolo[1,5-a]pyridin-2-yl]amino}-3-methoxy-N-(2,2,2-trifluoroethyl)benzamide

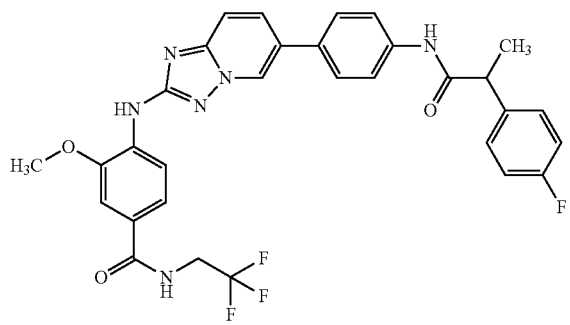 [SMILES: COc1cc(C(=O)NCC(F)(F)F)ccc1Nc1nc2ccc(-c3ccc(NC(=O)C(C)c4ccc(F)cc4)cc3)cn2n1]

Starting with Int01.05 and Int02.03, Racemate01.04.r was prepared analogously to the procedure for the preparation of Int08.020.

Example01.05

4-{[6-(4-{[2R)-2-(4-fluorophenyl)propanoyl]amino}phenyl)[1,2,4]-triazolo[1,5-a]pyridin-2-yl]amino}-3-methoxybenzamide

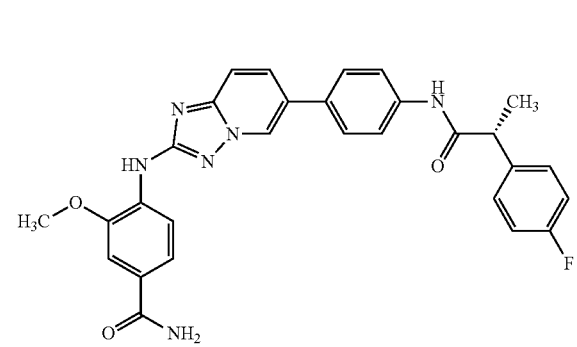 [SMILES: COc1cc(C(N)=O)ccc1Nc1nc2ccc(-c3ccc(NC(=O)[C@H](C)c4ccc(F)cc4)cc3)cn2n1]

To a stirred suspension of Int08.041 (65 mg) in DMF (0.5 mL) and dichloromethane (1.0 mL) was added sodium bicarbonate (44 mg), (2R)-2-(4-fluorophenyl)propanoic acid (32 mg) and HATU (99 mg). The mixture was stirred at room temperature for 2 h. Water was added, and the mixture was stirred for 30 minutes. A half-saturated solution of sodium bicarbonate was added and the mixture was extracted with ethyl acetate. The organic phase was washed with saturated sodium chloride solution, dried (sodium sulfate) and the solvent was removed in vacuum. Aminophase-silica-gel chromatography gave a solid that was triturated with dichloromethane to give 78 mg of the title compound.

$^1$H-NMR (400 MHz, DMSO-$d_6$): δ [ppm]=1.42 (d, 3H), 3.86 (q, 1H), 3.93 (s, 3H), 7.12-7.22 (m, 3H), 7.39-7.46 (m, 2H), 7.51-7.59 (m, 2H), 7.63-7.68 (m, 1H), 7.68-7.77 (m, 4H), 7.85 (br. s., 1H), 7.92 (dd, 1H), 8.26 (s, 1H), 8.33 (d, 1H), 9.13 (d, 1H), 10.19 (s, 1H).

Column: Chiralcel OD-RH 150×4.6; Flow: 1.00 mL/min; Solvent: A: Water with 0.1% formic acid, B: Acetonitrile; Solvent mixture: 50% A+50% B. Run Time: 30 min. Retention Time: 14.34 min; UV 254 nm; Enantiomeric Ratio: <1%:>99%.

Racemate01.05.r

4-{[6-(4-{[2-(4-fluorophenyl)propanoyl]amino}phenyl)[1,2,4]triazolo[1,5-a]pyridin-2-yl]amino}-3-methoxybenzamide

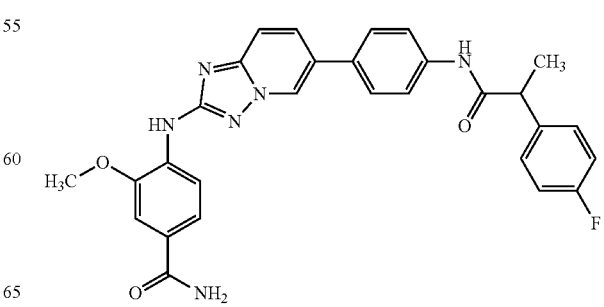

Starting with Int01.05 and 4-bromo-3-methoxybenzamide, Racemate01.05.r was prepared analogously to the procedure for the preparation of Int08.020.

Example01.06

4-{[6-(4-{[(2R)-2-(4-fluorophenyl)propanoyl]amino}phenyl)[1,2,4]triazolo-[1,5-a]pyridin-2-yl]amino}-3-(2,2,2-trifluoroethoxyl)benzamide

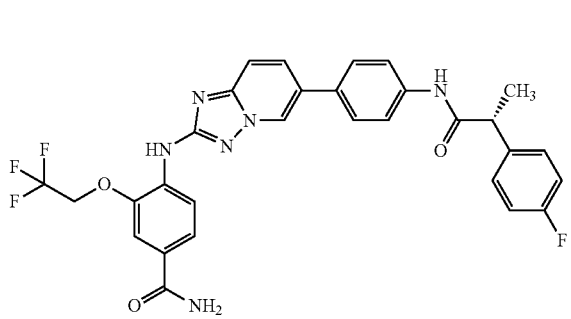 [SMILES: C[C@@H](C(=O)Nc1ccc(-c2ccc3nc(Nc4ccc(C(N)=O)cc4OCC(F)(F)F)nn3c2)cc1)c1ccc(F)cc1]

To a stirred suspension of Int08.051 (70 mg) in DMF (0.5 mL) and dichloromethane (1.0 mL) was added sodium bicarbonate (27 mg), (2R)-2-(4-fluorophenyl)propanoic acid (32 mg) and HATU (90 mg). The mixture was stirred at room temperature for 4 h. Water was added, and the mixture was stirred for 30 minutes. A half-saturated solution of sodium bicarbonate was added and the mixture was extracted with a mixture of dichloromethane and methanol (100:1). The organic phase was washed with saturated sodium chloride solution, dried (sodium sulfate) and the solvent was removed in vacuum. Aminophase-silica-gel chromatography gave a solid that was recrystallized from ethyl acetate to give 80 mg of the title compound.

$^1$H-NMR (400 MHz, DMSO-d$_6$): δ [ppm]=1.40 (d, 3H), 3.84 (q, 1H), 4.88 (q, 2H), 7.09-7.17 (m, 2H), 7.23 (br. s., 1H), 7.36-7.44 (m, 2H), 7.59-7.74 (m, 7H), 7.81 (br. s., 1H), 7.91 (dd, 1H), 8.20 (s, 1H), 8.33 (d, 1H), 9.11 (d, 1H), 10.16 (s, 1H).

$[α]_D^{20}$: −56.4° (in DMSO).

Column: Chiralpak IA 5µ 150×4.6; Flow: 1.00 mL/min; Solvent: A: Ethanol, B: Methanol; Solvent mixture: 50% A+50% B. Run Time: 20 min. Retention Time: 5.98 min; UV 254 nm; Enantiomeric Ratio: <1%:>99%.

Racemate01.06.r

4-{[6-(4-{[2-(4-fluorophenyl)propanoyl]amino}phenyl)[1,2,4]triazolo[1,5-a]pyridin-2-yl]amino}-3-(2,2,2-trifluoroethoxyl)benzamide

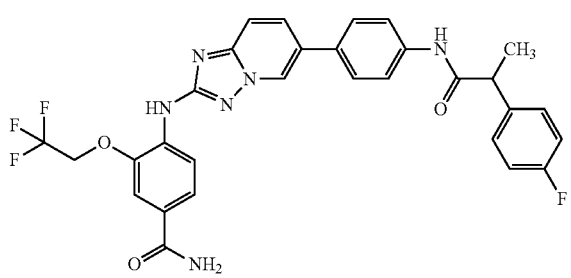 [SMILES: CC(C(=O)Nc1ccc(-c2ccc3nc(Nc4ccc(C(N)=O)cc4OCC(F)(F)F)nn3c2)cc1)c1ccc(F)cc1]

Starting with Int01.05 and Int06.03, Racemate01.06.r was prepared analogously to the procedure for the preparation of Int08.020.

Example01.07

(2R)—N-{4-[2-({4-[(3-fluoroazetidin-1-yl)carbonyl]-2-methoxyphenyl}amino)-[1,2,4]triazolo[1,5-a]pyridin-6-yl]phenyl}-2-(4-fluorophenyl)propanamide

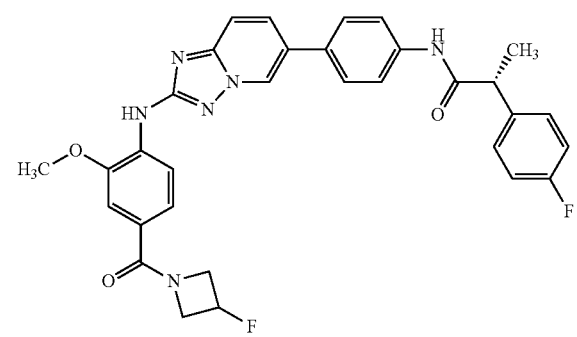 [SMILES: COc1cc(C(=O)N2CC(F)C2)ccc1Nc1nc2ccc(-c3ccc(NC(=O)[C@H](C)c4ccc(F)cc4)cc3)cn2n1]

To a stirred suspension of Int08.061 (1.10 g) in DMF (8.5 mL) and dichloromethane (17 mL) was added sodium bicarbonate (427 mg), (2R)-2-(4-fluorophenyl)propanoic acid (470 mg) and HATU (1.45 g). The mixture was stirred at room temperature for 4 h. Water was added, and the mixture was stirred for 30 minutes. A half-saturated solution of sodium bicarbonate was added and the mixture was extracted with ethyl acetate. The organic phase was washed with saturated sodium chloride solution, dried (sodium sulfate) and the solvent was removed in vacuum. Aminophase-silica-gel chromatography gave 1.13 g of the title compound.

$^1$H-NMR (400 MHz, DMSO-d$_6$): δ [ppm]=1.42 (d, 3H), 3.86 (q, 1H), 3.93 (s, 3H), 3.98-4.80 (m, 4H), 5.44 (m, 1H, J=57.5 Hz), 7.12-7.20 (m, 2H), 7.26 (d, 1H), 7.30 (dd, 1H), 7.40-7.46 (m, 2H), 7.63-7.76 (m, 5H), 7.93 (dd, 1H), 8.31-8.39 (m, 2H), 9.11 (d, 1H), 10.19 (s, 1H).

$[α]_D^{20}$: −70.0° (in DMSO).

Column: Chiralcel OD-RH 150×4.6; Flow: 1.00 mL/min; Solvent: A: Water with 0.1% formic acid, B: Acetonitrile; Solvent mixture: 40% A+60% B. Run Time: 20 min. Retention Time: 13.88 min; UV 254 nm; Enantiomeric Ratio: <1%:>99%.

Racemate01.07.r

N-{4-[2-({4-[(3-fluoroazetidin-1-yl)carbonyl]-2-methoxyphenyl}amino)-[1,2,4]triazolo[1,5-a]pyridin-6-yl]phenyl}-2-(4-fluorophenyl)propanamide

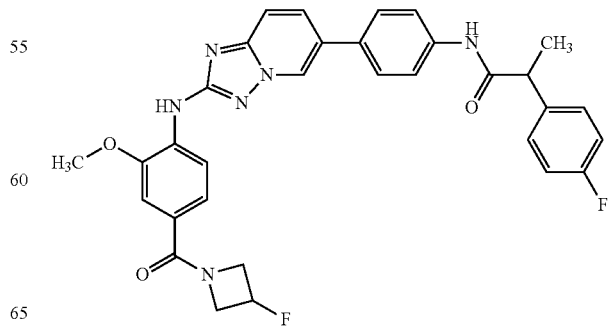

Starting with Int01.05 and Int02.05, Racemate01.07.r was prepared analogously to the procedure for the preparation of Int08.020.

Example01.08

(2R)—N-[4-(2-{[4-(azetidin-1-ylcarbonyl)-2-methoxyphenyl]amino}[1,2,4]-triazolo[1,5-a]pyridin-6-yl)phenyl]-2-(4-fluorophenyl)propanamide

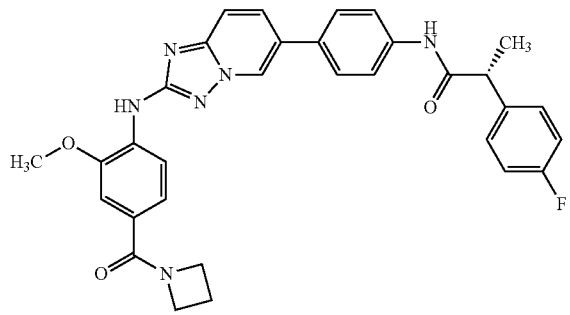 [SMILES: COc1cc(C(=O)N2CCC2)ccc1Nc1nc2ccc(-c3ccc(NC(=O)[C@H](C)c4ccc(F)cc4)cc3)cn2n1]

To a stirred suspension of Int08.071 (200 mg) in DMF (1.6 mL) and dichloromethane (3.2 mL) was added sodium bicarbonate (122 mg), (2R)-2-(4-fluorophenyl)propanoic acid (89 mg) and HATU (275 mg). The mixture was stirred at room temperature for 4 h. Water was added, and the mixture was stirred for 30 minutes. A half-saturated solution of sodium bicarbonate was added and the mixture was extracted with a mixture of dichloromethane and methanol (100:1). The organic phase was washed with saturated sodium chloride solution, dried (sodium sulfate) and the solvent was removed in vacuum. Aminophase-silica-gel chromatography followed by silica gel chromatography gave a solid that was triturated with ether to give 250 mg of the title compound.

$^1$H-NMR (300 MHz, DMSO-d$_6$): δ [ppm]=1.39 (d, 3H), 2.22 (quin, 2H), 3.78-3.92 (m, 4H), 4.00 (br. s., 2H), 4.32 (br. s, 2H), 7.09-7.17 (m, 2H), 7.20-7.26 (m, 2H), 7.36-7.44 (m, 2H), 7.59-7.75 (m, 5H), 7.89 (dd, 1H), 8.24-8.36 (m, 2H), 9.08 (d, 1H), 10.18 (s, 1H).

$[α]_D^{20}$: −63.5° (in DMSO).

Column: Chiralcel OD-RH 150×4.6; Flow: 1.00 mL/min; Solvent: A: Water with 0.1% formic acid, B: Acetonitrile; Solvent mixture: 40% A+60% B. Run Time: 30 min. Retention Time: 14.22 min; UV 254 nm; Enantiomeric Ratio: <2%:>98%.

Racemate01.08.r

N-[4-(2-{[4-(azetidin-1-ylcarbonyl)-2-methoxyphenyl]amino}[1,2,4]-triazolo[1,5-a]pyridin-6-yl)phenyl]-2-(4-fluorophenyl)propanamide

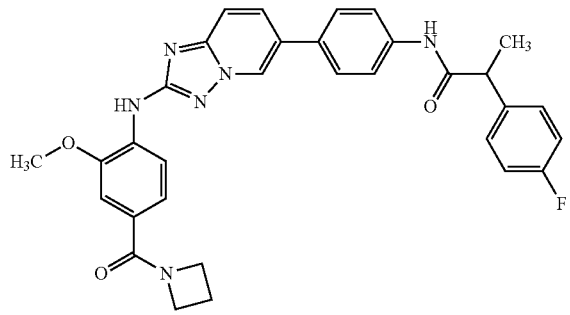 [SMILES: COc1cc(C(=O)N2CCC2)ccc1Nc1nc2ccc(-c3ccc(NC(=O)C(C)c4ccc(F)cc4)cc3)cn2n1]

Starting with Int01.05 and Int02.04, Racemate01.08.r was prepared analogously to the procedure for the preparation of Int08.020.

Example01.09

(2R)-2-(4-fluorophenyl)-N-[4-(2-{[2-methoxy-4-(2-oxo-1,3-oxazolidin-3-yl)phenyl]amino}[1,2,4]triazolo[1,5-a]pyridin-6-yl)phenyl]propanamide

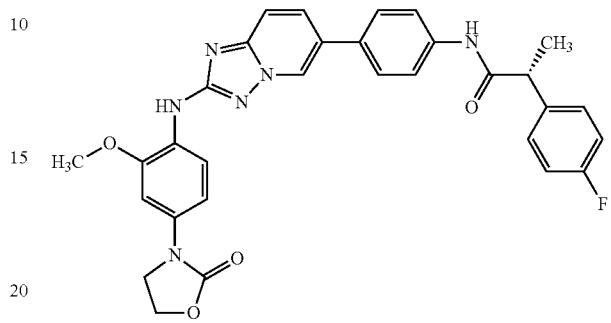

To a stirred suspension of Int08.081 (100 mg) in DMF (0.8 mL) and dichloromethane (1.6 mL) was added sodium bicarbonate (41 mg), (2R)-2-(4-fluorophenyl)propanoic acid (44 mg) and HATU (137 mg). The mixture was stirred at room temperature for 16 h. Water was added, and the mixture was stirred for 30 minutes. A half-saturated solution of sodium bicarbonate was added and the mixture was extracted with a mixture of dichloromethane and methanol (100:1). The organic phase was washed with saturated sodium chloride solution, dried (sodium sulfate) and the solvent was removed in vacuum. Aminophase-silica-gel chromatography gave a solid that was triturated with ethyl acetate to give 85 mg of the title compound.

$^1$H-NMR (400 MHz, DMSO-d$_6$): δ [ppm]=1.39 (d, 3H), 3.77-3.89 (m, 4H), 4.04 (dd, 2H), 4.36-4.45 (m, 2H), 6.98 (dd, 1H), 7.10-7.16 (m, 2H), 7.36-7.43 (m, 3H), 7.54-7.59 (m, 1H), 7.63-7.72 (m, 4H), 7.85 (dd, 1H), 7.97 (s, 1H), 8.13 (d, 1H), 8.97-9.07 (m, 1H), 10.15 (s, 1H).

$[α]_D^{20}$: −72.1° (in DMSO).

Column: Chiralpak IB 5μ 150×4.6; Flow: 1.00 mL/min; Solvent: A: Ethanol, B: Methanol; Solvent mixture: 50% A+50% B. Run Time: 20 min. Retention Time: 5.74 min; UV 254 nm; Enantiomeric Ratio: <1%:>99%.

Racemate01.09.r 2-(4-fluorophenyl)-N-[4-(2-{[2-methoxy-4-(2-oxo-1,3-oxazolidin-3-yl)-phenyl]amino}[1,2,4]triazolo[1,5-a]pyridin-6-yl)phenyl]propanamide

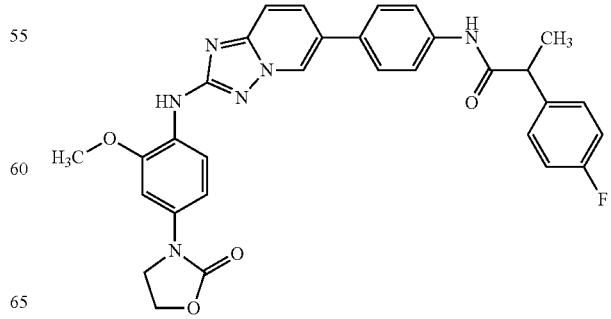

Starting with Int01.05 and Int07.01, Racemate01.09.r was prepared analogously to the procedure for the preparation of Int08.020.

Racemate01.10.r 2-(4-fluorophenyl)-3-hydroxy-N-[4-(2-{[4-(methyl-sulfonyl)-2-(2,2,2-tri-fluoroethoxy)phenyl]amino}[1,2,4]triazolo[1,5-a]pyridin-6-yl)phenyl]-propanamide

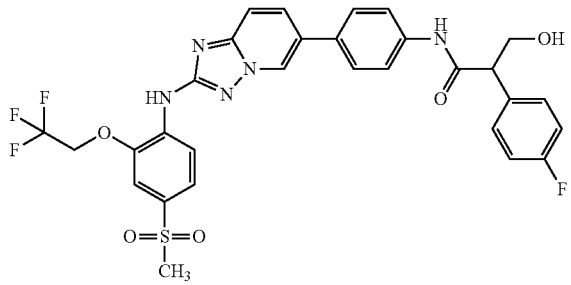 [SMILES: CS(=O)(=O)c1ccc(Nc2nc3ccc(-c4ccc(NC(=O)C(CO)c5ccc(F)cc5)cc4)cn3n2)c(OCC(F)(F)F)c1]

To a stirred solution of Int08.143 (340 mg) in tetrahydrofurane (20 mL) was added a solution of TBAF in THF (0.77 mL; c=1.0 M). The mixture was stirred at room temperature for 1 h. Water was added and the reaction mixture was extracted with ethyl acetate. The organic phase was washed with saturated sodium chloride solution, dried (sodium sulfate) and the solvent was removed in vacuum. Aminophase-silica-gel chromatography gave 193 mg of the title compound.

Example01.10

(−)-2-(4-fluorophenyl)-3-hydroxy-N-[4-(2-{[4-(methylsulfonyl)-2-(2,2,2-tri-fluoroethoxy)phenyl]amino}[1,2,4]triazolo[1,5-a]pyridin-6-yl)phenyl]-propanamide

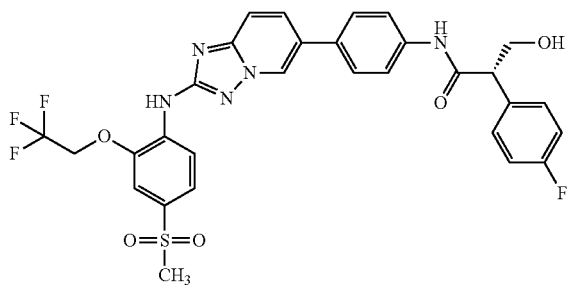 [SMILES: CS(=O)(=O)c1ccc(Nc2nc3ccc(-c4ccc(NC(=O)[C@H](CO)c5ccc(F)cc5)cc4)cn3n2)c(OCC(F)(F)F)c1]

The enantiomers of 176 mg of Racemate01.10.r were separated using chiral HPLC. Column: Chiralpak IB 5μ 250×20 mm; Flow: 20.0 mL/min; Solvent: A: Hexane, B: Ethanol; Solvent mixture: 50% A+50% B. Retention time of the titel compound: 9.7-11.1 min (Peak 1). Yield: 75 mg.

$^1$H-NMR (400 MHz, DMSO-d$_6$): δ [ppm]=3.18 (s, 3H), 3.50-3.60 (m, 1H), 3.81-3.90 (m, 1H), 3.98-4.08 (m, 1H), 4.92-5.08 (m, 3H), 7.10-7.19 (m, 2H), 7.36-7.45 (m, 2H), 7.59-7.77 (m, 7H), 7.95 (dd, 1H), 8.52 (d, 1H), 8.58 (s, 1H), 9.13 (d, 1H), 10.26 (s, 1H).

$[α]_D^{20}$: −72.9° (in DMSO).

Column: Chiralpak IB 5μ 150×4.6; Flow: 1.00 mL/min; Solvent: A: Hexane, B: Ethanol; Solvent mixture: 50% A+50% B. Run Time: 30 min. Retention Time: 6.80 min; UV 254 nm; Enantiomeric Ratio: >99%:<1%.

Example01.11

(2R)-2-amino-2-(4-fluorophenyl)-N-[4-(2-{[2-methoxy-4-(methylsulfonyl)-phenyl]amino}[1,2,4]triazolo[1,5-a]pyridin-6-yl)phenyl]ethanamide

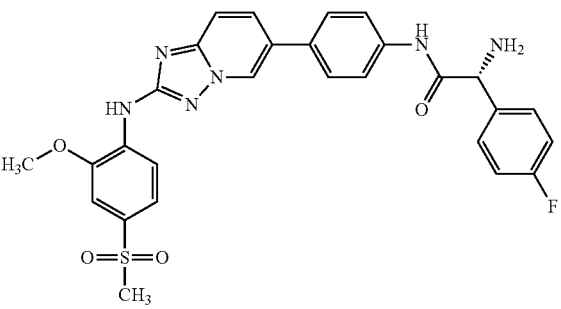 [SMILES: COc1cc(S(C)(=O)=O)ccc1Nc1nc2ccc(-c3ccc(NC(=O)[C@H](N)c4ccc(F)cc4)cc3)cn2n1]

To a stirred solution of Int08.150 (260 mg) in dichloromethane (16 mL) was added TFA (0.76 mL). The mixture was stirred at room temperature for 2 h. Further TFA was added (1 mL) and the mixture was stirred at room temperature for 72 h. A half-saturated solution of potassium carbonate was added until pH 9 was reached. The mixture was extracted with dichloromethane and methanol (10:1 mixture). The solution was filtered through an aminophase-silica-gel column. The solvent was removed in vacuum to give a solid that was recrystallized from ethanol to give 210 mg of the title compound.

$^1$H-NMR (300 MHz, DMSO-d$_6$, detected signals): δ [ppm]=3.16 (s, 3H), 3.95 (s, 3H), 4.53 (s, 1H), 7.08-7.19 (m, 2H), 7.42 (d, 1H), 7.45-7.55 (m, 3H), 7.67 (d, 1H), 7.73 (br. s, 4H), 7.93 (dd, 1H), 8.48 (d, 1H), 8.63 (s, 1H), 9.12 (d, 1H), 10.17 (br. s, 1H).

$[α]_D^{20}$: −43.1° (in DMSO).

Example01.12

4-{[6-(4-{[(2R)-2-(4-fluorophenyl)propanoyl]amino}phenyl)[1,2,4]triazolo[1,5-a]pyridin-2-yl]amino}-3-methoxy-N,N-dimethylbenzamide

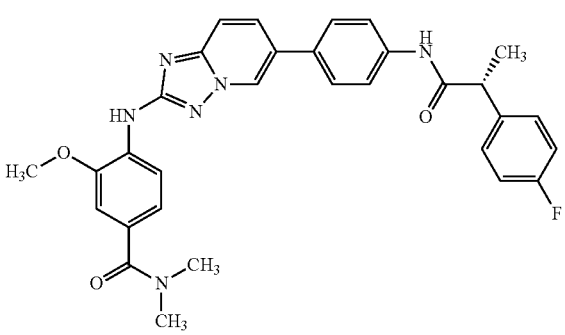 [SMILES: COc1cc(C(=O)N(C)C)ccc1Nc1nc2ccc(-c3ccc(NC(=O)[C@H](C)c4ccc(F)cc4)cc3)cn2n1]

Starting with Int08.091, Example01.12 was prepared analogously to the procedure for the preparation of Example01.04.

$^1$H-NMR (400 MHz, DMSO-d$_6$): δ [ppm]=1.40 (d, 3H), 2.95 (s, 6H), 3.83 (q, 1H), 3.88 (s, 3H), 6.99-7.06 (m, 2H), 7.10-7.17 (m, 2H), 7.37-7.43 (m, 2H), 7.59-7.64 (m, 1H), 7.65-7.74 (m, 4H), 7.89 (dd, 1H), 8.17 (s, 1H), 8.28 (d, 1H), 9.03-9.10 (m, 1H), 10.16 (s, 1H).

Example01.13

(2R)-2-(4-fluorophenyl)-N-[4-(2-{[2-methoxy-4-(pyrrolidin-1-ylcarbonyl)phenyl]amino}[1,2,4]triazolo[1,5-a]pyridin-6-yl)phenyl]propanamide

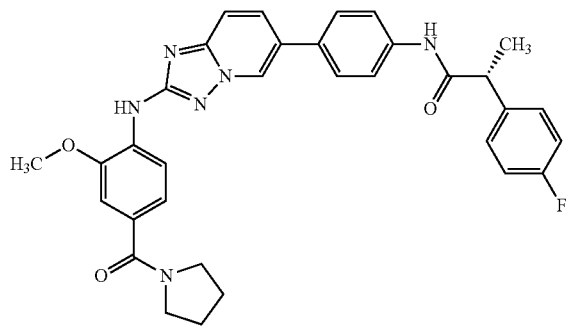 [SMILES: COc1cc(C(=O)N2CCCC2)ccc1Nc1nc2ccc(-c3ccc(NC(=O)[C@H](C)c4ccc(F)cc4)cc3)cn2n1]

Starting with Int08.101, Example01.13 was prepared analogously to the procedure for the preparation of Example01.08.

$^1$H-NMR (300 MHz, DMSO-d$_6$): δ [ppm]=1.39 (d, 3H), 1.80 (br. s., 4H), 3.45 (br. s., 4H), 3.79-3.85 (m, 1H), 3.88 (s, 3H), 7.08-7.19 (m, 4H), 7.40 (dd, 2H), 7.58-7.75 (m, 5H), 7.89 (dd, 1H), 8.21 (s, 1H), 8.28 (d, 1H), 9.08 (s, 1H), 10.17 (s, 1H).

[α]$_D^{20}$: −69.3° (in DMSO).

Example01.14

(2R)—N-{4-[2-({4-[(3-fluoroazetidin-1-yl)carbonyl]-2-(2,2,2-trifluoroethoxy)phenyl}amino)[1,2,4]triazolo[1,5-a]pyridin-6-yl]phenyl}-2-(4-fluorophenyl)propanamide

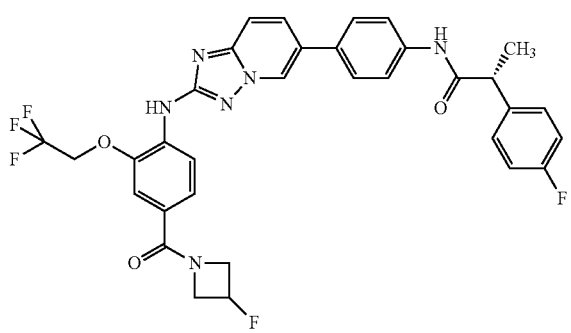 [SMILES: C[C@@H](C(=O)Nc1ccc(-c2ccc3nc(Nc4ccc(C(=O)N5CC(F)C5)cc4OCC(F)(F)F)nn3c2)cc1)c1ccc(F)cc1]

Starting with Int08.111, Example01.14 was prepared analogously to the procedure for the preparation of Example01.04.

$^1$H-NMR (300 MHz, DMSO-d$_6$): δ [ppm]=1.39 (d, 3H), 3.83 (q, 1H), 3.91-4.73 (m, 4H), 4.92 (d, 2H), 5.25-5.58 (m, 1H), 7.13 (t, 2H), 7.33-7.46 (m, 4H), 7.59-7.76 (m, 5H), 7.91 (dd, 1H), 8.27 (s, 1H), 8.32-8.40 (m, 1H), 9.10 (s, 1H), 10.18 (s, 1H).

[α]$_D^{20}$: −47.2° (in DMSO).

Example01.15

(2R)-2-(4-fluorophenyl)-N-{4-[2-({4-[(3-hydroxyazetidin-1-yl)carbonyl]-2-(2,2,2-trifluoroethoxy)phenyl}amino)[1,2,4]triazolo[1,5-a]pyridin-6-yl]phenyl}propanamide

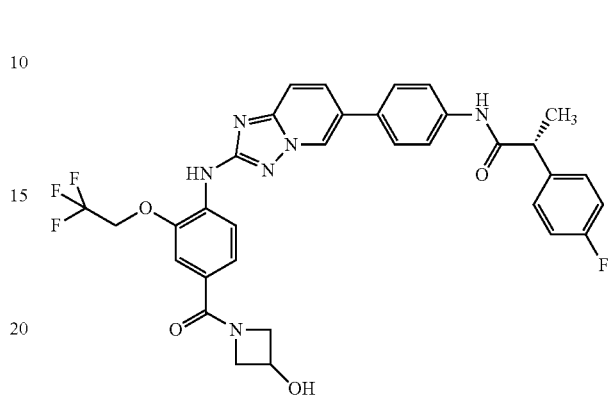

Starting with Int08.121, Example01.15 was prepared analogously to the procedure for the preparation of Example01.05.

$^1$H-NMR (300 MHz, DMSO-d$_6$): δ [ppm]=1.35-1.43 (m, 3H), 3.70-3.91 (m, 3H), 3.97-4.31 (m, 2H), 4.48 (br. s., 2H), 4.91 (q, 2H), 7.07-7.19 (m, 2H), 7.31-7.45 (m, 4H), 7.60-7.75 (m, 5H), 7.91 (dd, 1H), 8.21 (s, 1H), 8.34 (d, 1H), 9.08 (d, 1H), 10.16 (s, 1H).

Example01.16

(2R)-2-(4-fluorophenyl)-N-[4-(2-{[4-(pyrrolidin-1-ylcarbonyl)-2-(2,2,2-trifluoroethoxyl)phenyl]amino}[1,2,4]triazolo[1,5-a]pyridin-6-yl)phenyl]propanamide

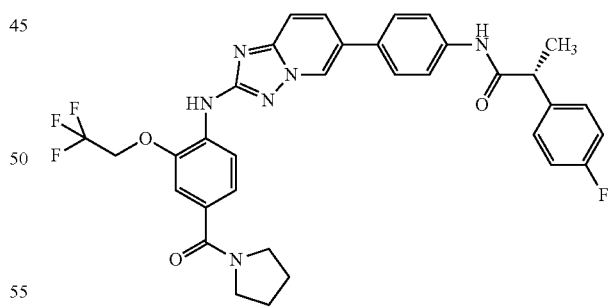

Starting with Int08.131, Example01.16 was prepared analogously to the procedure for the preparation of Example01.09.

$^1$H-NMR (300 MHz, DMSO-d$_6$): δ [ppm]=1.39 (d, 3H), 1.81 (br. s., 4H), 3.44 (d, 4H), 3.83 (q, 1H), 4.89 (q, 2H), 7.07-7.19 (m, 2H), 7.23-7.34 (m, 2H), 7.35-7.45 (m, 2H), 7.59-7.74 (m, 5H), 7.90 (dd, 1H), 8.15 (s, 1H), 8.31 (d, 1H), 9.09 (s, 1H), 10.18 (s, 1H).

[α]$_D^{20}$: ×69.6° (in DMSO).

Racemate01.17.r 2-(4-fluorophenyl)-3-hydroxy-N-[4-(2-{[2-methoxy-4-(methylsulfonyl)phenyl]amino}[1,2,4]triazolo[1,5-a]pyridin-6-yl)phenyl]propanamide

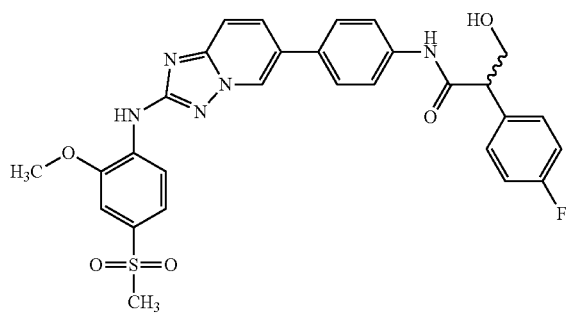 [SMILES: COc1cc(S(C)(=O)=O)ccc1Nc1nc2ccc(-c3ccc(NC(=O)C(CO)c4ccc(F)cc4)cc3)cn2n1]

Starting with Int08.144, Racemate01.17.r was prepared analogously to the procedure for the preparation of Racemate01.10.r.

Example01.17

(2S)-2-(4-fluorophenyl)-3-hydroxy-N-[4-(2-{[2-methoxy-4-(methylsulfonyl)phenyl]amino}[1,2,4]triazolo[1,5-a]pyridin-6-yl)phenyl]propanamide

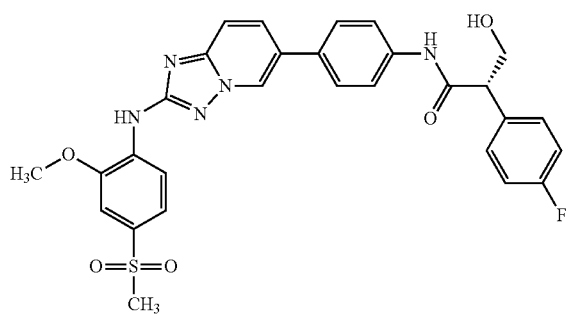

The enantiomers of 175 mg of Racemate01.17.r were separated using chiral HPLC. Column: Chiralpak IB 5μ 250×20 mm; Flow: 20.0 mL/min; Solvent: A: Hexane, B: Ethanol; Solvent mixture: 50% A+50% B. Retention time of the titel compound: 15.2-17.4 min (Peak 1). Yield: 71 mg.

$^1$H-NMR (300 MHz, DMSO-d$_6$): δ [ppm]=3.16 (s, 3H), 3.54 (dt, 1H), 3.84 (dd, 1H), 3.92-4.09 (m, 4H), 4.96 (t, 1H), 7.08-7.19 (m, 2H), 7.35-7.45 (m, 3H), 7.51 (dd, 1H), 7.63-7.77 (m, 5H), 7.92 (dd, 1H), 8.48 (d, 1H), 8.60 (s, 1H), 9.10 (d, 1H), 10.23 (s, 1H).

$[α]_D^{20}$: −59.6° (in DMSO).

Column: Chiralpak IB 5μ 150×4.6; Flow: 1.00 mL/min; Solvent: A: Hexane, B: Ethanol; Solvent mixture: 50% A+50% B. Run Time: 30 min. Retention Time: 10.75 min; UV 254 nm; Enantiomeric Ratio: 97.1%:2.9%.

Example01.18

(2S)—N-{4-[2-({4-[(3-fluoroazetidin-1-yl)carbonyl]-2-(2,2,2-trifluoroethoxyl)phenyl}amino)[1,2,4]triazolo[1,5-a]pyridin-6-yl]phenyl}-2-(4-fluorophenyl)-3-hydroxypropanamide

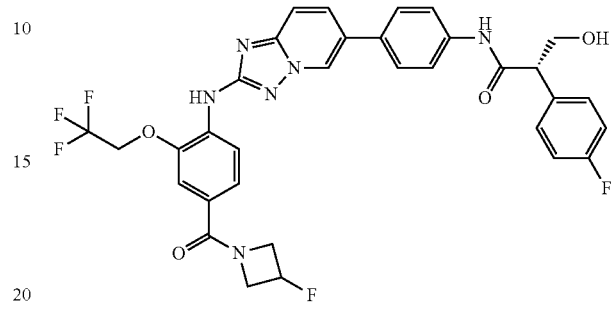

To a stirred solution of Int08.146 (290 mg) in tetrahydrofurane (18 mL) at 0° C. was added a solution of TBAF in THF (0.64 mL; c=1.0 M). The mixture was stirred at 0° C. for 30 minutes. A saturated solution of ammonium chloride was added and the reaction mixture was extracted with ethyl acetate. The organic phase was washed with saturated sodium chloride solution, dried (sodium sulfate) and the solvent was removed in vacuum. Aminophase-silica-gel chromatography gave a solid that was triturated with a mixture of dichloromethane and hexane to give 155 mg of the title compound.

$^1$H-NMR (300 MHz, DMSO-d$_6$): δ [ppm]=3.53 (dt, 1H), 3.83 (dd, 1H), 3.93-4.73 (m, 5H), 4.84-5.03 (m, 3H), 5.26-5.57 (m, 1H), 7.13 (t, 2H), 7.32-7.45 (m, 4H), 7.61-7.76 (m, 5H), 7.92 (dd, 1H), 8.27 (s, 1H), 8.33-8.41 (m, 1H), 9.10 (s, 1H), 10.25 (s, 1H).

$[α]_D^{20}$: −61.7° (in DMSO).

Column: Chiralpak IC 3 μm 100×4.6; Flow: 1.00 mL/min; Solvent: A: Ethanol; Solvent mixture: 100% A. Run Time: 30 min. Retention Time: 2.63 min; UV 280 nm; Enantiomeric Ratio: 97.3%:2.7%.

Example01.19

(2R)-2-amino-2-(4-fluorophenyl)-N-[4-(2-{[4-(methylsulfonyl)-2-(2,2,2-trifluoroethoxyl)phenyl]amino}[1,2,4]triazolo[1,5-a]pyridin-6-yl)phenyl]ethanamide

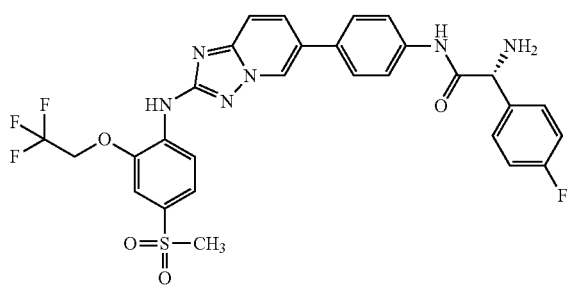 [SMILES: CS(=O)(=O)c1ccc(Nc2nc3ccc(-c4ccc(NC(=O)[C@H](N)c5ccc(F)cc5)cc4)cn3n2)c(OCC(F)(F)F)c1]

Starting with Int08.151, Example01.19 was prepared analogously to the procedure for the preparation of Example01.11.

¹H-NMR (400 MHz, DMSO-d₆ detected signals): δ [ppm]=3.17 (s, 3H), 4.54 (s, 1H), 5.00 (q, 2H), 7.10-7.18 (m, 2H), 7.45-7.53 (m, 2H), 7.59-7.65 (m, 2H), 7.68 (d, 1H), 7.73 (s, 4H), 7.94 (dd, 1H), 8.50 (d, 1H), 8.56 (s, 1H), 9.12 (d, 1H), 9.67-10.60 (br. s, 1H).

$[\alpha]_D^{20}$: −36.3° (in DMSO).

Example01.20

(2R)-2-amino-2-(4-fluorophenyl)-N-[4-(2-{[2-methoxy-4-(2-oxo-1,3-oxazolidin-3-yl)phenyl]amino}[1,2,4]triazolo[1,5-a]pyridin-6-yl)phenyl]ethanamide

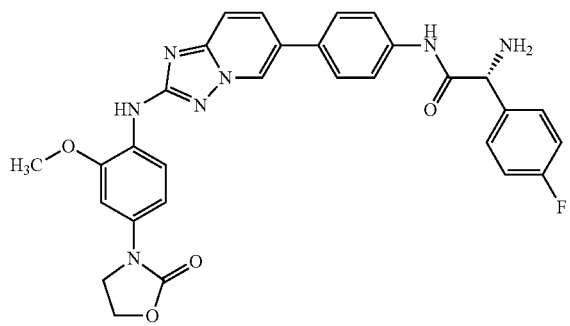 [SMILES: COc1cc(N2CCOC2=O)ccc1Nc1nc2ccc(-c3ccc(NC(=O)[C@H](N)c4ccc(F)cc4)cc3)cn2n1]

Starting with Int08.152, Example01.20 was prepared analogously to the procedure for the preparation of Example01.11.

¹H-NMR (400 MHz, DMSO-d₆ detected signals): δ [ppm]=3.84 (s, 3H), 4.04 (dd, 2H), 4.33-4.45 (m, 2H), 4.54 (s, 1H), 6.98 (dd, 1H), 7.08-7.18 (m, 2H), 7.39 (d, 1H), 7.45-7.52 (m, 2H), 7.57 (d, 1H), 7.67-7.77 (m, 4H), 7.86 (dd, 1H), 7.97 (s, 1H), 8.13 (d, 1H), 9.03 (d, 1H), 10.16 (br. s., 1H).

$[\alpha]_D^{20}$: −42.5° (in DMSO).

Example01.21

(2R)-2-amino-N-{4-[2-({4-[(3-fluoroazetidin-1-yl)carbonyl]-2-methoxyphenyl}amino)[1,2,4]triazolo[1,5-a]pyridin-6-yl]phenyl}-2-(4-fluorophenyl)ethanamide

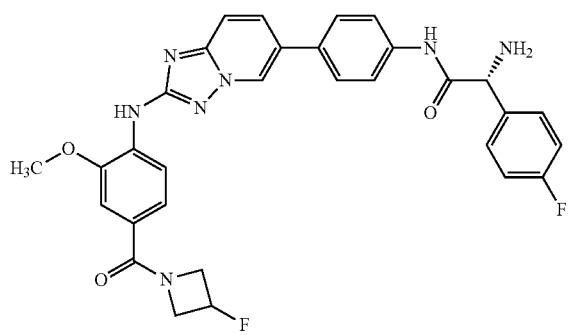 [SMILES: COc1cc(C(=O)N2CC(F)C2)ccc1Nc1nc2ccc(-c3ccc(NC(=O)[C@H](N)c4ccc(F)cc4)cc3)cn2n1]

Starting with Int08.153, Example01.21 was prepared analogously to the procedure for the preparation of Example01.11.

¹H-NMR (300 MHz, DMSO-d₆ detected signals): δ [ppm]=3.90 (s, 3H), 4.03-4.75 (m, 5H), 5.23-5.60 (m, 1H), 7.14 (t, 2H), 7.19-7.32 (m, 2H), 7.49 (dd, 2H), 7.64 (d, 1H), 7.72 (s, 4H), 7.91 (d, 1H), 8.25-8.42 (m, 2H), 9.09 (s, 1H), 9.69-10.77 (br. s, 1H).

$[\alpha]_D^{20}$: −38.2° (in DMSO).

Example01.22

(2R)-2-amino-N-[4-(2-{[4-(azetidin-1-ylcarbonyl)-2-methoxyphenyl]amino}[1,2,4]triazolo[1,5-a]pyridin-6-yl)phenyl]-2-(4-fluorophenyl)ethanamide

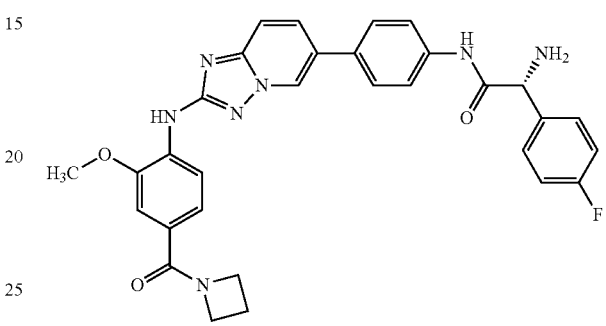

Starting with Int08.154, Example01.22 was prepared analogously to the procedure for the preparation of Example01.11.

¹H-NMR (300 MHz, DMSO-d₆ detected signals): δ [ppm]=2.23 (quin, 2H), 3.89 (s, 3H), 4.00 (br. s., 2H), 4.25-4.42 (m, 2H), 4.54 (s, 1H), 7.07-7.18 (m, 2H), 7.19-7.28 (m, 2H), 7.49 (dd, 2H), 7.63 (d, 1H), 7.72 (s, 4H), 7.90 (dd, 1H), 8.26 (s, 1H), 8.31 (d, 1H), 9.08 (d, 1H), 10.19 (br. s, 1H).

$[\alpha]_D^{20}$: −43.8° (in DMSO).

Example01.23

(2R)-2-amino-2-(4-fluorophenyl)-N-[4-(2-{[2-methoxy-4-(pyrrolidin-1-ylcarbonyl)phenyl]amino}[1,2,4]triazolo[1,5-a]pyridin-6-yl)phenyl]ethanamide

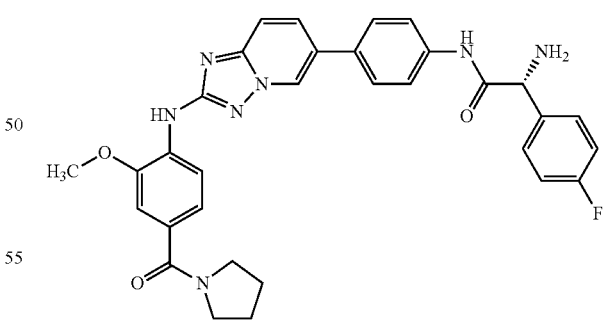

Starting with Int08.155, Example01.23 was prepared analogously to the procedure for the preparation of Example01.11.

¹H-NMR (400 MHz, DMSO-d₆ detected signals): δ [ppm]=1.80 (br. s., 4H), 3.45 (br. s., 4H), 3.88 (s, 3H), 4.53 (s, 1H), 7.05-7.20 (m, 4H), 7.43-7.55 (m, 2H), 7.62 (d, 1H), 7.72 (s, 4H), 7.90 (dd, 1H), 8.19 (s, 1H), 8.29 (d, 1H), 9.09 (d, 1H), 9.65-10.60 (br. s, 1H).

$[\alpha]_D^{20}$: −40.5° (in DMSO).

Example01.24

(2R)-2-amino-N-{4-[2-({4-[(3-fluoroazetidin-1-yl)carbonyl]-2-(2,2,2-trifluoroethoxy)phenyl}amino)[1,2,4]triazolo[1,5-a]pyridin-6-yl]phenyl}-2-(4-fluorophenyl)ethanamide

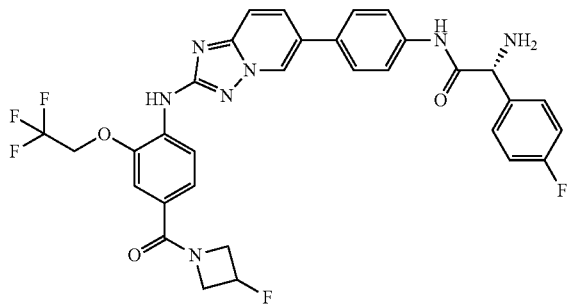 [SMILES: N[C@@H](C(=O)Nc1ccc(-c2ccc3nc(Nc4ccc(C(=O)N5CC(F)C5)cc4OCC(F)(F)F)nn3c2)cc1)c1ccc(F)cc1]

Starting with Int08.156, Example01.24 was prepared analogously to the procedure for the preparation of Example01.11.

$^1$H-NMR (400 MHz, DMSO-$d_6$ detected signals): δ [ppm]=3.95-4.70 (m, 5H), 4.92 (q, 2H), 5.29-5.55 (m, 1H), 7.14 (t, 2H), 7.33-7.44 (m, 2H), 7.49 (dd, 2H), 7.65 (d, 1H), 7.72 (s, 4H), 7.92 (dd, 1H), 8.25 (s, 1H), 8.37 (d, 1H), 9.10 (s, 1H), 10.17 (br. s, 1H).

$[\alpha]_D^{20}$: −32.5° (in DMSO).

Example01.25

(2R)-2-amino-2-(4-fluorophenyl)-N-[4-(2-{[4-(pyrrolidin-1-ylcarbonyl)-2-(2,2,2-trifluoroethoxy)phenyl]amino}[1,2,4]triazolo[1,5-a]pyridin-6-yl)phenyl]ethanamide

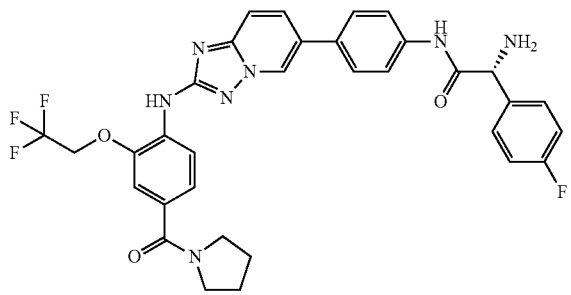 [SMILES: N[C@@H](C(=O)Nc1ccc(-c2ccc3nc(Nc4ccc(C(=O)N5CCCC5)cc4OCC(F)(F)F)nn3c2)cc1)c1ccc(F)cc1]

Starting with Int08.157, Example01.25 was prepared analogously to the procedure for the preparation of Example01.11.

$^1$H-NMR (300 MHz, DMSO-$d_6$ detected signals): δ [ppm]=1.81 (br. s., 4H), 3.44 (d, 4H), 4.53 (s, 1H), 4.89 (q, 2H), 7.14 (t, 2H), 7.22-7.34 (m, 2H), 7.49 (dd, 2H), 7.63 (d, 1H), 7.72 (s, 4H), 7.91 (dd, 1H), 8.15 (s, 1H), 8.31 (d, 1H), 9.10 (s, 1H), 10.13 (br. s, 1H).

$[\alpha]_D^{20}$: −38.8° (in DMSO).

Further, the compounds of formula (I) of the present invention can be converted to any salt as described herein, by any method which is known to the person skilled in the art. Similarly, any salt of a compound of formula (I) of the present invention can be converted into the free compound, by any method which is known to the person skilled in the art.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives.

Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science Et Technology 1999, 53(6), 324-349; and Nema, S. et al., "Excipients and Their Use in Injectable Products" PDA Journal of Pharmaceutical Science Et Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);
tablet anti-adherents (examples include but are not limited to magnesium stearate and talc);
tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);
tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);
tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);
tablet direct compression excipients (examples include but are not limited to dibasic calcium phosphate);
tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);
tablet glidants (examples include but are not limited to colloidal silica, corn starch and talc);
tablet lubricants (examples include but are not limited to calcium stearate, magnesium stearate, mineral oil, stearic acid and zinc stearate);
tablet/capsule opaquants (examples include but are not limited to titanium dioxide);
tablet polishing agents (examples include but are not limited to carnuba wax and white wax);
thickening agents (examples include but are not limited to beeswax, cetyl alcohol and paraffin);
tonicity agents (examples include but are not limited to dextrose and sodium chloride);
viscosity increasing agents (examples include but are not limited to alginic acid, bentonite, carbomers, carboxymethylcellulose sodium, methylcellulose, polyvinyl pyrrolidone, sodium alginate and tragacanth); and
wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:
Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.
Lyophilised powder for IV administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.
Intramuscular suspension: The following solution or suspension can be prepared, for intramuscular injection:
50 mg/mL of the desired, water-insoluble compound of this invention
5 mg/mL sodium carboxymethylcellulose
4 mg/mL TWEEN 80
9 mg/mL sodium chloride
9 mg/mL benzyl alcohol
Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.
Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.
Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.
Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, toposisomerase inhibitors, biological response modifiers, or anti-hormones.

Preferred additional pharmaceutical agents are: 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, BAY 86-9766 (RDEA 119), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, raloxifene, raltitrexed, ranimustine, razoxane, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

Optional anti-hyper-proliferative agents which can be added to the composition include but are not limited to compounds listed on the cancer chemotherapy drug regimens in the 11$^{th}$ Edition of the Merck Index, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

The compounds of the invention may also be administered in combination with protein therapeutics. Such protein therapeutics suitable for the treatment of cancer or other angiogenic disorders and for use with the compositions of the invention include, but are not limited to, an interferon (e.g., interferon .alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatumumab, SGN-40, pertuzumab, EMD-273063, L19-IL-2 fusion protein, PRX-321, CNTO-328, MDX-214, tigapotide, CAT-3888, labetuzumab, alpha-particle-emitting radioisotope-linked lintuzumab, EM-1421, HyperAcute vaccine, tucotuzumab celmoleukin, galiximab, HPV-16-E7, Javelin—prostate cancer, Javelin—melanoma, NY-ESO-1 vaccine, EGF vaccine, CYT-004-MelQbG10, WT1 peptide, oregovomab, ofatumumab, zalutumumab, cintredekin besudotox, WX-G250, Albuferon, aflibercept, denosumab, vaccine, CTP-37, efungumab, or 131I-chTNT-1/B. Monoclonal antibodies useful as the protein therapeutic include, but are not limited to, muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or
(8) yield efficacy and tolerability results at least as good as those of the agents used alone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

As mentioned supra, the compounds of the present invention have surprisingly been found to effectively inhibit Mps-1 and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of general formula (I), or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula (I) described supra for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, wherein the diseases are haematological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumor enlargement and metastasis. Moreover, the growth of new blood and lymph vessels in a tumor provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological Assay: Proliferation Assay

Cultivated tumor cells (MCF7, hormone dependent human mammary carcinoma cells, ATCC HTB22; NCI-H460, human non-small cell lung carcinoma cells, ATCC HTB-177; DU 145, hormone-independent human prostate carcinoma cells, ATCC HTB-81; HeLa-MaTu, human cervical carcinoma cells, EPO-GmbH, Berlin; HeLa-MaTu-ADR, multidrug-resistant human cervical carcinoma cells, EPO-GmbH, Berlin; HeLa human cervical tumor cells, ATCC CCL-2; B16F10 mouse melanoma cells, ATCC CRL-6475) were plated at a density of 5000 cells/well (MCF7, DU145, HeLa-MaTu-ADR), 3000 cells/well (NCI-H460, HeLa-MaTu, HeLa), or 1000 cells/well (B16F10) in a 96-well multititer plate in 200 µl of their respective growth medium supplemented 10% fetal calf serum. After 24 hours, the cells of one plate (zero-point plate) were stained with crystal violet (see below), while the medium of the other plates was replaced by fresh culture medium (200 µl), to which the test substances were added in various concentrations (0 µM, as well as in the range of 0.01-30 µM; the final concentration of the solvent dimethyl sulfoxide was 0.5%). The cells were incubated for 4 days in the presence of test substances. Cell proliferation was determined by staining the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were stained by adding 100 µl/measuring point of a 0.1% crystal violet solution (pH 3.0). After three washing cycles of the stained cells with water, the plates were dried at room temperature. The dye was dissolved by adding 100 µl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 µm) cells (=100%). The IC50 values were determined by means of a 4 parameter fit using the company's own software.

The compounds of the present invention are characterized by an $IC_{50}$ determined in a HeLa-MaTu-ADR cell proliferation assay (as described above) that is lower than 10 µM. The $IC_{50}$ of preferred compounds is even lower than 2.0 µM. The $IC_{50}$ of more preferred compounds is even lower than 500 nM. The $IC_{50}$ of even more preferred compounds is even lower than 250 nM. The $IC_{50}$ of most preferred compounds is even lower than 200 nM.

The compounds of the present invention are characterized by the following $IC_{50}$ values, determined in a HeLa cell proliferation assay (as described above):

| Example Number | Inhibition of cell proliferation, cell Line: HeLa $IC_{50}$ |
| --- | --- |
| 01.01 | <400 nM |
| 01.02 | <600 nM |
| 01.03 | <200 nM |
| 01.04 | <400 nM |
| 01.05 | <100 nM |
| 01.06 | <100 nM |
| 01.07 | <100 nM |
| 01.08 | <100 nM |
| 01.09 | <400 nM |
| 01.10 | <200 nM |
| 01.11 | <600 nM |
| 01.12 | <200 nM |
| 01.13 | <400 nM |
| 01.14 | <100 nM |
| 01.15 | <100 nM |
| 01.16 | <100 nM |
| 01.17 | <600 nM |
| 01.18 | <100 nM |

-continued

| Example Number | Inhibition of cell proliferation, cell Line: HeLa IC$_{50}$ |
|---|---|
| 01.19 | <200 nM |
| 01.20 | <200 nM |
| 01.21 | <200 nM |
| 01.22 | <200 nM |
| 01.23 | <400 nM |
| 01.24 | <100 nM |
| 01.25 | <200 nM |

Mps-1 Kinase Assay

The human kinase Mps-1 phosphorylates a biotinylated substrate peptide. Detection of the phosphorylated product is achieved by time-resolved fluorescence resonance energy transfer (TR-FRET) from Europium-labelled anti-phospho-Serine/Threonine antibody as donor to streptavidin labelled with cross-linked allophycocyanin (SA-XLent) as acceptor. Compounds are tested for their inhibition of the kinase activity.

N-terminally GST-tagged human full length recombinant Mps-1 kinase (purchased from Invitrogen, Karslruhe, Germany, cat. no PV4071) was used. As substrate for the kinase reaction a biotinylated peptide of the amino-acid sequence PWDPDDADITEILG (SEQ ID NO: 1) (C-terminus in amide form, purchased from Biosynthan GmbH, Berlin) was used.

For the assay 50 nl of a 100-fold concentrated solution of the test compound in DMSO was pipetted into a black low volume 384 well microtiter plate (Greiner Bio-One, Frickenhausen, Germany), 2 µl of a solution of Mps-1 in assay buffer [0.1 mM sodium-ortho-vanadate, 10 mM MgCl$_2$, 2 mM DTT, 25 mM Hepes pH 7.7, 0.05% BSA, 0.001% Pluronic F-127] were added and the mixture was incubated for 15 min at 22° C. to allow pre-binding of the test compounds to Mps-1 before the start of the kinase reaction. Then the kinase reaction was started by the addition of 3 µl of a solution of 16.7 adenosine-tri-phosphate (ATP, 16.7 µM=>final conc. in the 5 µl assay volume is 10 µM) and peptide substrate (1.67 µM=>final conc. in the 5 µl assay volume is 1 µM) in assay buffer and the resulting mixture was incubated for a reaction time of 60 min at 22° C. The concentration of Mps-1 in the assay was adjusted to the activity of the enzyme lot and was chosen appropriate to have the assay in the linear range, typical enzyme concentrations were in the range of about 1 nM (final conc. in the 5 µl assay volume). The reaction was stopped by the addition of 3 µl of a solution of HTRF detection reagents (100 mM Hepes pH 7.4, 0.1% BSA, 40 mM EDTA, 140 nM Streptavidin-XLent [#61GSTXLB, Fa. Cis Biointernational, Marcoule, France], 1.5 nM anti-phospho(Ser/Thr)-Europium-antibody [#AD0180, PerkinElmer LAS, Rodgau-Jügesheim, Germany].

The resulting mixture was incubated 1 h at 22° C. to allow the binding of the phosphorylated peptide to the anti-phospho(Ser/Thr)-Europium-antibody. Subsequently the amount of phosphorylated substrate was evaluated by measurement of the resonance energy transfer from the Europium-labelled anti-phospho(Ser/Thr) antibody to the Streptavidin-XLent. Therefore, the fluorescence emissions at 620 nm and 665 nm after excitation at 350 nm was measured in a Viewlux TR-FRET reader (PerkinElmer LAS, Rodgau-Jügesheim, Germany). The "blank-corrected normalized ratio" (a Viewlux specific readout, similar to the traditional ratio of the emissions at 665 nm and at 622 nm, in which blank and Eu-donor crosstalk are subtracted from the 665 nm signal before the ratio is calculated) was taken as the measure for the amount of phosphorylated substrate. The data were normalised (enzyme reaction without inhibitor=0% inhibition, all other assay components but no enzyme=100% inhibition). Test compounds were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and IC$_{50}$ values were calculated by a 4 parameter fit using an inhouse software.

The compounds of the present invention are characterized by the following IC$_{50}$ values, determined in Mps-1 kinase assays (as described above):

| Example Number | Mps-1 Inhibition, IC$_{50}$ in M (Assay with 10 µM ATP) | Mps-1 Inhibition, IC$_{50}$ in M (Assay with 2 mM ATP) |
|---|---|---|
| 01.01 | <1 nM | 1.9 nM |
| 01.02 | <1 nM | <1 nM |
| 01.03 | <1 nM | <1 nM |
| 01.04 | <1 nM | 2.0 nM |
| 01.05 | <1 nM | 1.2 nM |
| 01.06 | <1 nM | 1.5 nM |
| 01.07 | <1 nM | <1 nM |
| 01.08 | <1 nM | <1 nM |
| 01.09 | <1 nM | 1.0 nM |
| 01.10 | <1 nM | 1.1 nM |
| 01.11 | <1 nM | 9.0 nM |
| 01.12 | <1 nM | <1 nM |
| 01.13 | <1 nM | <1 nM |
| 01.14 | <1 nM | <1 nM |
| 01.15 | <1 nM | <1 nM |
| 01.16 | <1 nM | 1.3 nM |
| 01.17 | <1 nM | 4.8 nM |
| 01.18 | <1 nM | <1 nM |
| 01.19 | <1 nM | <1 nM |
| 01.20 | <1 nM | 1.5 nM |
| 01.21 | <1 nM | <1 nM |
| 01.22 | <1 nM | <1 nM |
| 01.23 | <1 nM | <1 nM |
| 01.24 | <1 nM | <1 nM |
| 01.25 | <1 nM | <1 nM |

Spindle Assembly Checkpoint Assay

The spindle assembly checkpoint assures the proper segregation of chromosomes during mitosis. Upon entry into mitosis, chromosomes begin to condensate which is accompanied by the phosphorylation of histone H3 on serine 10. Dephosphorylation of histone H3 on serine 10 begins in anaphase and ends at early telophase. Accordingly, phosphorylation of histone H3 on serine 10 can be utilized as a marker of cells in mitosis. Nocodazole is a microtubule destabilizing substance. Thus, nocodazole interferes with microtubule dynamics and mobilises the spindle assembly checkpoint. The cells arrest in mitosis at G2/M transition and exhibit phosphorylated histone H3 on serine 10. An inhibition of the spindle assembly checkpoint by Mps-1 inhibitors overrides the mitotic blockage in the presence of nocodazole, and the cells complete mitosis prematurely. This alteration is detected by the decrease of cells with phosphorylation of histone H3 on serine 10. This decline is used as a marker to determine the capability of compounds of the present invention to induce a mitotic breakthrough.

Cultivated cells of the human cervical tumor cell line HeLa (ATCC CCL-2) were plated at a density of 2500 cells/well in a 384-well microtiter plate in 20 μl Dulbeco's Medium (w/o phenol red, w/o sodium pyruvate, w 1000 mg/ml glucose, w pyridoxine) supplemented with 1% (v/v) glutamine, 1% (v/v) penicillin, 1% (v/v) streptomycin and 10% (v/v) fetal calf serum. After incubation overnight at 37° C., 10 μl/well nocodazole at a final concentration of 0.1 μg/ml were added to cells. After 24 h incubation, cells were arrested at G2/M phase of the cell cycle progression. Test compounds solubilised in dimethyl sulfoxide (DMSO) were added at various concentrations (0 μM, as well as in the range of 0.005 μM-10 μM; the final concentration of the solvent DMSO was 0.5% (v/v)). Cells were incubated for 4 h at 37° C. in the presence of test compounds. Thereafter, cells were fixed in 4% (v/v) paraformaldehyde in phosphate buffered saline (PBS) at 4° C. overnight then permeabilised in 0.1% (v/v) Triton X™ 100 in PBS at room temperature for 20 min and blocked in 0.5% (v/v) bovine serum albumin (BSA) in PBS at room temperature for 15 min. After washing with PBS, 20 μl/well antibody solution (anti-phospho-histone H3 clone 3H10, FITC; Upstate, Cat#16-222; 1:200 dilution) was added to cells, which were incubated for 2 h at room temperature. Afterwards, cells were washed with PBS and 20 μl/well HOECHST 33342 dye solution (5 μg/ml) was added to cells and cells were incubated 12 min at room temperature in the dark. Cells were washed twice with PBS then covered with PBS and stored at 4° C. until analysis. Images were acquired with a Perkin Elmer OPERA™ High-Content Analysis reader. Images were analyzed with image analysis software MetaXpress™ from Molecular devices utilizing the Cell Cycle application module. In this assay both labels HOECHST 33342 and phosphorylated Histone H3 on serine 10 were measured. HOECHST 33342 labels DNA and is used to count cell number. The staining of phosphorylated Histone H3 on serine 10 determines the number of mitotic cells. Inhibition of Mps-1 decreases the number of mitotic cells in the presence of nocodazole indicating an inappropriate mitotic progression. The raw assay data were further analysed by four parameter logistic regression analysis to determine the $IC_{50}$ value for each tested compound.

It will be apparent to persons skilled in the art that assays for other Mps kinases may be performed in analogy using the appropriate reagents.

Thus the compounds of the present invention effectively inhibit one or more Mps-1 kinases and are therefore suitable for the treatment or prophylaxis of diseases of uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, more particularly in which the diseases of uncontrolled cell growth, proliferation and/or survival, inappropriate cellular immune responses, or inappropriate cellular inflammatory responses are haemotological tumours, solid tumours and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

Determination of Metabolic Stability In Vitro (Including Calculation of Hepatic In Vivo Blood Clearance (CL) and of Maximal Oral Bioavailability ($F_{max}$))

The metabolic stability of test compounds in vitro was determined by incubating them at 1 μM with a suspension liver microsomes in 100 mM phosphate buffer, pH7.4 ($NaH_2PO_4 \times H_2O + Na_2HPO_4 \times 2H_2O$) at a protein concentration of 0.5 mg/mL and at 37° C. The reaction was activated by adding a co-factor mix containing 1.2 mg NADP, 3 IU glucose-6-phosphate dehydrogenase, 14.6 mg glucose-6-phosphate and 4.9 mg $MgCl_2$ in phosphate buffer, pH 7.4. Organic solvent in the incubations was limited to <0.2% dimethylsulfoxide (DMSO) and <1% methanol. During incubation, the microsomal suspensions were continuously shaken and aliquots were taken at 2, 8, 16, 30, 45 and 60 min, to which equal volumes of cold methanol were immediately added. Samples were frozen at −20° C. over night, subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, specific liver weight and microsomal protein content the hepatic in vivo blood clearance (CL) and the maximal oral bioavailability ($F_{max}$) were calculated for the different species. The following parameter values were used: Liver blood flow—1.3 L/h/kg (human), 2.1 L/h/kg (dog), 4.2 L/h/kg (rat); specific liver weight—21 g/kg (human), 39 g/kg (dog), 32 g/kg (rat); microsomal protein content—40 mg/g.

With the described assay only phase-I metabolism of microsomes is reflected, e.g. typically oxidoreductive reactions by cytochrome P450 enzymes and flavin mono-oxygenases (FMO) and hydrolytic reactions by esterases (esters and amides).

The compounds of the present invention are characterized by the values of maximum oral bioavailability ($F_{max}$) in rat, dog and humans (determined by means of liver microsomes as described above) shown in the table below:

| Example Number | Rat liver microsomes; Fmax [%] | Human liver microsomes; Fmax [%] | Dog liver microsomes; Fmax [%] |
|---|---|---|---|
| 01.01 | 92 | 92 | 64 |
| 01.02 | 86 | 68 | 73 |
| 01.03 | 93 | >95 | 55 |
| 01.04 | 87 | >95 | 94 |
| 01.05 | >95 | >95 | 89 |
| 01.06 | 94 | >95 | 81 |
| 01.07 | 83 | >95 | 86 |
| 01.08 | 74 | 62 | 75 |
| 01.09 | 58 | 49 | 48 |
| 01.10 | >95 | >95 | >95 |
| 01.11 | 92 | 76 | 75 |

Surprisingly it was found, that the compounds of the present invention show superior properties over compounds of the state of the art.

The compounds of the present invention are characterized by the following attributes:

The $IC_{50}$ determined in an Mps-1 kinase assay with a concentration of 10 μM ATP (as described above) is lower than or equal to 1 nM.

The $IC_{50}$ determined in an Mps-1 kinase assay with a concentration of 2 mM ATP (as described above) is lower than 10 nM. The $IC_{50}$ of preferred compounds is even lower than 5 nM. The $IC_{50}$ of more preferred compounds is even lower than 3 nM. The $IC_{50}$ of most preferred compounds is even lower than 2 nM.

The maximum oral bioavailability ($F_{max}$) in rat (determined by means of rat liver microsomes as described above) is higher than 50%. The $F_{max}$ of preferred compounds is even higher than 70%. The $F_{max}$ of more preferred compounds is even higher than 80%.

The maximum oral bioavailability ($F_{max}$) in dog (determined by means of dog liver microsomes as described above) is higher than 45%. The $F_{max}$ of preferred compounds is even higher than 52%. The $F_{max}$ of more preferred compounds is even higher than 70%.

The maximum oral bioavailability ($F_{max}$) in human (determined by means of human liver microsomes as described above) is higher than 45%. The $F_{max}$ of preferred compounds is even higher than 60%. The $F_{max}$ of more preferred compounds is even higher than 85%.

The $IC_{50}$ determined in a HeLa cell proliferation assay (as described above) is lower than 600 nM. The $IC_{50}$ of preferred compounds is even lower than 400 nM. The $IC_{50}$ of more preferred compounds is even lower than 200 nM. The $IC_{50}$ of most preferred compounds is even lower than 100 nM.

The following table demonstrates the superiority of the compounds of the present invention by way of comparison with compounds from prior art as well as with compounds which are structurally similar to compounds of the present invention but which do not fall under formula (I) as defined herein.

| Formula | Specification of Example | Rat liver microsomes; Fmax [%] | Dog liver microsomes; Fmax [%] |
|---|---|---|---|
| *[structure]* | comparitive example | | 15 |
| *[structure]* | comparitive example disclosed in WO 2011/063908 A1 | | 40 |
| *[structure]* | comparitive example disclosed in WO2011/063908 A1 | | 40 |
| *[structure]* | comparitive example disclosed in WO2011/063908 A1 | | 19 |

| Formula | Specification of Example | Rat liver microsomes; Fmax [%] | Dog liver microsomes; Fmax [%] |
|---|---|---|---|
| | comparitive example | 27 | |
| | comparitive example | 26 | |
| | comparitive example contained in PCT/EP2011/059806 | 48 | |
| | comparitive example | 12 | |

-continued

| Formula | Specification of Example | Rat liver microsomes; Fmax [%] | Dog liver microsomes; Fmax [%] |
|---|---|---|---|
| (structure) | comparitive example | | 40 |
| (structure) | comparitive example contained in EP patent application No. 11167139.2 | | 17 |
| (structure) | comparitive example contained in EP patent application No. 11167872.8 | | 10 |
| (structure) | comparitive example contained in EP patent application No. 11167872.8 | | 25 |

-continued
| Formula | Specification of Example | Rat liver microsomes; Fmax [%] | Dog liver microsomes; Fmax [%] |
|---|---|---|---|
| 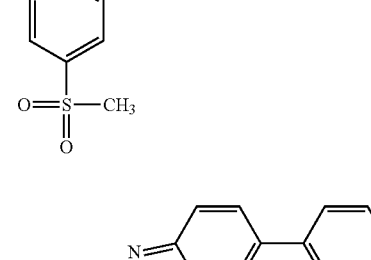 | Inventive Example 01.01 | 92 | 64 |
| 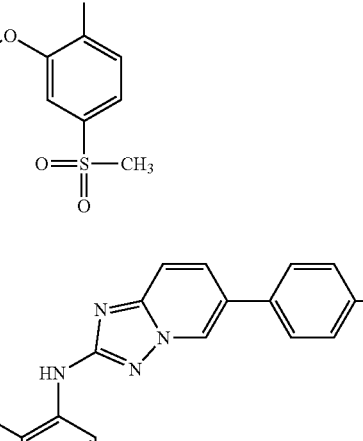 | Inventive Example 01.03 | 93 | 55 |
| 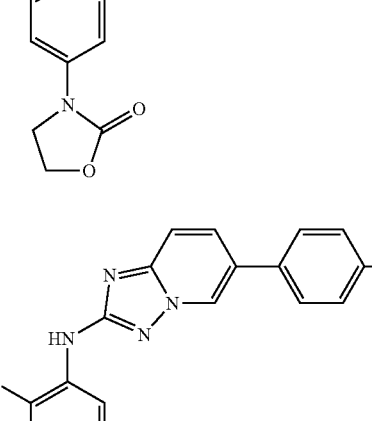 | Inventive Example 01.09 | 58 | 48 |
|  | Inventive Example 01.07 | 83 | 86 |

-continued

| Formula | Specification of Example | Rat liver microsomes; Fmax [%] | Dog liver microsomes; Fmax [%] |
|---|---|---|---|
| (structure) | Inventive Example 01.04 | 87 | 94 |

| Structure | Specification of Example | Mps-1 Inhibition, IC$_{50}$ (Assay with 10 μM ATP) | Inhibition of cell proli-feration, cell Line: HeLa; IC$_{50}$ |
|---|---|---|---|
| (structure) | comparitive example | | 1500 nM |
| (structure) | comparitive example | 11 nM | 1400 nM |
| (structure) | comparitive example disclosed in WO 2011/063908 A1 | 13 nM | |

-continued

| Structure | Specification of Example | Mps-1 Inhibition, IC$_{50}$ (Assay with 10 μM ATP) | Inhibition of cell proli-feration, cell Line: HeLa; IC$_{50}$ |
|---|---|---|---|
| 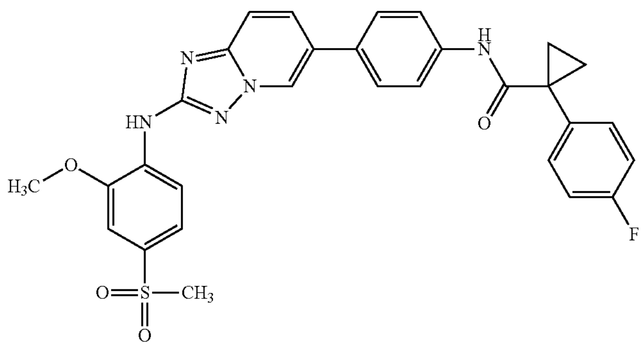 [SMILES: COc1cc(S(C)(=O)=O)ccc1Nc1nc2ccc(-c3ccc(NC(=O)C4(c5ccc(F)cc5)CC4)cc3)cn2n1] | comparitive example | 15 nM | |
| 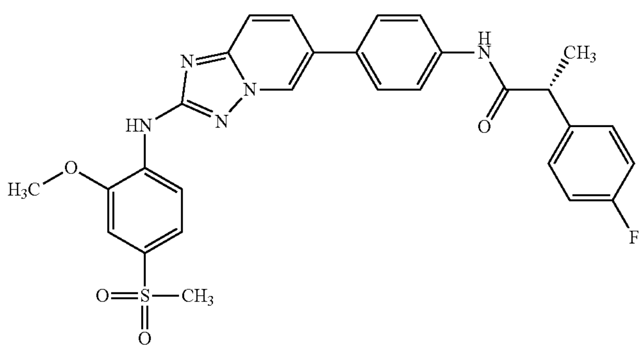 [SMILES: COc1cc(S(C)(=O)=O)ccc1Nc1nc2ccc(-c3ccc(NC(=O)[C@H](C)c4ccc(F)cc4)cc3)cn2n1] | Inventive Example 01.01 | <1 nM | <400 nM |
| 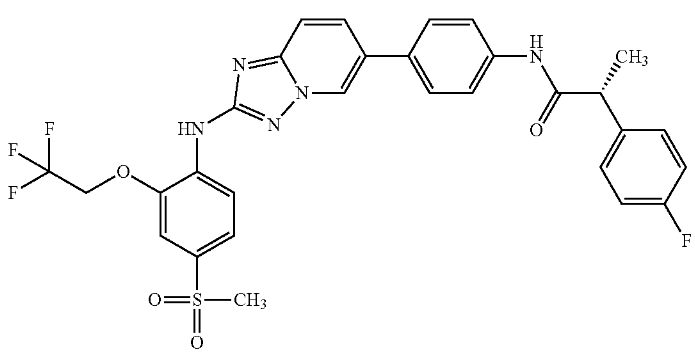 [SMILES: C[C@@H](C(=O)Nc1ccc(-c2ccc3nc(Nc4ccc(S(C)(=O)=O)cc4OCC(F)(F)F)nn3c2)cc1)c1ccc(F)cc1] | Inventive Example 01.03 | <1 nM | <200 nM |
| 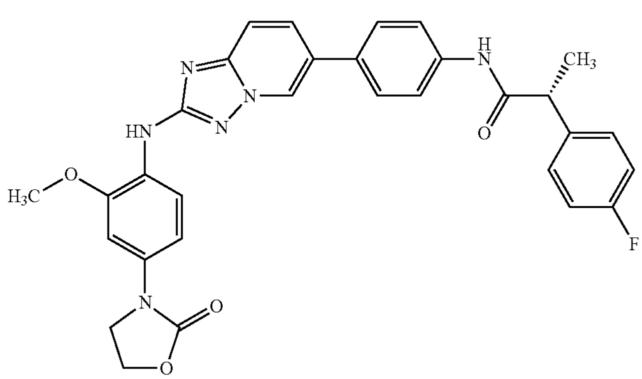 [SMILES: COc1cc(N2CCOC2=O)ccc1Nc1nc2ccc(-c3ccc(NC(=O)[C@H](C)c4ccc(F)cc4)cc3)cn2n1] | Inventive Example 01.09 | <1 nM | <400 nM |

-continued

| Structure | Specification of Example | Mps-1 Inhibition, IC$_{50}$ (Assay with 10 μM ATP) | Inhibition of cell proli-feration, cell Line: HeLa; IC$_{50}$ |
|---|---|---|---|
| 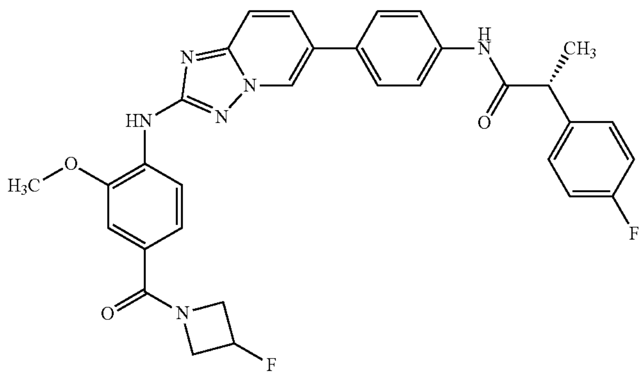 [SMILES: COc1cc(C(=O)N2CC(F)C2)ccc1Nc1nc2ccc(-c3ccc(NC(=O)[C@H](C)c4ccc(F)cc4)cc3)cn2n1] | Inventive Example 01.07 | <1 nM | <100 nM |
| 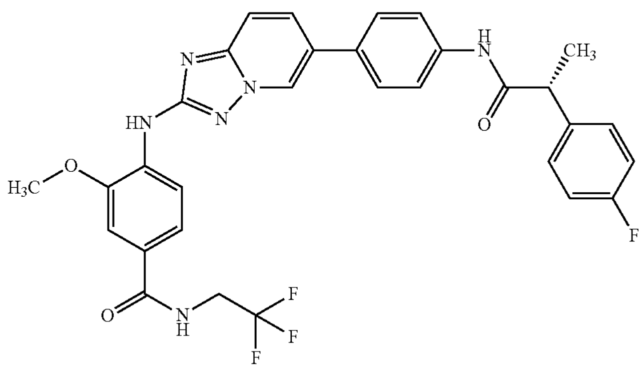 [SMILES: COc1cc(C(=O)NCC(F)(F)F)ccc1Nc1nc2ccc(-c3ccc(NC(=O)[C@H](C)c4ccc(F)cc4)cc3)cn2n1] | Inventive Example 01.04 | <1 nM | <400 nM |

| Prior Art Document | Example No. | Mps-1 Inhibition, IC$_{50}$ (Assay with 10 μM ATP) | Inhibition of cell proli-feration, cell Line: HeLa; IC$_{50}$ |
|---|---|---|---|
| WO 2011/064328 A1 | 11.001 | 20 nM | |
| WO 2011/064328 A1 | 11.002 | 21 nM | |
| WO 2011/064328 A1 | 11.005 | 27 nM | |
| WO 2011/064328 A1 | 11.006 | 28 nM | |
| WO 2011/064328 A1 | 11.007 | 66 nM | |
| WO 2011/064328 A1 | 11.018 | 58 nM | |
| WO 2011/064328 A1 | 11.028 | | 1100 nM |
| WO 2011/064328 A1 | 11.029 | | 630 nM |
| WO 2011/064328 A1 | 11.030 | 16 nM | |
| WO 2011/064328 A1 | 11.031 | 18 nM | |
| WO 2011/064328 A1 | 11.032 | 20 nM | |
| WO 2011/064328 A1 | 11.033 | 23 nM | |
| WO 2011/064328 A1 | 11.037 | | 1100 nM |
| WO 2011/064328 A1 | 11.042 | 53 nM | |
| WO 2011/064328 A1 | 11.043 | 60 nM | |
| WO 2011/064328 A1 | 11.076 | | 730 nM |
| WO 2011/064328 A1 | 11.077 | 16 nM | |
| WO 2011/064328 A1 | 11.078 | 23 nM | |
| WO 2011/064328 A1 | 11.079 | 24 nM | |
| WO 2011/064328 A1 | 11.080 | 25 nM | |
| WO 2011/064328 A1 | 11.081 | 28 nM | |
| WO 2011/064328 A1 | 11.083 | 32 nM | |
| WO 2011/064328 A1 | 11.084 | 40 nM | |
| WO 2011/064328 A1 | 11.085 | | 1800 nM |
| WO 2011/064328 A1 | 11.086 | | 2200 nM |
| WO 2011/064328 A1 | 11.087 | | 870 nM |
| WO 2011/064328 A1 | 11.088 | 15 nM | |
| WO 2011/064328 A1 | 11.089 | 25 nM | |
| WO 2011/064328 A1 | 11.091 | | 1300 nM |
| WO 2011/064328 A1 | 11.092 | | 820 nM |
| WO 2011/064328 A1 | 11.093 | | 2400 nM |
| WO 2011/064328 A1 | 11.094 | | 1400 nM |
| WO 2011/064328 A1 | 11.095 | | 2000 nM |
| WO 2011/064328 A1 | 11.096 | | 1900 nM |

| Prior Art Document | Example No. | Inhibition of cell proli-feration, cell Line: HeLa; IC$_{50}$ | Rat liver microsomes; Fmax [%] |
|---|---|---|---|
| WO 2011/063908 A1 | 3.3 | 1500 nM | |
| WO 2011/063908 A1 | 3.4 | 1300 nM | |
| WO 2011/063908 A1 | 3.5 | | 27 |
| WO 2011/063908 A1 | 3.6 | | 40 |
| WO 2011/063908 A1 | 3.9 | | 21 |
| WO 2011/063908 A1 | 3.10 | 930 nM | |
| WO 2011/063908 A1 | 3.11 | | 25 |
| WO 2011/063908 A1 | 4.1 | | 40 |
| WO 2011/063908 A1 | 7.1 | | 29 |

The invention claimed is:

1. A compound of formula (I):

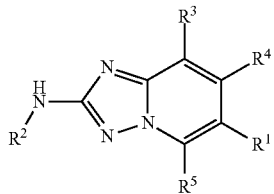

wherein:

$R^1$ is

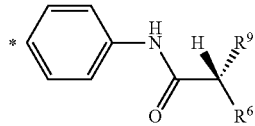

wherein * indicates the point of attachment of said group to the rest of the molecule;

$R^2$ is

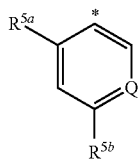

wherein * indicates the point of attachment of said group to the rest of the molecule;

$R^3$ is a hydrogen atom;

$R^4$ is a hydrogen atom;

$R^5$ is a hydrogen atom or a $C_1$-$C_3$-alkyl- group;

$R^{5a}$ is a group selected from: $C_1$-$C_4$-alkoxy-, halo-$C_1$-$C_4$-alkoxy-, and $C_1$-$C_4$-alkyl;

$R^{5b}$ is a group selected from:
—C(=O)N(H)$R^8$, —C(=O)N$R^8R^7$, —N($R^7$)C(=O)O$R^8$, and $R^7$—S(=O)$_2$—;

$R^6$ is a

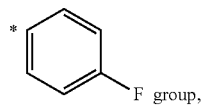

wherein * indicates the point of attachment of said group to the rest of the molecule,
and wherein said group is optionally substituted, one or more times, identically or differently, with a halogen atom or a methyl- group;

$R^7$ is a $C_1$-$C_3$-alkyl- or a cyclopropyl- group;

$R^8$ is a hydrogen atom or a $C_1$-$C_6$-alkyl- or $C_3$-$C_6$-cycloalkyl- group,
wherein said $C_1$-$C_6$-alkyl- or $C_3$-$C_6$-cycloalkyl- group is optionally substituted, one or more times, with a halogen atom;

or $R^7$ and $R^8$ together with the molecular fragment to which they are attached form a 4- to 6-membered heterocyclic ring, which is optionally substituted, one or more times, identically or differently, with a halogen atom, a $C_1$-$C_3$-alkyl-, halo-$C_1$-$C_3$-alkyl- or $C_1$-$C_3$ alkoxy- group, or a hydroxyl group;

$R^9$ is a group selected from: $C_1$-$C_3$-alkyl-, hydroxy-$C_1$-$C_3$-alkyl, —N(H)$R^8$, —N($R^7$)$R^8$, N(H)($R^8$)—$C_1$-$C_3$-alkyl-, and N($R^7$)($R^8$)—$C_1$-$C_3$-alkyl-; and Q is CH or N, or a tautomer, an N-oxide, a hydrate, a solvate, or a salt thereof, or a mixture of any of the foregoing.

2. The compound according to claim 1, wherein:

$R^5$ is a hydrogen atom, or a tautomer, an N-oxide, a hydrate, a solvate, or a salt thereof, or a mixture of any of the foregoing.

3. The compound according to claim 1, wherein:

Q is CH, or a tautomer, an N-oxide, a hydrate, a solvate, or a salt thereof, or a mixture of any of the foregoing.

4. The compound according to claim 1, wherein:

$R^{5a}$ is a group selected from: $C_1$-$C_2$-alkoxy- and halo-$C_1$-$C_2$-alkoxy-, or a tautomer, an N-oxide, a hydrate, a solvate, or a salt thereof, or a mixture of any of the foregoing.

5. The compound according to claim 1, wherein:
R⁶ is a

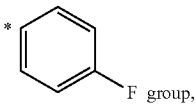

wherein * indicates the point of attachment of said group to the rest of the molecule,
or a tautomer, an N-oxide, a hydrate, a solvate, or a salt thereof, or a mixture of any of the foregoing.

6. The compound according to claim 1, wherein:
R⁹ is a group selected from: methyl-, hydroxy-$C_1$-$C_2$-alkyl-, —$NH_2$, —$N(R^{10})R^{10}$, and —$C_1$-$C_2$-alkyl-$N(R^{10})R^{10}$; and
R¹⁰ is a hydrogen atom or a methyl- group,
or a tautomer, an N-oxide, a hydrate, a solvate, or a salt thereof, or a mixture of any of the foregoing.

7. The compound according to claim 1, wherein:
R⁹ is a group selected from: methyl-, hydroxy-methyl-, and —$NH_2$,
or a tautomer, an N-oxide, a hydrate, a solvate, or a salt thereof, or a mixture of any of the foregoing.

8. A compound according to claim 1, wherein:
$R^{5b}$ is a group selected from:
—C(=O)N(H)R⁸ and —C(=O)NR⁸R⁷;
R⁷ is a $C_1$-$C_3$-alkyl- group; and
R⁸ is a hydrogen atom or a $C_1$-$C_3$-alkyl- group,
wherein said $C_1$-$C_3$-alkyl- group is optionally substituted, one or more times, with a halogen atom;
or
R⁷ and R⁸ together with the molecular fragment to which they are attached form a 4- to 6-membered heterocyclic ring, which is optionally substituted, one or more times, identically or differently, with a halogen atom,
or a tautomer, an N-oxide, a hydrate, a solvate, or a salt thereof, or a mixture of any of the foregoing.

9. The compound according to claim 1, wherein:
$R^{5b}$ is a —N(R⁷)C(=O)OR⁸ group; and
R⁷ and R⁸ together with the molecular fragment to which they are attached form a 4- to 6-membered heterocyclic ring,
or a tautomer, an N-oxide, a hydrate, a solvate, or a salt thereof, or a mixture of any of the foregoing.

10. The compound according to claim 1, wherein:
$R^{5b}$ is a R⁷—S(=O)₂— group; and
R⁷ is a $C_1$-$C_3$-alkyl- group,
or a tautomer, an N-oxide, a hydrate, a solvate, or a salt thereof, or a mixture of any of the foregoing.

11. The compound according to claim 1, which is selected from the group consisting of:
(2R)-2-(4-fluorophenyl)-N-[4-(2-{[2-methoxy-4-(methylsulfonyl)phenyl]amino}[1,2,4]triazolo[1,5-a]pyridin-6-yl)phenyl]propanamide;
(2R)—N-[4-(2-{[2-ethoxy-4-(methylsulfonyl)phenyl]amino}[1,2,4]triazolo[1,5-a]pyridin-6-yl)phenyl]-2-(4-fluorophenyl)propanamide;
(2R)-2-(4-fluorophenyl)-N-[4-(2-{[4-(methylsulfonyl)-2-(2,2,2-trifluoroethoxy)-phenyl]amino}[1,2,4]triazolo[1,5-a]pyridin-6-yl)phenyl]propanamide;
4-{[6-(4-{[(2R)-2-(4-fluorophenyl)propanoyl]amino}phenyl)[1,2,4]triazolo [1,5-a]pyridin-2-yl]amino}-3-methoxy-N-(2,2,2-trifluoroethyl)benzamide;
4-{[6-(4-{[(2R)-2-(4-fluorophenyl)propanoyl]amino}phenyl)[1,2,4]triazolo [1,5-a]pyridin-2-yl]amino}-3-methoxybenzamide;
4-{[6-(4-{[(2R)-2-(4-fluorophenyl)propanoyl]amino}phenyl)[1,2,4]triazolo [1,5-a]pyridin-2-yl]amino}-3-(2,2,2-trifluoroethoxy)benzamide;
(2R)—N-{4-[2-({4-[(3-fluoroazetidin-1-yl)carbonyl]-2-methoxyphenyl}amino)[1,2,4]triazolo [1,5-a]pyridin-6-yl]phenyl}-2-(4-fluorophenyl)propanamide;
(2R)—N-[4-(2-{[4-(azetidin-1-ylcarbonyl)-2-methoxyphenyl]amino}[1,2,4]triazolo[1,5-a]pyridin-6-yl)phenyl]-2-(4-fluorophenyl)propanamide;
(2R)-2-(4-fluorophenyl)-N-[4-(2-{[2-methoxy-4-(2-oxo-1,3-oxazolidin-3-yl)phenyl]-amino}[1,2,4]triazolo[1,5-a]pyridin-6-yl)phenyl]propanamide;
(−)-2-(4-fluorophenyl)-3-hydroxy-N-[4-(2-{[4-(methylsulfonyl)-2-(2,2,2-tri-fluoroethoxy)phenyl]amino}[1,2,4]triazolo[1,5-a]pyridin-6-yl)phenyl]propanamide;
(2R)-2-amino-2-(4-fluorophenyl)-N-[4-(2-{[2-methoxy-4-(methylsulfonyl)-phenyl]amino}[1,2,4]triazolo[1,5-a]pyridin-6-yl)phenyl]ethanamide;
4-{[6-(4-{[(2R)-2-(4-fluorophenyl)propanoyl]amino}phenyl)[1,2,4]triazolo [1,5-a]pyridin-2-yl]amino}-3-methoxy-N,N-dimethylbenzamide;
(2R)-2-(4-fluorophenyl)-N-[4-(2-{[2-methoxy-4-(pyrrolidin-1-ylcarbonyl)phenyl]amino}[1,2,4]triazolo[1,5-a]pyridin-6-yl)phenyl]propanamide;
(2R)—N-{4-[2-({4-[(3-fluoroazetidin-1-yl)carbonyl]-2-(2,2,2-trifluoroethoxy)phenyl}amino)[1,2,4]triazolo[1,5-a]pyridin-6-yl]phenyl}-2-(4-fluorophenyl)propanamide;
(2R)-2-(4-fluorophenyl)-N-{4-[2-({4-[(3-hydroxyazetidin-1-yl)carbonyl]-2-(2,2,2-trifluoroethoxy)phenyl}amino)[1,2,4]triazolo[1,5-a]pyridin-6-yl]phenyl}propanamide;
(2R)-2-(4-fluorophenyl)-N-[4-(2-{[4-(pyrrolidin-1-ylcarbonyl)-2-(2,2,2-trifluoroethoxy)phenyl]amino}[1,2,4]triazolo[1,5-a]pyridin-6-yl)phenyl]propanamide;
(2S)-2-(4-fluorophenyl)-3-hydroxy-N-[4-(2-{[2-methoxy-4-(methylsulfonyl)phenyl]amino}[1,2,4]triazolo[1,5-a]pyridin-6-yl)phenyl]propanamide;
(2S)—N-{4-[2-({4-[(3-fluoroazetidin-1-yl)carbonyl]-2-(2,2,2-trifluoroethoxy)phenyl}amino)[1,2,4]triazolo[1,5-a]pyridin-6-yl]phenyl}-2-(4-fluorophenyl)-3-hydroxypropanamide;
(2R)-2-amino-2-(4-fluorophenyl)-N-[4-(2-{[4-(methylsulfonyl)-2-(2,2,2-trifluoroethoxy)phenyl]amino}[1,2,4]triazolo[1,5-a]pyridin-6-yl)phenyl]ethanamide;
(2R)-2-amino-2-(4-fluorophenyl)-N-[4-(2-{[2-methoxy-4-(2-oxo-1,3-oxazolidin-3-yl)phenyl]amino}[1,2,4]triazolo[1,5-a]pyridin-6-yl)phenyl]ethanamide;
(2R)-2-amino-N-{4-[2-({4-[(3-fluoroazetidin-1-yl)carbonyl]-2-methoxyphenyl}amino)[1,2,4]triazolo[1,5-a]pyridin-6-yl]phenyl}-2-(4-fluorophenyl)ethanamide;
(2R)-2-amino-N-[4-(2-{[4-(azetidin-1-ylcarbonyl)-2-methoxyphenyl]amino}[1,2,4]triazolo [1,5-a]pyridin-6-yl)phenyl]-2-(4-fluorophenyl)ethanamide;
(2R)-2-amino-2-(4-fluorophenyl)-N-[4-(2-{[2-methoxy-4-(pyrrolidin-1-ylcarbonyl)phenyl]amino}[1,2,4]triazolo[1,5-a]pyridin-6-yl)phenyl]ethanamide;
(2R)-2-amino-N-{4-[2-({4-[(3-fluoroazetidin-1-yl)carbonyl]-2-(2,2,2-trifluoroethoxy)phenyl}amino)[1,2,4]triazolo [1,5-a]pyridin-6-yl]phenyl}-2-(4-fluorophenyl)ethanamide; and (2R)-2-amino-2-(4-fluorophenyl)-N-[4-(2-{[4-(pyrrolidin-1-ylcarbonyl)-2-(2,2,2-trifluoroethoxy)phenyl]amino}[1,2,4]triazolo[1,5-a]pyridin-6-yl)phenyl]ethanamide, or a tautomer, an N-oxide, a hydrate, a solvate, or a salt thereof, or a mixture of any of the foregoing.

12. A method of preparing the compound of formula (I) according to claim 1, comprising reacting an intermediate compound of formula (5):

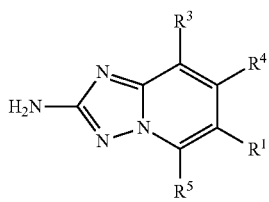
(5)

wherein R¹, R³, R⁴, and R⁵ are as defined in claim 1, with a compound of formula (5a):

R²—Y  (5a)

wherein R² is as defined in claim 1, and Y is a leaving group, to provide the compound of formula (I).

13. A method of preparing the compound of formula (I) according to claim 1, comprising reacting an intermediate compound of formula (5):

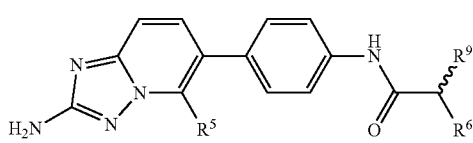
(5)

wherein R⁵, R⁶, and R⁹ are as defined in claim 1, with an aryl compound of formula (5a):

R²—Y  (5a)

wherein R² is as defined in claim 1, and Y is a leaving group, to provide a compound of formula (Ia):

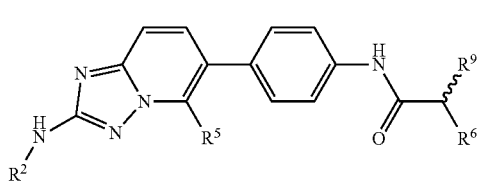
(Ia)

wherein R², R⁵, R⁶, and R⁹ are as defined in claim 1; and optionally separating the compound of formula (I) from a compound of formula (Ib):

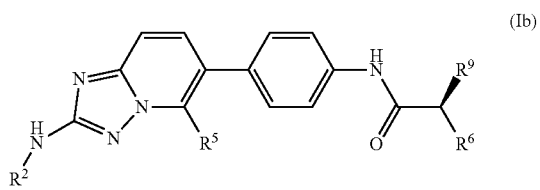
(Ib)

wherein R², R⁵, R⁶, and R⁹ are as defined in claim 1.

14. A method of preparing the compound of formula (I) according to claim 1, comprising reacting an intermediate compound of formula (7):

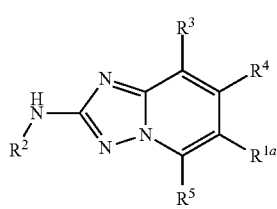
(7)

wherein R², R³, R⁴, and R⁵ are as defined in claim 1, and R¹ᵃ is a phenyl group to which an —NH₂ substituent is bound in para position, with a compound of formula (7a):

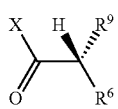
(7a)

wherein R⁹ and R⁶ are as defined in claim 1, and X is a suitable functional group, via which the R¹ᵇ of the R¹ᵇ—X compound (7a) can be coupled, via a coupling reaction, onto the —NH₂ substituent bound to the phenyl group R¹ᵃ of compound (7), to provide the compound of formula (I).

15. A method of preparing the compound of formula (I) according to claim 1, comprising reacting an intermediate compound of formula (7):

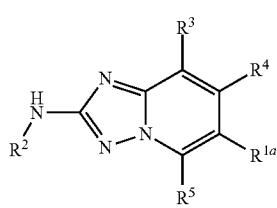
(7)

wherein R², R³, R⁴, and R⁵ are as defined in claim 1, and R¹ᵃ is a phenyl group to which an —NH₂ substituent is bound in the para position, with a compound of formula (7a):

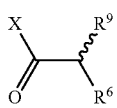

wherein R⁹ and R⁶ are as defined in claim 1, and X is a suitable functional group, via which the —C(O)C(H)R⁶R⁹ group of compound (7a) can be coupled, via a coupling reaction onto the —NH₂ substituent bound to the phenyl group R$^{1a}$ of compound (7), to provide a compound of formula (Ia):

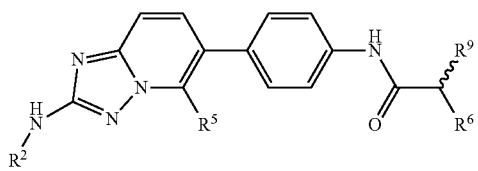

and
optionally separating the compound of formula (I) from a compound of formula (Ib):

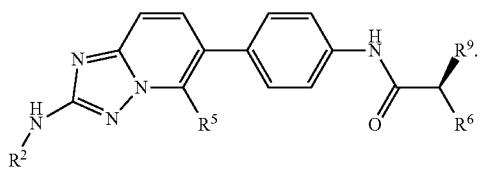

16. A pharmaceutical composition comprising the compound according to claim 1, or a tautomer, an N-oxide, a hydrate, a solvate, or a pharmaceutically acceptable salt thereof, or a mixture of any of the foregoing, and a pharmaceutically acceptable diluent or carrier.

17. A pharmaceutical combination comprising:
one or more compounds according to claim 1, or a tautomer, an N-oxide, a hydrate, a solvate, or a pharmaceutically acceptable salt thereof, or a mixture of any of the foregoing; and
one or more agents selected from: a taxane, Docetaxel, Paclitaxel, or Taxol; an epothilone, Ixabepilone, Patupilone, or Sagopilone; Mitoxantrone; Predinisolone; Dexamethasone; Estramustin; Vinblastin; Vincristin; Doxorubicin; Adriamycin; Idarubicin; Daunorubicin; Bleomycin; Etoposide; Cyclophosphamide; Ifosfamide; Procarbazine; Melphalan; 5-Fluorouracil; Capecitabine; Fludarabine; Cytarabine; Ara-C; 2-Chloro-2'-deoxyadenosine; Thioguanine; an anti-androgen, Flutamide, Cyproterone acetate, or Bicalutamide; Bortezomib; a platinum derivative, Cisplatin, or Carboplatin; Chlorambucil; Methotrexate; and Rituximab.

18. A method for the treatment of a disease of uncontrolled cell growth, proliferation or survival, cellular immune response, or cellular inflammatory response, which is responsive to inhibition of Mps-1 kinase activity comprising administering to a patient in need thereof a therapeutically effective amount of the compound according to claim 1 or a tautomer, an N-oxide, a hydrate, a solvate, or a pharmaceutically acceptable salt thereof, or a mixture of the foregoing.

19. The method of claim 18, wherein the disease of uncontrolled cell growth, proliferation or survival, cellular immune response, or cellular inflammatory response is a haemotological tumour, a solid tumour or metastases thereof.

20. The method of claim 19, wherein the haemotological tumour, solid tumour or metastases thereof is selected from leukemias and myelodysplastic syndrome, malignant lymphomas, head and neck tumours, brain tumours and brain metastases, tumours of the thorax, non-small cell and small cell lung tumours, gastrointestinal tumours, endocrine tumours, mammary and other gynaecological tumours, urological tumours, renal, bladder and prostate tumours, skin tumours, and sarcomas, or metastases thereof.

21. The method according to claim 18, wherein the disease of uncontrolled cell growth, proliferation or survival, cellular immune response, or cellular inflammatory response is cervical cancer.

22. A method for the inhibition of Mps-1 kinase activity comprising contacting a target cell with an effective amount of the compound according to claim 1 or a tautomer, an N-oxide, a hydrate, a solvate, or a pharmaceutically acceptable salt thereof, or a mixture of any of the foregoing.

23. The compound according to claim 1, wherein the compound is:
(2R)-2-(4-fluorophenyl)-N-[4-(2-{[2-methoxy-4-(methylsulfonyl)phenyl]amino}[1,2,4]triazolo[1,5-a]pyridin-6-yl)phenyl]propanamide,
or a tautomer, an N-oxide, a hydrate, a solvate, or a pharmaceutically acceptable salt thereof, or a mixture of any of the foregoing.

24. The compound according to claim 1, wherein the compound is:
(2R)-2-(4-fluorophenyl)-N-[4-(2-{[2-methoxy-4-(methylsulfonyl)phenyl]amino}[1,2,4]triazolo[1,5-a]pyridin-6-yl)phenyl]propanamide,
or a pharmaceutically acceptable salt thereof.

25. A pharmaceutical composition comprising (2R)-2-(4-fluorophenyl)-N-[4-(2-{[2-methoxy-4-(methylsulfonyl) phenyl]amino}-[1,2,4]triazolo [1,5-a]pyridin-6-yl)phenyl] propanamide, or a pharmaceutically acceptable salt thereof, and a pharmaceutically acceptable diluent or carrier.

26. The pharmaceutical composition of claim 25, further comprising one or more agents selected from a taxane, an epothilone, an anti-androgen or a platinum derivative.

27. The pharmaceutical composition of claim 25, further comprising one or more agents selected from the group consisting of Docetaxel, Paclitaxel, Taxol, Ixabepilone, Patupilone, Sagopilone, Mitoxantrone, Predinisolone, Dexamethasone, Estramustin, Vinblastin, Vincristin, Doxorubicin, Adriamycin, Idarubicin, Daunorubicin, Bleomycin, Etoposide, Cyclophosphamide, Ifosfamide, Procarbazine, Melphalan, 5-Fluorouracil, Capecitabine, Fludarabine, Cytarabine, Ara-C, 2-Chloro-2'-deoxyadenosine, Thioguanine, Flutamide, Cyproterone acetate, Bicalutamide, Bortezomib, Cisplatin, Carboplatin, Chlorambucil, Methotrexate and Rituximab.

* * * * *